(12) United States Patent
Steen et al.

(10) Patent No.: US 11,698,378 B2
(45) Date of Patent: Jul. 11, 2023

(54) METHODS AND COMPOSITIONS FOR TAUOPATHY DIAGNOSIS AND TREATMENT

(71) Applicants: Judith AJ Steen, Brighton, MA (US); Hanno Steen, Brighton, MA (US); Waltraud Mair, Cambridge, MA (US); Jan Muntel, Cambridge, MA (US); Shaojun Tang, Dedham, MA (US); Children's Medical Center Corporation, Boston, MA (US)

(72) Inventors: Judith AJ Steen, Brighton, MA (US); Hanno Steen, Brighton, MA (US); Waltraud Mair, Cambridge, MA (US); Jan Muntel, Cambridge, MA (US); Shaojun Tang, Dedham, MA (US)

(73) Assignee: Children's Medical Center Corporation, Boston, MA (US)

( * ) Notice: Subject to any disclaimer, the term of this patent is extended or adjusted under 35 U.S.C. 154(b) by 82 days.

(21) Appl. No.: 15/762,720

(22) PCT Filed: Sep. 23, 2016

(86) PCT No.: PCT/US2016/053357
§ 371 (c)(1),
(2) Date: Mar. 23, 2018

(87) PCT Pub. No.: WO2017/053739
PCT Pub. Date: Mar. 30, 2017

(65) Prior Publication Data
US 2019/0234966 A1      Aug. 1, 2019

Related U.S. Application Data

(60) Provisional application No. 62/232,575, filed on Sep. 25, 2015.

(51) Int. Cl.
*G01N 33/68* (2006.01)
*C12Q 1/37* (2006.01)

(52) U.S. Cl.
CPC ........... *G01N 33/6896* (2013.01); *C12Q 1/37* (2013.01); *G01N 2440/00* (2013.01); *G01N 2800/2814* (2013.01); *G01N 2800/2821* (2013.01)

(58) Field of Classification Search
None
See application file for complete search history.

(56) References Cited

U.S. PATENT DOCUMENTS

2011/0312010 A1*  12/2011  Manuilov .......... G01N 33/6848
                                                435/23
2013/0034867 A1   2/2013   Bomgarden et al.
2014/0072991 A1*  3/2014   Mann .................... C07K 19/00
                                                435/23
2015/0253341 A1   9/2015   McAvoy et al.

OTHER PUBLICATIONS

Muntel "Abundance-based Classifier for the Prediction of Mass Spectrometric Peptide Detectability Upon Enrichment (PPA)" Mol Cell Prot 14.2: 430-440 (Year: 2014).*
Holman "The use of selected reaction monitoring in quantitative proteomics" bioanalysis 4(14):1763-1786 (Year: 2012).*
Kim "18O-Labeled Proteome Reference as Global Internal Standards for Targeted Quantification by Selected Reaction Monitoring-Mass Spectrometry" mol cell prot 10.12: (13 pages) (Year: 2011).*
Martin "Post-translational modifications of tau protein: Implications for Alzheimer's disease" neurochem int 58: 458-471 (Year: 2011).*
Schraen-Maschke "Tau as a biomarker of neurodegenerative diseases" Biomark med 2(4): 363-384 (Year: 2008).*
Cripps "Alzheimer Disease-specific Conformation of Hyperphosphorylated Paired Helical Filament-Tau Is Polyubiquitinated through Lys-48, Lys-11, and Lys-6 Ubiquitin Conjugation" JBC 281(16): 10825-10838 (Year: 2006).*
Mageean "Cellular responses to oncogenic Ras signalling" dissertation available online Sep. 15, 2014 (Year: 2014).*
Lange "Selected reaction monitoring for quantitative proteomics: a tutorial" Molecular Systems Biology 4:222 (Year: 2008).*
Schultz "A RanGTP-independent mechanism allows ribosomal protein nuclear import for ribosome assembly" eLife 2014;3:e03473 (Year: 2014).*
Holman "The use of selected reaction monitoring in quantitative proteomics" Bioanalysis (2012) 4(14), 1763-1786 (Year: 2012).*
Aebersold et al., "Applications and Developments in Targeted Proteomics: From SRM to DIA/SWATH," Proteomics, 16(15-16):2065-2067, Aug. 2016.
Alexander et al., "Validation of the new consensus criteria for the diagnosis of corticobasal degeneration," J. Neurol. Neurosurg. Psychiatry., 85(8):925-9, Aug. 2014.
Alonso et al., "Hyperphosphorylation induces self-assembly of tau into tangles of paired helical filaments/straight filaments," Proc. Natl. Acad. Sci. USA., 98(12):6923-6928, Jun. 2001.
Armstrong et al., "Criteria for the diagnosis of corticobasal degeneratio," Neurology, 80(5): 496-503, Jan. 2013.
Avila et al., "Role of tau protein in both physiological and pathological conditions," Physiological reviews, 84(2):361-384, Apr. 2004.

(Continued)

*Primary Examiner* — Adam Weidner
(74) *Attorney, Agent, or Firm* — Fish & Richardson P.C.

(57) ABSTRACT

This disclosure relates to methods of determining the amount of post translational modification (PTM) associated with one or more tau peptide fragments of a tau protein in a sample, and methods of evaluating a subject for having a tauopathy, the methods comprising, in part, determining the amount of post translational modification (PTM) associated with one or more tau peptide fragments of a tau protein in a sample, and comparing the amount of the tau PTMs associated with one or more tau peptide fragments with one or more reference levels for the tau peptide fragments, thereby determining whether a subject has a tauopathy.

21 Claims, 26 Drawing Sheets
(1 of 26 Drawing Sheet(s) Filed in Color)
Specification includes a Sequence Listing.

(56) References Cited

OTHER PUBLICATIONS

Ballatore et al., "Tau-mediated neurodegeneration in Alzheimer's disease and related disorders," Nature Reviews Neuroscience 8(9):663-672, Sep. 2007.
Barghorn et al., "Purification of recombinant tau protein and preparation of Alzheimer-paired helical filaments in vitro," Amyloid Proteins, Humana Press, 299:35-51, 2005.
Biernat and Mandelkow, "The development of cell processes induced by tau protein requires phosphorylation of serine 262 and 356 in the repeat domain and is inhibited by phosphorylation in the proline-rich domains," Mol. Biol. Cell, 10:727-740, Mar. 1999.
Biernat et al., "Phosphorylation of Ser262 strongly reduces binding of tau to microtubules: distinction between PHF-like immunoreactivity and microtubule binding," Neuron, 11:153-163, Jul. 1993.
Braak et al., "Allocortical neurofibrillary changes in progressive supranuclear palsy," Acta. Neuropathol., 84(5):478-83, Oct. 1992.
Bruderer et al., "Extending the limits of quantitative proteome profiling with data-independent acquisition and application to acetaminophen-treated three-dimensional liver microtissues," Molecular & Cellular Proteomics, 14(5):1400-1410, May 2015.
Bruderer et al., "High-precision iRT prediction in the targeted analysis of data-independent acquisition and its impact on identification and quantitation," Proteomics, 16(15-16):2246-56, Aug. 2016.
Brunden et al., "Advances in tau focused drug discovery for Alzheimer's disease and related tauopathies," Nature Reviews Drug Discovery, 8(10):783-793, Oct. 2009.
Chang et al., "SWATH analysis of the synaptic proteome in Alzheimer's disease," Neurochemistry international, 87:1-2, Aug. 2015.
Cohen et al., "The acetylation of tau inhibits its function and promotes pathological tau aggregation," Nature Communications, 2:252, Mar. 2011.
Cripps et al., "Alzheimer disease-specific conformation of hyperphosphorylated paired helical filament-Tau is polyubiquitinated through Lys-48, Lys-11, and Lys-6 ubiquitin conjugation," The Journal of biological chemistry, 281(16):10825-10838, Apr. 2006.
Dammer et al., "Quantitative phosphoproteomics of Alzheimer's disease reveals cross-talk between kinases and small heat shock proteins," Proteomics, 15(2-3):508-519, Jan. 2015.
Dickson DW, Hauw J-J, Agid Y, Litvan I. Progressive Supranuclear Palsy and Corticobasal Degeneration. Neurodegeneration: The Molecular Pathology of Dementia and Movement Disorders: Wiley-Blackwell; 2011: 135-55.
Dickson et al., "Neuropathology of Frontotemporal Lobar Degeneration-Tau (FTLD-Tau)," J. Mol, Neurosci., 45(3):384-9, Nov. 2011.
Dickson, "Neuropathologic differentiation of progressive supranuclear palsy and corticobasal degeneration," J. Neurol., 246(2):II6-15, Sep. 1999.
Dixit et al., "Differential regulation of dynein and kinesin motor proteins by tau," Science, 319(5866):1086-9, Feb. 2008.
Duka et al., "Identification of the sites of tauhyperphosphorylation and activation of tau kinases in synucleinopathies and Alzheimer's diseases," PLoS One, 8(9):e75025, Sep. 2013.
Espinoza et al., "Differential incorporation of tau isoforms in Alzheimer's disease," J. Alzheimers Dis., 14(1): 1-16, Jan. 2008.
Forman et al., "Signature tau neuropathology in gray and white matter of corticobasal degeneration," Am. J. Pathol., 160(6):2045-53, Jun. 2002.
Gillet et al., "Targeted data extraction of the MS/MS spectra generated by data-independent acquisition: a new concept for consistent and accurate proteome analysis," Molecular & Cellular Proteomics, 11(6):O111-016717, Jun. 2012.
Goedert and Spillantini, "Pathogenesis of the tauopathies," Journal of Molecular Neuroscience, 45(3):425-431, Nov. 2011.
Goedert et al., "Frontotemporal dementia: implications for understanding Alzheimer disease," Cold Spring Harb. Perspect. Med., 2(2):a006254, Feb. 2012.

Grinberg et al., "Argyrophilic grain disease differs from other tauopathies by lacking tau acetylation," Acta. Neuropathologica., 125(4):581-593, Apr. 2013.
Hanger et al., "New phosphorylation sites identified in hyperphosphorylated tau (paired helical filament-tau) from Alzheimer's disease brain using nanoelectrospray mass spectrometry. Journal of neurochemistry," 71(6):2465-2476, Dec. 1998.
Hanger et al., "Novel phosphorylation sites in tau from Alzheimer brain support a role for casein kinase 1 in disease pathogenesis," The Journal of biological chemistry, 282(32):23645-23654, Aug. 2007.
Hanger et al., "Tau phosphorylation: the therapeutic challenge for neurodegenerative disease," Trends in molecular medicine, 15:112-119, Mar. 2009.
Hof et al., "Distribution of cortical neurofibrillary tangles in progressive supranuclear palsy: a quantitative analysis of six cases," Acta. Neuropathol., 84(1):45-51, Jan. 1992.
International Preliminary Report on Patentability in International Application No. PCT/US2016/053357, dated Apr. 5, 2018, 12 pages.
International Search Report and Written Opinion in International Application No. PCT/US2016/053357, dated Feb. 21, 2017, 21 pages.
Invitation to Pay Additional Fees and, Where Applicable, Protest Fee in Application No. PCT/US2016/053357, dated Dec. 16, 2016, 3 pages.
Itoh et al., "Large-Scale, Multicenter Study of Cerebrospinal Fluid Tau Protein Phosphorylated at Serine 199 for the Antemortem Diagnosis of Alzheimer's Disease," Ann Neurol, 2001, 50: 150-156.
Josephs, "Key emerging issues in progressive supranuclear palsy and corticobasal degeneration," J. Neurol., 262(3): 783-8, Mar. 2015.
Kang et al., "Synapsin-1 and tau reciprocal O-GlcNAcylation and phosphorylation sites in mouse brain synaptosomes," Exp. Mol. Med., 45(6):e29, Jun. 2013.
Kessner et al., "ProteoWizard: open source software for rapid proteomics tools development," Bioinformatics, 24(21):2534-2536, Jul. 2008.
Kovacs, "Invited review: Neuropathology of tauopathies: principles and practice," Neuropathology and applied neurobiology, 41(1):3-23, Feb. 2015.
Lange et al., "Selected reaction monitoring for quantitative proteomics: a tutorial," Molecular Systems Biology, 4(1):222, Jan. 2008.
Law and Lim., "Recent advances in mass spectrometry: data independent analysis and hyper reaction monitoring," Expert review of proteomics 10(6):551-566, Dec. 2013.
Lee et al., "Neurodegenerative tauopathies," Annual review of neuroscience, 24(1):1121-1159, Mar. 2001.
Ling et al., "Characteristics of progressive supranuclear palsy presenting with corticobasal syndrome: a cortical variant," Neuropathology and applied neurobiology, 40(2):149-63, Feb. 2014.
Ling et al., "Does corticobasal degeneration exist? A clinicopathological re-evaluation," Brain, 133(7):2045-57, Jun. 2010.
Liu et al., "O-GlcNAcylation regulates phosphorylation of tau: a mechanism involved in Alzheimer's disease," Proceedings of the National Academy of Sciences, 101(29): 10804-10809, Jul. 2004.
MacLean et al., "Skyline: an open source document editor for creating and analyzing targeted proteomics experiments." Bioinformatics, 26(7):966-968, Feb. 2010.
Mair et al., "FLEXITau: Quantifying Post-translational Modifications of Tau Protein in Vitro and in Human Disease," Anal Chem, Mar. 2016, 88: 3704-3714.
Martin et al., "Post-translational modifications of tau protein: implications for Alzheimer's disease," Neurochem. Int., 58(4):458-71, Mar. 2011.
Merrill and Coon, "Quantifying proteomes and their post translational modifications by stable isotope label-based mass spectrometry," Current opinion in chemical biology, 17(5):779-786, Oct. 2013.
Noble et al., "The importance of tau phosphorylation for neurodegenerative diseases," Frontiers in Neurology, 4:83, Jul. 2013.

(56) References Cited

OTHER PUBLICATIONS

Olsen and Mann, "Status of large-scale analysis of post-translational modifications by mass spectrometry," Molecular & cellular proteomics, 12(12):3444-3452, Dec. 2013.

Ouchi et al., "Pathology and sensitivity of current clinical criteria in corticobasal syndrome," Mov. Disord., 29(2):238-44, Feb. 2014.

Parker et al., "Mass Spectrometry for Post-Translational Modifications," In: Alzate, O., ed. Neuroproteomics, Boca Raton FL, 2010.

Peterson et al., "Parallel Reaction Monitoring for High Resolution and High Mass Accuracy Quantitative, Targeted Proteomics," Molecular & Cellular Proteomics, 11(11):1475-1488, Nov. 2012.

Piao et al., "Cerebellar cortical tau pathology in progressive supranuclear palsy and corticobasal degeneration," Acta. Neuropathol., 103(5):469-74, May 2002.

Picotti et al., "Full dynamic range proteome analysis of S. cerevisiae by targeted proteomics," Cell, 138(4):795-806, Aug. 2009.

Picotti et al., "Selected reaction monitoring-based proteomics: workflows, potential, pitfalls and future directions," Nature methods, 9(6):555-566, Jun. 2012.

Rardin et al., "MS1 peptide ion intensity chromatograms in MS2 (SWATH) data independent acquisitions. Improving post acquisition analysis of proteomic experiments," Molecular & Cellular Proteomics, 14(9):2405-2419, Sep. 2015.

Respondek et al., "The phenotypic spectrum of progressive supranuclear palsy: a retrospective multicenter study of 100 definite cases," Movement disorders, 29(14):1758-66, Dec. 2014.

Rosenberger et al., "A repository of assays to quantify 10,000 human proteins by SWATH-MS," Scientific data, 1:140031, Sep. 2014.

Röst et al., "OpenSWATH enables automated, targeted analysis of data-independent acquisition MS data," Nature biotechnology, 32(3):219-223, Mar. 2014.

Schilling et al., "Platform-independent and label-free quantitation of proteomic data using MSI extracted ion chromatograms in Skyline application to protein acetylation and phosphorylation," Molecular & cellular proteomics, 11(5):202-214, May 2012.

Schneider et al., "Phosphorylation that detaches tau protein from microtubules (Ser262, Ser214) also protects it against aggregation into Alzheimer paired helical filaments," Biochemistry, 38(12):3549-3558, Mar. 1999.

Schubert, Olga T., et al. "Building high-quality assay libraries for targeted analysis of SWATH MS data." Nature protocols 10.3 (2015): 426-441.

Seelaar et al., "Clinical, genetic and pathological heterogeneity of frontotemporal dementia: a review," Journal of neurology, neurosurgery, and psychiatry, 82(5):476-86, May 2011.

Sergeant et al., "Different distribution of phosphorylated tau protein isoforms in Alzheimer's and Pick's diseases," FEBS Letters, 412(3):578-582, Aug. 1997.

Sergeant et al., "Tau protein as a differential biomarker of tauopathies," Biochim. Biophys. Acta., 1739(2-3):179-97, Jan. 2005.

Sidoli et al., "Sequential Window Acquisition of all Theoretical Mass Spectra (SWATH) Analysis for characterization and quantification of histone post-translational modifications," Molecular & Cellular Proteomics 14(9):2420-2428, Sep. 2015.

Singh et al., "FLEXIQinase, a mass spectrometry-based assay, to unveil multikinase mechanisms," Nat. Methods, 9:504-508, May 2012.

Singh et al., "FLEXIQuant: a novel tool for the absolute quantification of proteins, and the simultaneous identification and quantification of potentially modified peptides," J. Proteome Res., 8(5):2201-10, Apr. 2009.

Spillantini and Goedert, "Tau pathology and neurodegeneration," Lancet Neurol., 12(6):609-22, Jun. 2013.

Tepper et al., "Oligomer formation of tau protein hyperphosphorylated in cells," Journal of Biological Chemistry, 289(49):34389-34407, Dec. 2014.

Thal et al., "Frontotemporal lobar degeneration FTLD-tau: preclinical lesions, vascular, and Alzheimer-related co-pathologies," J. Neural Transm., 122(7): 1007-18, Jul. 2015.

Thomas et al., "Dual modification of Alzheimer's disease PHF-tau protein by lysine methylation and ubiquitylation: a mass spectrometry approach," Acta. Neuropathologica, 123(1):105-117, Jan. 2012.

Tsuboi et al., "Increased tau burden in the cortices of progressive supranuclear palsy presenting with corticobasal syndrome," Mov. Disord., 20(8):982-8, Aug. 2005.

Tsuchiya et al., "Distribution of cerebral cortical lesions in corticobasal degeneration: a clinicopathological study of five autopsy cases in Japan," Acta. Neuropathol., 94(5):416-24, Oct. 1997.

Unwin et al., "A sensitive mass spectrometric method for hypothesis-driven detection of peptide post-translational modifications: multiple reaction monitoringinitiated detection and sequencing (MIDAS)," Nat. Protoc., 4:870-877, Jun. 2009.

Venne, "The next level of complexity: crosstalk of posttranslational modifications," Proteomics, 14(4-5):513-524, Mar. 2014.

Verny et al., "The significance of cortical pathology in progressive supranuclear palsy: clinico-pathological data in 10 cases," Brain, 119(4):1123-36, Aug. 1996.

Wadia and Lang, "The many faces of corticobasal degeneration," Parkinsonism & related disorders, 13:S3:S336-40, Jan. 2007.

Wakabayashi and Takahashi, "Pathological heterogeneity in progressive supranuclear palsy and corticobasal degeneration," Neuropathology, 24(1):79-86, Mar. 2004.

Wang et al., "Perspectives of comprehensive phosphoproteome analysis using shotgun strategy," Anal. Chem., 83(21):8078-8085, Oct. 2011.

Williams and Lees, "Progressive supranuclear palsy: clinicopathological concepts and diagnostic challenges," The Lancet Neurology, 8(3):270-9, Mar. 2009.

Williams et al., "Pathological tau burden 5 and distribution distinguishes progressive supranuclear palsy parkinsonism from Richardson's syndrome," Brain, 130:1566-76, 2007.

Wray et al., "Direct analysis of tau from PSP brain identifies new phosphorylation sites and a major fragment of N terminally cleaved tau containing four microtubule-binding repeats," Journal of neurochemistry, 105:2343-2352, Jun. 2008.

Yoshida, "Cellular tau pathology and immunohistochemical study of tau isoforms in sporadic tauopathies," Neuropathology, 26(5):457-70, Oct. 2006.

Zhang et al., "The Use of Variable Q1 Isolation Windows Improves Selectivity in LC-SWATH-MS Acquisition," Journal of proteome research 14(10):4359-4371, Sep. 2015.

Zheng-Fischhöfer et al., "Sequential phosphorylation of Tau by glycogen synthase kinase-3beta and protein kinase A at Thr212 and Ser214 generates the Alzheimer specific epitope of antibody AT100 and requires a paired-helical-filament-like conformation," European journal of biochemistry FEBS, 252:542-552, Mar. 1998.

* cited by examiner

```
  1 MAEPRQEFEV MEDHAGTYGL GDRKDQGGYT MHQDQEGDTD AGLKESPLQT
 51 PTEDGSEEPG SETSDAKSTP TAEDVTAPLV DEGAPGKQAA AQPHTEIPEG
101 TTAEEAGIGD TPSLEDEAAG HVTQARMVSK SKDGTGSDDK KAKGADGKTK
151 IATPRGAAPP GQKGQANATR IPAKTPPAPK TPPSSGEPPK SGDRSGYSSP
201 GSPGTPGSRS RTPSLPTPPT REPKKVAVVR TPPKSPSSAK SRLQTAPVPM
251 PDLKNVKSKI GSTENLKHQP GGGKVQIINK KLDLSNVQSK CGSKDNIKHV
301 PGGGSVQIVY KPVDLSKVTS KCGSLGNIHH KPGGGQVEVK SEKLDFKDRV
351 QSKIGSLDNI THVPGGGNKK IETHKLTFRE NAKAKTDHGA EIVYKSPVVS
401 GDTSPRHLSN VSSTGSIDMV DSPQLATLAD EVSASLAKQG L
```

SEQ ID NO: 18

Tryptic sequence coverage
Additional LysC coverage

FIG. 1D

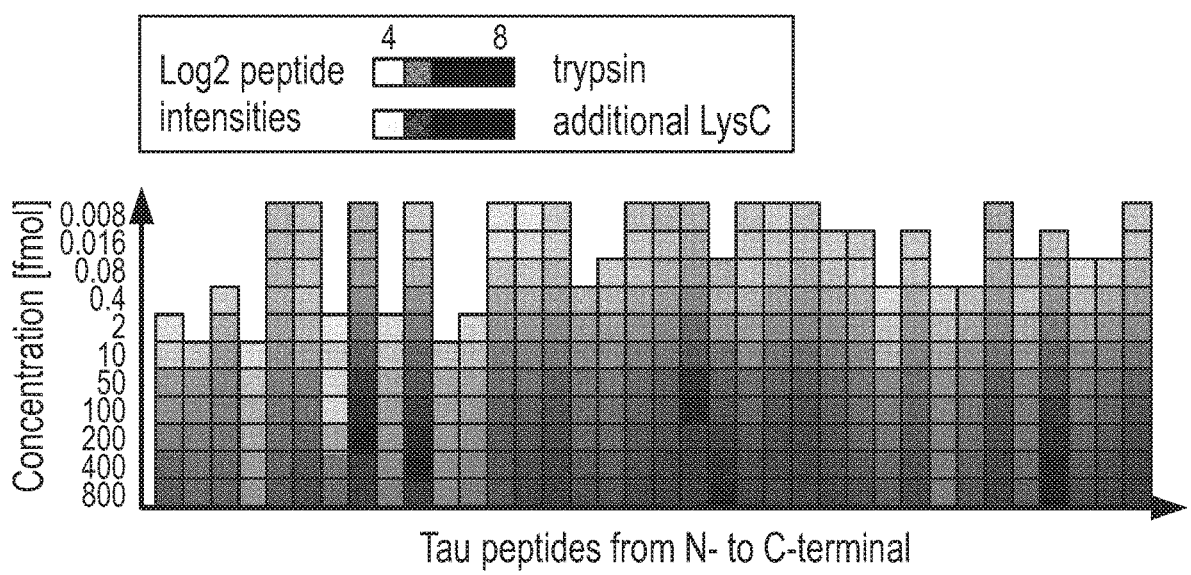

FIG. 2A

| | | Tau peptide sequence | | start-end | P-tau | pp-tau | AD tau | Reported modifications | References |
|---|---|---|---|---|---|---|---|---|---|
| I | SEQ ID NO: 14 | IGSLDNITHVPGGGNK | T | 354-369 | | | | Ub-K353, S356 | a, d, e, f, h |
| | SEQ ID NO: 30 | SEKLDFK | S | 341-347 | | | | | |
| | SEQ ID NO: 29 | CGSLGNIHHKPGGGQVEVK | R | 322-340 | | | | | |
| II | SEQ ID NO: 10 | LQTAPVPMPDLK | M | 243-254 | | | | Ub-K254 | a, e |
| | SEQ ID NO: 31 | LTFRENAK | U | 376-383 | | | | | |
| III | SEQ ID NO: 13 | HVPGGGSVQIVYKPVDLSK | Q | 299-317 | | | | S305, Ub-K311, exon 10 splicing | a, e, h |
| | SEQ ID NO: 1 | QEFEVMEDHAGTYGLGDR | A | 6-23 | | | | Y18 | d, f |
| | SEQ ID NO: 5 | QAAAQPHTEIPEGTTAEEAG(...)R | E | 88-127 | | | | T111, S113, T123, exon3 splicing | b, d, e, f, h |
| | SEQ ID NO: 11 | KLDLSNVQSK | P | 281-290 | | | | Ac-K280, S289, exon 10 splicing | b, c, d, f, h |
| | SEQ ID NO: 21 | GQANATRIPAK | G | 164-174 | | | | T175, Ac-K280 | d, h |
| | SEQ ID NO: 28 | VQIINK | O | 275-280 | | | | Ac-K274, Ac-K280, exon 10 splicing | g, c |
| IV | SEQ ID NO: 4 | STPTAEDVTAPLVDEGAPGK | D | 68-87 | | | | S68, T69, T71, exon 2 splicing | b, d, e, f |
| | SEQ ID NO: 32 | AKTDHGAEIVYK | V | 384-395 | | | | Y394, S396 | a, b, d, e, f, h |
| | SEQ ID NO: 27 | IGSTENLK | N | 260-267 | | | | S262 | a, b, d, e, f, h |
| | SEQ ID NO: 20 | IATPRGAAPPGQK | F | 151-163 | | | | T153 | d, f |
| | SEQ ID NO: 54 | HLSNVSSTGSIDMVDSPQLA(...)K | X | 407-438 | | | | S409, S412, S413, S416, S422, T427, S433, S435 | d, e, f, h |
| V | SEQ ID NO: 57 | KDQGGYTMQDQEGDTDAGLK | B | 24-44 | | | | S46, T50, S68, exon 2 splicing | |
| | SEQ ID NO: 3 | ESPLQTPTEDGSEEPGSETSDAK | C | 45-67 | | | | T175, T181 | d, f |
| | SEQ ID NO: 22 | TPPAPK | H | 175-180 | | | | T181, S184, S185, S191 | b, d, f, h |
| | SEQ ID NO: 23 | TPPSSGEPPK.SGDR | I | 181-194 | | | | S210, T212, S214, T217 | b, d, f, h |
| | SEQ ID NO: 25 | SR.TPSLPTPPTR.EPK | K | 210-224 | | | | T231, S235 | a, b, d, e, f, h |
| VI | SEQ ID NO: 26 | VAVVRTPPK | L | 226-234 | | | | S396, S400, T403, S404 | a, b, d, e, f, h |
| | SEQ ID NO: 16 | SPVVSGDTSPR | W | 396-406 | | | | Y197, T198, S199, S202, T205, S208, S210 | b, d, f, h |
| | SEQ ID NO: 7 | SGYSSPGSPGTPGSR | J | 195-209 | | | | | |

FIG. 5B

SEQUENCE LISTING

<160> NUMBER OF SEQ ID NOS: 57

<210> SEQ ID NO 1
<211> LENGTH: 18
<212> TYPE: PRT
<213> ORGANISM: Homo sapiens

<400> SEQUENCE: 1

Gln Glu Phe Glu Val Met Glu Asp His Ala Gly Thr Tyr Gly Leu Gly
1               5                   10                  15

Asp Arg

<210> SEQ ID NO 2
<211> LENGTH: 20
<212> TYPE: PRT
<213> ORGANISM: Homo sapiens

<400> SEQUENCE: 2

Asp Gln Gly Gly Tyr Thr Met His Gln Asp Gln Glu Gly Asp Thr Asp
1               5                   10                  15

Ala Gly Leu Lys
            20

<210> SEQ ID NO 3

```
<211> LENGTH: 23
<212> TYPE: PRT
<213> ORGANISM: Homo sapiens

<400> SEQUENCE: 3

Glu Ser Pro Leu Gln Thr Pro Thr Glu Asp Gly Ser Glu Glu Pro Gly
1               5                   10                  15

Ser Glu Thr Ser Asp Ala Lys
            20

<210> SEQ ID NO 4
<211> LENGTH: 20
<212> TYPE: PRT
<213> ORGANISM: Homo sapiens

<400> SEQUENCE: 4

Ser Thr Pro Thr Ala Glu Asp Val Thr Ala Pro Leu Val Asp Glu Gly
1               5                   10                  15

Ala Pro Gly Lys
            20

<210> SEQ ID NO 5
<211> LENGTH: 39
<212> TYPE: PRT
<213> ORGANISM: Homo sapiens

<400> SEQUENCE: 5

Gln Ala Ala Ala Gln Pro His Thr Glu Ile Pro Glu Gly Thr Thr Ala
1               5                   10                  15

Glu Glu Ala Gly Ile Gly Asp Thr Pro Ser Leu Glu Asp Glu Ala Ala
            20                  25                  30

Gly His Val Thr Gln Ala Arg
        35

<210> SEQ ID NO 6
<211> LENGTH: 10
<212> TYPE: PRT
<213> ORGANISM: Homo sapiens

<400> SEQUENCE: 6

Thr Pro Pro Ser Ser Gly Glu Pro Pro Lys
1               5                   10

<210> SEQ ID NO 7
<211> LENGTH: 15
<212> TYPE: PRT
<213> ORGANISM: Homo sapiens

<400> SEQUENCE: 7

Ser Gly Tyr Ser Ser Pro Gly Ser Pro Gly Thr Pro Gly Ser Arg
1               5                   10                  15

<210> SEQ ID NO 8
<211> LENGTH: 10
<212> TYPE: PRT
<213> ORGANISM: Homo sapiens

<400> SEQUENCE: 8

Thr Pro Ser Leu Pro Thr Pro Pro Thr Arg
1               5                   10

<210> SEQ ID NO 9
<211> LENGTH: 13
```

```
<212> TYPE: PRT
<213> ORGANISM: Homo sapiens

<400> SEQUENCE: 9

Thr Pro Ser Leu Pro Thr Pro Pro Thr Arg Glu Pro Lys
1               5                   10

<210> SEQ ID NO 10
<211> LENGTH: 12
<212> TYPE: PRT
<213> ORGANISM: Homo sapiens

<400> SEQUENCE: 10

Leu Gln Thr Ala Pro Val Pro Met Pro Asp Leu Lys
1               5                   10

<210> SEQ ID NO 11
<211> LENGTH: 10
<212> TYPE: PRT
<213> ORGANISM: Homo sapiens

<400> SEQUENCE: 11

Lys Leu Asp Leu Ser Asn Val Gln Ser Lys
1               5                   10

<210> SEQ ID NO 12
<211> LENGTH: 9
<212> TYPE: PRT
<213> ORGANISM: Homo sapiens

<400> SEQUENCE: 12

Leu Asp Leu Ser Asn Val Gln Ser Lys
1               5

<210> SEQ ID NO 13
<211> LENGTH: 19
<212> TYPE: PRT
<213> ORGANISM: Homo sapiens

<400> SEQUENCE: 13

His Val Pro Gly Gly Gly Ser Val Gln Ile Val Tyr Lys Pro Val Asp
1               5                   10                  15

Leu Ser Lys

<210> SEQ ID NO 14
<211> LENGTH: 16
<212> TYPE: PRT
<213> ORGANISM: Homo sapiens

<400> SEQUENCE: 14

Ile Gly Ser Leu Asp Asn Ile Thr His Val Pro Gly Gly Gly Asn Lys
1               5                   10                  15

<210> SEQ ID NO 15
<211> LENGTH: 10
<212> TYPE: PRT
<213> ORGANISM: Homo sapiens

<400> SEQUENCE: 15

Thr Asp His Gly Ala Glu Ile Val Tyr Lys
1               5                   10

<210> SEQ ID NO 16
<211> LENGTH: 11
```

```
<212> TYPE: PRT
<213> ORGANISM: Homo sapiens

<400> SEQUENCE: 16

Ser Pro Val Val Ser Gly Asp Thr Ser Pro Arg
1               5                   10

<210> SEQ ID NO 17
<211> LENGTH: 36
<212> TYPE: PRT
<213> ORGANISM: Homo sapiens

<400> SEQUENCE: 17

His Leu Ser Asn Val Ser Ser Thr Gly Ser Ile Asp Met Val Asp Ser
1               5                   10                  15

Pro Gln Leu Ala Thr Leu Ala Asp Glu Val Ser Ala Val Ser Ala Ser
            20                  25                  30

Ser Leu Ala Lys
        35

<210> SEQ ID NO 18
<211> LENGTH: 439
<212> TYPE: PRT
<213> ORGANISM: Homo sapiens

<400> SEQUENCE: 18

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Ala Glu Ala Gly Ile Gly Asp Thr Pro Ser
            100                 105                 110

Leu Glu Asp Glu Ala Ala Gly His Val Thr Gln Ala Arg Met Val Ser
        115                 120                 125

Lys Ser Lys Asp Gly Thr Gly Ser Asp Asp Lys Lys Ala Lys Gly Ala
    130                 135                 140

Asp Gly Lys Thr Lys Ala Thr Pro Arg Gly Ala Ala Pro Pro Gly Gln
145                 150                 155                 160

Lys Gly Gln Ala Asn Ala Thr Arg Ile Pro Ala Lys Thr Pro Pro Ala
                165                 170                 175

Pro Lys Thr Pro Pro Ser Ser Gly Glu Pro Lys Ser Gly Asp Arg
            180                 185                 190

Ser Gly Tyr Ser Ser Pro Gly Ser Pro Gly Thr Pro Gly Ser Arg Ser
        195                 200                 205

Arg Thr Pro Ser Leu Pro Thr Pro Pro Thr Arg Glu Pro Lys Lys Val
    210                 215                 220

Ala Val Val Arg Thr Pro Pro Lys Ser Pro Ser Ser Ala Lys Ser Arg
225                 230                 235                 240

Leu Gln Thr Ala Pro Val Pro Met Pro Asp Leu Lys Asn Val Lys Ser
```

245                 250                 255
Lys Ile Gly Ser Thr Glu Asn Leu Lys His Gln Pro Gly Gly Gly Lys
            260                 265                 270

Val Gln Ile Ile Asn Lys Lys Leu Asp Leu Ser Asn Val Gln Ser Lys
        275                 280                 285

Cys Gly Ser Lys Asp Asn Ile Lys His Val Pro Gly Gly Gly Ser Val
    290                 295                 300

Gln Ile Val Tyr Lys Pro Val Asp Leu Ser Lys Val Thr Ser Lys Cys
305                 310                 315                 320

Gly Ser Leu Gly Asn Ile His His Lys Pro Gly Gly Gly Gln Val Glu
                325                 330                 335

Val Lys Ser Glu Lys Leu Asp Phe Lys Asp Arg Val Gln Ser Lys Ile
            340                 345                 350

Gly Ser Leu Asp Asn Ile Thr His Val Pro Gly Gly Gly Asn Lys Lys
        355                 360                 365

Ile Glu Thr His Lys Leu Thr Phe Arg Glu Asn Ala Lys Ala Lys Thr
    370                 375                 380

Asp His Gly Ala Glu Ile Val Tyr Lys Ser Pro Val Val Ser Gly Asp
385                 390                 395                 400

Thr Ser Pro Arg His Leu Ser Asn Val Ser Ser Thr Gly Ser Ile Asp
                405                 410                 415

Met Val Asp Ser Pro Gln Leu Ala Thr Leu Ala Asp Glu Val Ser Ala
            420                 425                 430

Ser Leu Ala Lys Gln Gly Leu
        435

<210> SEQ ID NO 19
<211> LENGTH: 21
<212> TYPE: PRT
<213> ORGANISM: Homo sapiens

<400> SEQUENCE: 19

Lys Asp Gln Gly Gly Tyr Thr Met His Gln Asp Gln Glu Gly Asp Thr
1               5                   10                  15

Asp Ala Gly Leu Lys
            20

<210> SEQ ID NO 20
<211> LENGTH: 13
<212> TYPE: PRT
<213> ORGANISM: Homo sapiens

<400> SEQUENCE: 20

Ile Ala Thr Pro Arg Gly Ala Ala Pro Pro Gly Gln Lys
1               5                   10

<210> SEQ ID NO 21
<211> LENGTH: 11
<212> TYPE: PRT
<213> ORGANISM: Homo sapiens

<400> SEQUENCE: 21

Gly Gln Ala Asn Ala Thr Arg Ile Pro Ala Lys
1               5                   10

<210> SEQ ID NO 22
<211> LENGTH: 6
<212> TYPE: PRT
<213> ORGANISM: Homo sapiens

<400> SEQUENCE: 22

Thr Pro Pro Ala Pro Lys
1               5

<210> SEQ ID NO 23
<211> LENGTH: 14
<212> TYPE: PRT
<213> ORGANISM: Homo sapiens

<400> SEQUENCE: 23

Thr Pro Pro Ser Ser Gly Glu Pro Pro Lys Ser Gly Asp Arg
1               5                   10

<210> SEQ ID NO 24
<211> LENGTH: 12
<212> TYPE: PRT
<213> ORGANISM: Homo sapiens

<400> SEQUENCE: 24

Ser Arg Thr Pro Ser Leu Pro Thr Pro Pro Thr Arg
1               5                   10

<210> SEQ ID NO 25
<211> LENGTH: 15
<212> TYPE: PRT
<213> ORGANISM: Homo sapiens

<400> SEQUENCE: 25

Ser Arg Thr Pro Ser Leu Pro Thr Pro Pro Thr Arg Glu Pro Lys
1               5                   10                  15

<210> SEQ ID NO 26
<211> LENGTH: 9
<212> TYPE: PRT
<213> ORGANISM: Homo sapiens

<400> SEQUENCE: 26

Val Ala Val Val Arg Thr Pro Pro Lys
1               5

<210> SEQ ID NO 27
<211> LENGTH: 8
<212> TYPE: PRT
<213> ORGANISM: Homo sapiens

<400> SEQUENCE: 27

Ile Gly Ser Thr Glu Asn Leu Lys
1               5

<210> SEQ ID NO 28
<211> LENGTH: 6
<212> TYPE: PRT
<213> ORGANISM: Homo sapiens

<400> SEQUENCE: 28

Val Gln Ile Ile Asn Lys
1               5

<210> SEQ ID NO 29
<211> LENGTH: 19
<212> TYPE: PRT
<213> ORGANISM: Homo sapiens

<400> SEQUENCE: 29

```
Cys Gly Ser Leu Gly Asn Ile His His Lys Pro Gly Gly Gln Val
1               5                   10                  15

Glu Val Lys
```

<210> SEQ ID NO 30
<211> LENGTH: 7
<212> TYPE: PRT
<213> ORGANISM: Homo sapiens

<400> SEQUENCE: 30

```
Ser Glu Lys Leu Asp Phe Lys
1               5
```

<210> SEQ ID NO 31
<211> LENGTH: 8
<212> TYPE: PRT
<213> ORGANISM: Homo sapiens

<400> SEQUENCE: 31

```
Leu Thr Phe Arg Glu Asn Ala Lys
1               5
```

<210> SEQ ID NO 32
<211> LENGTH: 12
<212> TYPE: PRT
<213> ORGANISM: Homo sapiens

<400> SEQUENCE: 32

```
Ala Lys Thr Asp His Gly Ala Glu Ile Val Tyr Lys
1               5                   10
```

<210> SEQ ID NO 33
<211> LENGTH: 7
<212> TYPE: PRT
<213> ORGANISM: Homo sapiens

<400> SEQUENCE: 33

```
Thr Lys Ile Ala Thr Pro Arg
1               5
```

<210> SEQ ID NO 34
<211> LENGTH: 15
<212> TYPE: PRT
<213> ORGANISM: Homo sapiens

<400> SEQUENCE: 34

```
Thr Lys Ile Ala Thr Pro Arg Gly Ala Ala Pro Pro Gly Gln Lys
1               5                   10                  15
```

<210> SEQ ID NO 35
<211> LENGTH: 5
<212> TYPE: PRT
<213> ORGANISM: Homo sapiens

<400> SEQUENCE: 35

```
Ile Ala Thr Pro Arg
1               5
```

<210> SEQ ID NO 36
<211> LENGTH: 17
<212> TYPE: PRT
<213> ORGANISM: Homo sapiens

<400> SEQUENCE: 36

```
Gly Gln Ala Asn Ala Thr Arg Ile Pro Ala Lys Thr Pro Pro Ala Pro
1               5                   10                  15
Lys

<210> SEQ ID NO 37
<211> LENGTH: 10
<212> TYPE: PRT
<213> ORGANISM: Homo sapiens

<400> SEQUENCE: 37

Ile Pro Ala Lys Thr Pro Pro Ala Pro Lys
1               5                   10

<210> SEQ ID NO 38
<211> LENGTH: 20
<212> TYPE: PRT
<213> ORGANISM: Homo sapiens

<400> SEQUENCE: 38

Thr Pro Pro Ala Pro Lys Thr Pro Pro Ser Ser Gly Glu Pro Pro Lys
1               5                   10                  15

Ser Gly Asp Arg
            20

<210> SEQ ID NO 39
<211> LENGTH: 27
<212> TYPE: PRT
<213> ORGANISM: Homo sapiens

<400> SEQUENCE: 39

Gly Gln Ala Asn Ala Thr Arg Ile Pro Ala Lys Thr Pro Pro Ala Pro
1               5                   10                  15

Lys Thr Pro Pro Ser Ser Gly Glu Pro Pro Lys
            20                  25

<210> SEQ ID NO 40
<211> LENGTH: 20
<212> TYPE: PRT
<213> ORGANISM: Homo sapiens

<400> SEQUENCE: 40

Ile Pro Ala Lys Thr Pro Pro Ala Pro Lys Thr Pro Pro Ser Ser Gly
1               5                   10                  15

Glu Pro Pro Lys
            20

<210> SEQ ID NO 41
<211> LENGTH: 16
<212> TYPE: PRT
<213> ORGANISM: Homo sapiens

<400> SEQUENCE: 41

Thr Pro Pro Ala Pro Lys Thr Pro Pro Ser Ser Gly Glu Pro Pro Lys
1               5                   10                  15

<210> SEQ ID NO 42
<211> LENGTH: 10
<212> TYPE: PRT
<213> ORGANISM: Homo sapiens

<400> SEQUENCE: 42

Lys Val Ala Val Val Arg Thr Pro Pro Lys
```

```
1               5                   10
```

<210> SEQ ID NO 43
<211> LENGTH: 16
<212> TYPE: PRT
<213> ORGANISM: Homo sapiens

<400> SEQUENCE: 43

```
Lys Val Ala Val Val Arg Thr Pro Pro Lys Ser Pro Ser Ser Ala Lys
1               5                   10                  15
```

<210> SEQ ID NO 44
<211> LENGTH: 10
<212> TYPE: PRT
<213> ORGANISM: Homo sapiens

<400> SEQUENCE: 44

```
Thr Pro Pro Lys Ser Pro Ser Ser Ala Lys
1               5                   10
```

<210> SEQ ID NO 45
<211> LENGTH: 15
<212> TYPE: PRT
<213> ORGANISM: Homo sapiens

<400> SEQUENCE: 45

```
Val Ala Val Val Arg Thr Pro Pro Lys Ser Pro Ser Ser Ala Lys
1               5                   10                  15
```

<210> SEQ ID NO 46
<211> LENGTH: 15
<212> TYPE: PRT
<213> ORGANISM: Homo sapiens

<400> SEQUENCE: 46

```
Ile Gly Ser Thr Glu Asn Leu Lys His Gln Pro Gly Gly Gly Lys
1               5                   10                  15
```

<210> SEQ ID NO 47
<211> LENGTH: 10
<212> TYPE: PRT
<213> ORGANISM: Homo sapiens

<400> SEQUENCE: 47

```
Ser Lys Ile Gly Ser Thr Glu Asn Leu Lys
1               5                   10
```

<210> SEQ ID NO 48
<211> LENGTH: 17
<212> TYPE: PRT
<213> ORGANISM: Homo sapiens

<400> SEQUENCE: 48

```
Ser Lys Ile Gly Ser Thr Glu Asn Leu Lys His Gln Pro Gly Gly Gly
1               5                   10                  15

Lys
```

<210> SEQ ID NO 49
<211> LENGTH: 8
<212> TYPE: PRT
<213> ORGANISM: Homo sapiens

<400> SEQUENCE: 49

```
Cys Gly Ser Lys Asp Asn Ile Lys
```

```
<210> SEQ ID NO 50
<211> LENGTH: 22
<212> TYPE: PRT
<213> ORGANISM: Homo sapiens

<400> SEQUENCE: 50

Asp Arg Val Gln Ser Lys Ile Gly Ser Leu Asp Asn Ile Thr His Val
1               5                   10                  15

Pro Gly Gly Gly Asn Lys
            20

<210> SEQ ID NO 51
<211> LENGTH: 17
<212> TYPE: PRT
<213> ORGANISM: Homo sapiens

<400> SEQUENCE: 51

Lys Ile Gly Ser Leu Asp Asn Ile Thr His Val Pro Gly Gly Gly Asn
1               5                   10                  15

Lys

<210> SEQ ID NO 52
<211> LENGTH: 23
<212> TYPE: PRT
<213> ORGANISM: Homo sapiens

<400> SEQUENCE: 52

Ala Lys Thr Asp His Gly Ala Glu Ile Val Tyr Lys Ser Pro Val Val
1               5                   10                  15

Ser Gly Asp Thr Ser Pro Arg
            20

<210> SEQ ID NO 53
<211> LENGTH: 21
<212> TYPE: PRT
<213> ORGANISM: Homo sapiens

<400> SEQUENCE: 53

Thr Asp His Gly Ala Glu Ile Val Tyr Lys Ser Pro Val Val Ser Gly
1               5                   10                  15

Asp Thr Ser Pro Arg
            20

<210> SEQ ID NO 54
<211> LENGTH: 32
<212> TYPE: PRT
<213> ORGANISM: Homo sapiens

<400> SEQUENCE: 54

His Leu Ser Asn Val Ser Ser Thr Gly Ser Ile Asp Met Val Asp Ser
1               5                   10                  15

Pro Gln Leu Ala Thr Leu Ala Asp Glu Val Ser Ala Ser Leu Ala Lys
            20                  25                  30

<210> SEQ ID NO 55
<211> LENGTH: 19
<212> TYPE: PRT
<213> ORGANISM: Homo sapiens

<400> SEQUENCE: 55
```

```
Asp Gln Gly Gly Tyr Thr Met His Gln Asp Gln Glu Gly Asp Thr Asp
1               5                   10                  15

Ala Gly Leu

<210> SEQ ID NO 56
<211> LENGTH: 21
<212> TYPE: PRT
<213> ORGANISM: Homo sapiens

<400> SEQUENCE: 56

Thr Asp His Gly Ala Glu Ile Val Tyr Lys Ser Pro Val Val Ser Gly
1               5                   10                  15

Asp Thr Ser Pro Arg
            20

<210> SEQ ID NO 57
<211> LENGTH: 20
<212> TYPE: PRT
<213> ORGANISM: Homo sapiens

<400> SEQUENCE: 57

Lys Asp Gln Gly Gly Tyr Thr Met Gln Asp Gln Glu Gly Asp Thr Asp
1               5                   10                  15

Ala Gly Leu Lys
            20
```

METHODS AND COMPOSITIONS FOR TAUOPATHY DIAGNOSIS AND TREATMENT

CLAIM OF PRIORITY

This application is a 371 U.S. National Phase Application of PCT Application No. PCT/US2016/053357, filed on Sep. 23, 2016, which claims the benefit of U.S. Provisional Application Ser. No. 62/232,575, filed on Sep. 25, 2015. The entire contents of the foregoing are incorporated herein by reference.

FEDERALLY SPONSORED RESEARCH OR DEVELOPMENT

This invention was made with Government support under Grant No. RC4GM096319, S10OD010706, ROINS066973, HHS-NIH-NIDA(MH)-12-265, AG023501 and AG19724 awarded by the National Institutes of Health, and under a NIH Contract HHSN-271-2013-00030C. The Government has certain rights in the invention.

TECHNICAL FIELD

This disclosure relates to diagnosing and treating tauopathies.

BACKGROUND

Neurodegenerative diseases are a major cause of disability and premature death among older people worldwide (Savica R, Grossardt B R, Bower J H, Boeve B F, Ahlskog J E, Rocca W A. Incidence of dementia with Lewy bodies and Parkinson disease dementia. JAMA Neurol 2013; 70(11): 1396-402). These conditions usually cause dementia and are clinically characterized by progressive behavioral changes, executive dysfunction and impairment of cognition and memory, ultimately affecting many of the body's activities. Today, an estimated 44 million people worldwide live with dementia; driven by a rapidly ageing population and due to the lack of prevention and cure, its frequency is expected to double by 2030, and to triple by 2050 (Prince M, Wimo A, Guerchet M, Ali G-C, Wu Y-T, Prina M. The World Alzheimer Report 2015. Alzheimer's Disease International 2015).

The atypical deposition of characteristic proteins into insoluble aggregates inside or among specific neurons and glial cells is a shared feature of neurodegenerative diseases, thus also referred to as proteopathies (Ross C A, Poirier M A. Protein aggregation and neurodegenerative disease. Nat Med 2004; 10 Suppl: S10-7). Tauopathies represent a large group of proteopathies featuring aggregates of an altered form of the microtubule associated protein tau. Tau is a microtubule (MT)-associated protein particularly abundant in neurons, where it mostly localizes to axonal regions. The most prominent function of tau is the regulation of MT stability and the maintenance of axonal transport. Under physiological conditions, tau binding to MTs is coordinated by phosphorylation, requiring a precise interplay of a multitude of kinases and phosphatases. In pathological conditions, such as Alzheimer Disease (AD) and related neurodegenerative disorders called tauopathies, increased phosphorylation of tau is associated with a decrease in its binding to microtubules. This in turn results in tau misfolding and self-aggregation, eventually leading to the accumulation of insoluble, paired helical filaments (PHFs) and other filamentous structures. This pathological tau aggregation is a shared molecular mechanism in more than 20 neurodegenerative conditions, including AD (Spillantini M G, Goedert M. Tau pathology and neurodegeneration. Lancet Neurol 2013; 12(6): 609-22).

While tau in the normal brain contains 2-3 phosphorylated residues per tau molecule, it is estimated to be approximately 3-fold hyper-phosphorylated in AD brain. Accumulating data indicates that phosphorylation alone is not sufficient for aggregation and might even serve a protective role. Several other Post-Translational Modifications (PTMs) such as acetylation, ubiquitination, methylation, and glycosylation, among others, appear to play regulatory roles as well with respect to rates of tau clearance and aggregation and thus contribute to tau pathology. Thus, there is a need to develop an assay to determine the PTM of the tau protein, and identify the pathological PTM in various tauopathies for developing diagnosis and treatment.

SUMMARY

This disclosure relates to diagnosing and treating tauopathies.

In one aspect, this disclosure provides a method for evaluating a subject for having a tauopathy, the method including (a) obtaining a first sample from the subject; (b) determining the amount of post translational modification (PTM) associated with one or more tau peptide fragments of a tau protein in the first sample, wherein determining the amount of PTM includes the steps of providing a second sample comprising a labeled tau protein; mixing the first sample and the second sample at an initial mixing ratio of tau protein to labeled tau protein to form a mixture; subjecting the mixture to proteolytic digestion, generating tau peptide fragments and labeled tau peptide fragments; quantifying the abundance of the tau peptide fragments and the labeled tau peptide fragments; measuring the ratio of the abundance of the tau peptide fragments and the labeled tau peptide fragments; determining the amount of the tau PTMs associated with one or more tau peptide fragments by comparing the measured ratio for each tau peptide fragment to the initial mixing ratio, wherein the extent of deviation from the initial mixing ratio indicates the amount of PTMs in the tau peptide fragment; (c) comparing the amount of the tau PTMs associated with one or more tau peptide fragments with one or more reference levels for the tau peptide fragments; and (d) identifying the patient as having a tauopathy if the level of PTM associated with one or more tau peptide fragments in the patient sample is altered relative to the reference level for the tau peptide fragments.

In some embodiments, the tau protein in the first sample is not a labeled tau protein. In some embodiments, the first sample includes an endogenous tau protein. In some embodiments, the first sample is brain tissue, plasma, or cerebrospinal fluid (CSF).

In some embodiments, the tauopathy is selected from the group consisting of Alzheimer's disease (AD), Argyrophilic grain disease (AGD), Corticobasal degeneration (CBD), Pick's disease (PiD) and Progressive supranuclear palsy (PSP).

In some embodiments, the tau peptide fragments are selected from the group consisting of (QEFEVMEDHAGTYGLGDR), SEQ ID NO: 1

(DQGGYTMHQDQEGDTDAGLK), SEQ ID NO: 2

(ESPLQTPTEDGSEEPGSETSDAK), SEQ ID NO: 3

(STPTAEDVTAPLVDEGAPGK), SEQ ID NO: 4

(QAAAQPHTEIPEGTTAEEAGIGDTPSLEDEAAGHVTQAR), SEQ ID NO: 5

(TPPSSGEPPK), SEQ ID NO: 6

(SGYSSPGSPGTPGSR), SEQ ID NO: 7

(TPSLPTPPTR), SEQ ID NO: 8

(TPSLPTPPTREPK), SEQ ID NO: 9

(LQTAPVPMPDLK), SEQ ID NO: 10

(KLDLSNVQSK), SEQ ID NO: 11

(LDLSNVQSK), SEQ ID NO: 12

(HVPGGGSVQIVYKPVDLSK), SEQ ID NO: 13

(IGSLDNITHVPGGGNK), SEQ ID NO: 14

(TDHGAEIVYK), SEQ ID NO: 15

(SPVVSGDTSPR), and SEQ ID NO: 16

(HLSNVSSTGSIDMVDSPQLATLADEVSAVSASSLAK). SEQ ID NO: 17

In some embodiments, the method includes the step of identifying the subject as not having a tauopathy if the level of tau PTM associated with tau peptide fragments selected from the SEQ ID NO: 3, SEQ ID NO: 8, SEQ ID NO: 12, SEQ ID NO: 13, SEQ ID NO: 14, SEQ ID NO: 16, SEQ ID NO: 17 (or any combination of two or more thereof) in the first sample from the subject are significantly altered relative to the control level for each tau peptide fragment.

In some embodiments, the method includes the step of identifying the subject as having Alzheimer's Disease (AD) and not AGD, PSP CSB or PiD if the level of tau PTM associated with tau peptide fragments selected from SEQ ID NO: 7, SEQ ID NO: 9, SEQ ID NO: 10, SEQ ID NO: 11, SEQ ID NO: 14, SEQ ID NO: 16, SEQ ID NO: 17 (or any combination of two or more thereof) are significantly altered in the first sample from the subject relative to the level of tau PTM in a patient diagnosed with AGD, PSP, CBD, PiD, and/or a subject that is non-demented.

In some embodiments, the method includes the step of identifying the subject as having a Argyrophilic grain disease (AGD) and not AD, AGD, PSP, or CBD if the level of tau PTM associated with tau peptide fragments selected from the SEQ ID NO: 3, SEQ ID NO: 9, SEQ ID NO: 12, SEQ ID NO: 14, SEQ ID NO: 16, SEQ ID NO: 17 (or any combination of two or more thereof) are significantly altered in the first sample from the subject relative to the level of tau PTM associated in a patient diagnosed with AD, PSP, CBD, PiD, and/or a subject that is non-demented.

In some embodiments, the method includes the step of identifying the subject as having a Progressive supranuclear palsy (PSP) if the level of tau PTM associated with tau peptide fragments selected from the SEQ ID NO: 3, SEQ ID NO: 4, SEQ ID NO: 7, SEQ ID NO: 9, SEQ ID NO: 10, SEQ ID NO: 11, SEQ ID NO: 13, SEQ ID NO: 15 (or any combination of two or more thereof) are significantly altered in the first sample from the subject relative to the level of tau PTM associated in a patient diagnosed with AD, AGD, CBD, PiD, and/or a subject that is non-demented.

In some embodiments, the method includes the step of identifying the subject as having a Corticobasal degeneration (CBD) and not AD, AGD, PSP or PiD if the level of tau PTM associated with tau peptide fragments selected from the SEQ ID NO: 4, SEQ ID NO: 11, SEQ ID NO: 12, SEQ ID NO: 13, SEQ ID NO: 14, SEQ ID NO: 15, SEQ ID NO: 16, SEQ ID NO: 17 (or any combination of two or more thereof) are significantly altered in the first sample from the subject relative to the level of tau PTM associated in a patient diagnosed with AD, AGD, PSP, PiD, and/or a subject that is non-demented.

In some embodiments, the method includes the step of identifying the subject as having a Pick's disease (PiD) and not AD, AGD, PSP, or CBD if the level of tau PTM associated with tau peptide fragments selected from the SEQ ID NO: 9, SEQ ID NO: 10, SEQ ID NO: 11, SEQ ID NO: 12, SEQ ID NO: 13, SEQ ID NO: 14, SEQ ID NO: 17 (or any combination of two or more thereof) are significantly altered in the first sample from the subject relative to the level of tau PTM associated in a patient diagnosed with AD, AGD, CBD, PSP, and/or a subject that is non-demented.

In some embodiments, the step of subjecting the mixture to proteolytic digestion is performed using one or more proteases. In some embodiments, one or more proteases are selected from the group consisting of trypsin, Lys-C, Arg-C, Asp-N, Glu-C, Lys-N, thermolysin, elastase, Tryp-N, and chymotrypsin.

In some embodiments, the method includes the step of purifying the tau protein in the first sample and the labeled tau protein in the second sample before mixing the first sample and the second sample.

In some embodiments, the labeled tau protein is a fusion protein with the tau protein conjugated to first member of a binding pair, wherein the binding pair is selected from the group consisting of biotin/streptavidin, biotin/avidin, biotin/neutravidin, biotin/captavidin, epitope/antibody, protein A/immunoglobulin, protein G/immunoglobulin, protein L/immunoglobulin, GST/glutathione, His-tag/Metal (e.g., nickel, cobalt or copper), antigen/antibody, FLAG/M1 antibody, maltose binding protein/maltose, calmodulin binding protein/calmodulin, enzyme-enzyme substrate, and receptor-ligand binding pairs.

In some embodiments, the post-translational modification is phosphorylation, glycosylation, glycation, prolyl-isomerization, cleavage or truncation, nitration, polyamination, ubiquitination, acetylation, methylation, dimethylation, trimethylation or sumoylation.

In some embodiments, the mixing ratio of labeled tau protein to tau protein is 4:1, 3:1, 2:1, 1:1, 1:2, 1:3 or 1:4.

In some embodiments, the abundance of the tau peptide fragments and the labeled tau peptide fragments are determined by liquid chromatography-selected reaction monitoring (LC-SRM) or Parallel Reaction Monitoring (PRM).

In some embodiments, the reference sample includes predetermined, statistically significant reference analyte levels.

In one aspect, the disclosure also provides a method for quantifying the amount of post-translational modifications on a tau protein. The method includes the steps of providing a first sample comprising an unlabeled tau protein; providing a second sample comprising a labeled tau protein; mixing the first sample and the second sample at an initial mixing ratio of unlabeled tau protein to labeled tau protein to form a mixture; subjecting the mixture to proteolytic digestion, generating unlabeled tau peptide fragments and labeled tau peptide fragments; quantifying the abundance of the unlabeled tau peptide fragments and the labeled tau peptide fragments; measuring the ratio of the abundance of the unlabeled tau peptide fragments and the labeled tau peptide fragments, and comparing the ratio for each peptide fragment to the initial mixing ratio, wherein the extent of deviation from the initial mixing ratio indicates the amount of PTMs in the unlabeled protein; and quantifying the amount of PTMs in the tau protein of the first sample.

In some embodiments, the abundance of the unlabeled tau peptide fragments and the labeled tau peptide fragments are determined by liquid chromatography-selected reaction monitoring (LC-SRM) or Parallel Reaction Monitoring (PRM).

In some embodiments, the first sample is a clinical sample. In some embodiments, the first sample is a biological sample.

In some embodiments, the initial mixing ratio is 1:1.

In some embodiments, the labeled tau protein is generated from a cell-free expression system in the presence of isotopically labeled amino acids.

In some embodiments, the labeled tau protein includes one or more isotope-label amino acid residues. The isotope can be selected from the group consisting of $^{13}C$ and $^{15}N$.

In some embodiments, the step of determining the abundance of the unlabeled tau peptide fragments and the labeled tau peptide fragments includes the step of identifying an ion signal associated with a peptide and/or its fragment ions.

In some embodiments, the step of subjecting the mixture to proteolytic digestion is performed using one or more proteases. In some embodiments, the proteases can be selected from the group consisting of trypsin, Lys-C, Arg-C, Asp-N, Glu-C, Lys-N, thermolysin, elastase, and chymotrypsin.

In some embodiments, the method includes the step of purifying the unlabeled tau protein in the first sample and the labeled tau protein in the second sample before mixing the first sample and the second sample.

In some embodiments, the labeled tau protein is a fusion protein having the tau protein conjugated to first member of a binding pair, wherein the binding pair is selected from the group consisting of biotin/streptavidin, biotin/avidin, biotin/neutravidin, biotin/captavidin, epitope/antibody, protein A/immunoglobulin, protein G/immunoglobulin, protein L/immunoglobulin, GST/glutathione, His-tag/Metal (e.g., nickel, cobalt or copper), antigen/antibody, FLAG/M1 antibody, maltose binding protein/maltose, calmodulin binding protein/calmodulin, enzyme-enzyme substrate, and receptor-ligand binding pairs.

In some embodiments, the unlabeled tau protein is a recombinant protein. In some embodiments, the unlabeled tau protein is obtained from a human subject, a human immortalized cell line, or induced pluripotent stem cells.

In some embodiments, the post-translational modification is phosphorylation, glycosylation, glycation, prolyl-isomerization, cleavage or truncation, nitration, polyamination, ubiquitination, acetylation, methylation, dimethylation, trimethylation or sumoylation.

In another aspect, the disclosure provides a method for quantifying the amount of post-translational modifications on a tau protein, which includes providing a mixture comprising a first sample comprising an unlabeled tau protein fragments and a second sample comprising labeled tau peptide fragments; quantifying the abundance of the unlabeled tau peptide fragments and the labeled tau peptide fragments; measuring the ratio of the abundance of the unlabeled tau peptide fragments and the labeled tau peptide fragments, and comparing the ratio for each peptide fragment to the initial mixing ratio, wherein the extent of deviation from the initial mixing ratio indicates the amount of PTMs in the unlabeled protein; and quantifying the amount of PTMs in the tau protein of the first sample.

In some embodiments, the abundance of the unlabeled tau peptide fragments and the labeled tau peptide fragments are determined by liquid chromatography-selected reaction monitoring (LC-SRM) or Parallel Reaction Monitoring (PRM).

In some embodiments, the first sample is a clinical sample.

In some embodiments, the mixture of step a) is prepared by (i) providing a first sample comprising an unlabeled tau protein; (ii) providing a second sample comprising a labeled tau protein; (ii) mixing the first sample and the second sample at an initial mixing ratio of unlabeled tau protein to labeled tau protein to form a mixture; (iv) subjecting the mixture to proteolytic digestion, generating unlabeled tau peptide fragments and labeled tau peptide fragments; and (v) mixing the first sample and the second sample at an initial mixing ratio of unlabeled tau protein to labeled tau protein to form a mixture.

In some embodiments, the mixture of step a) is prepared by (i) providing a first sample comprising an unlabeled tau protein; (ii) subjecting the first sample to proteolytic digestion, generating unlabeled tau peptide fragments; (iii) providing a second sample comprising labeled tau peptide fragments, wherein the labeled tau peptide fragments are obtained from proteolytic digestion of a labeled tau protein; and (iv) mixing the first sample and the second sample at an initial mixing ratio of unlabeled tau protein to labeled tau protein to form a mixture.

In one aspect, this disclosure further provides a tau peptide fragment (SEQ ID NO: 1-17) with one or more modifications as listed in Table 1 and Table 7.

In one aspect, this disclosure provides an antibody or antibody fragment thereof that binds to a tau protein with one or more PTMs as listed in Table 1 and Table 7. In some embodiments, the antibody or antibody fragment thereof does not bind to the tau protein without said PTMs.

In another aspect, this disclosure provides an antibody or antibody fragment thereof that binds to a tau peptide fragment with one or more PTMs as listed in Table 1 and Table 7. In some embodiments, the antibody or antibody fragment thereof does not bind to the tau peptide fragment without said PTMs.

This disclosure also provides a composition comprising the antibody or antibody fragment thereof that binds to a tau protein with one or more PTMs as listed in Table 1 and Table 7 or a tau peptide fragment with one or more PTMs as listed in Table 1 and Table 7.

As used herein, the term "significant" or "significantly" refers to statistical significance (or a statistically significant result) is attained when a p-value is less than the significance level (denoted a, alpha). The p-value is the probability of obtaining at least as extreme results given that the null hypothesis is true whereas the significance level a is the probability of rejecting the null hypothesis given that it is true. In some embodiments, the significance level is 0.05, 0.01, 0.005, 0.001, 0.0001, or 0.00001, etc. In some embodiments, "significantly altered" or "significantly different" refers to the difference between the two groups have attained the statistical significance.

As used herein, the term "extent of deviation" refers to the ratio of the abundance of the unlabeled tau peptide fragments and the labeled tau peptide fragments (Result Value) as compared the initial mixing ratio (Initial Value). In some embodiments, the extent of deviation is the ratio of Result Value to Initial Value.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIG. 1D shows sequence coverage of quantifiable tau peptides (tau sequence of human 4R2N protein, SEQ ID NO: 18) by SRM (in bold) and additional coverage using LysC (in gray).

FIG. 2A is a graph showing the detection limit of one exemplary method of quantifying the amount of post-translational modifications.

FIG. 5B is a schematic diagram showing quantified peptides that were sorted into categories using hierarchical clustering (Euclidean distance, Ward's criteria).

after tenfold training and testing of RF classifier on randomly chosen test sets with a predetermined maximum number of splitter variables.

Figure 12A:
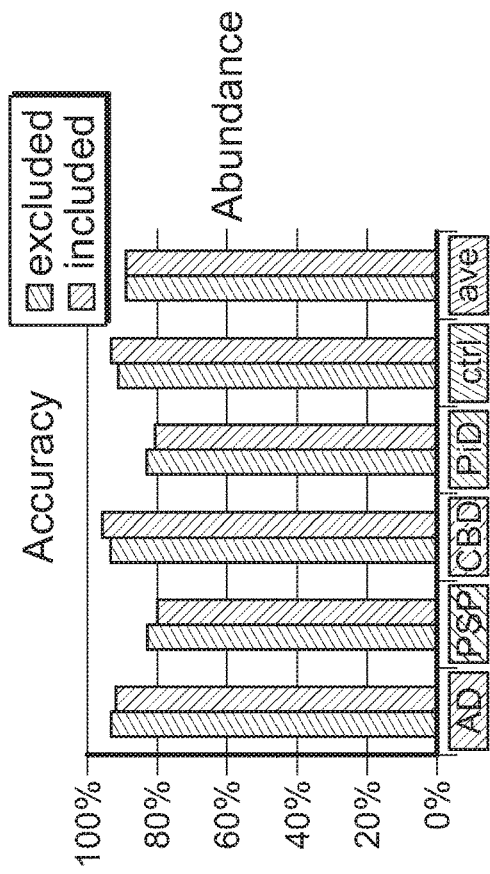

FIG. 12A is a graph showing accuracy of the RF classifier that was evaluated upon inclusion of abundance of as additional feature into the feature set.

Figure 12B:
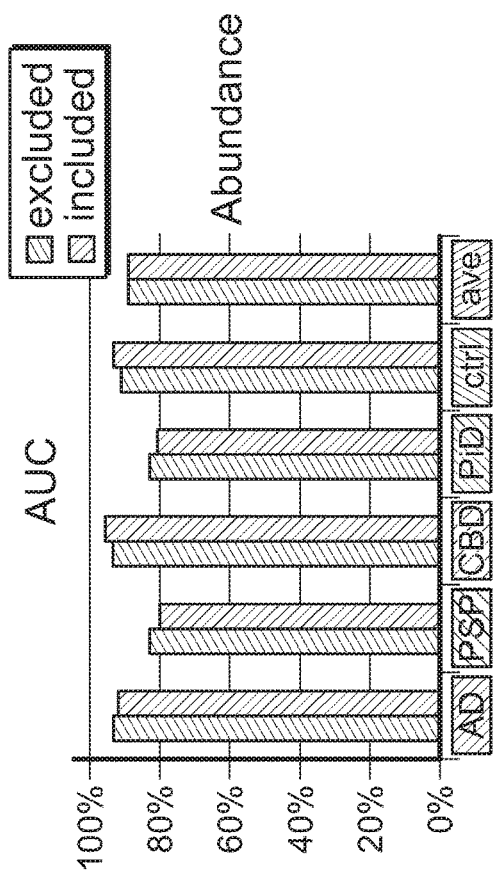

FIG. 12B is a graph showing AUC of the RF classifier that was evaluated upon inclusion of abundance of as additional feature into the feature set.

Figure 12C:
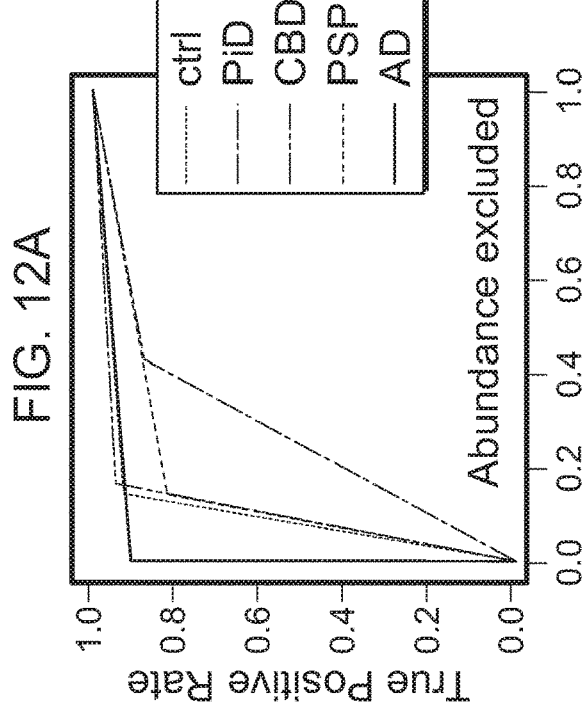

FIG. 12C is a graph showing performance of each classifier in ROC space upon exclusion of the abundance feature.

Figure 12D:
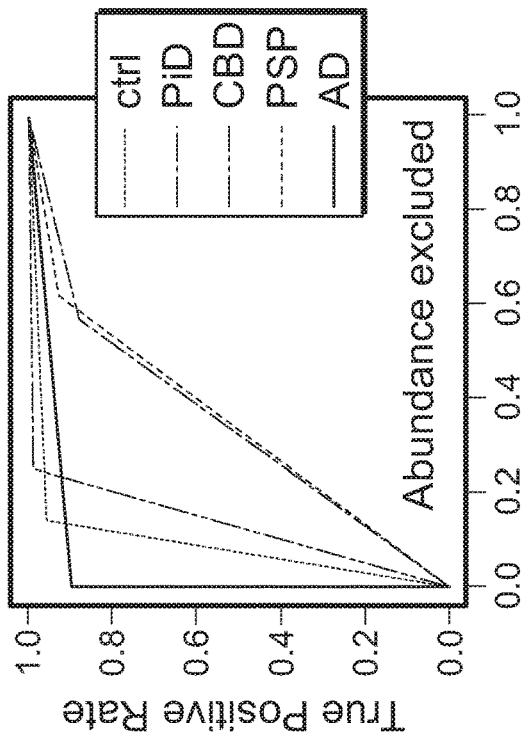

FIG. 12D is a graph showing performance of each classifier in ROC space upon inclusion of the abundance feature.

Figure 13A:
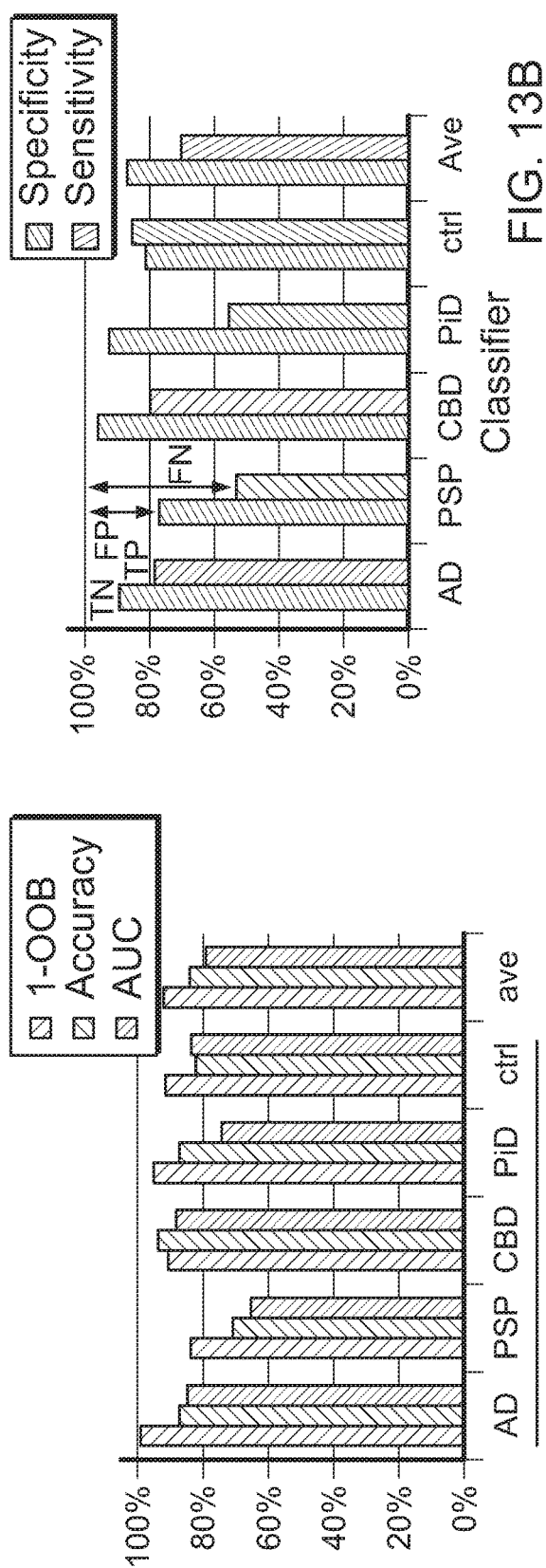

FIG. 13A is a graph showing OOB accuracy, accuracy and AUC for an exemplary classifier based on the RF method that was trained for each disease group using the entire training set.

Figure 13B:
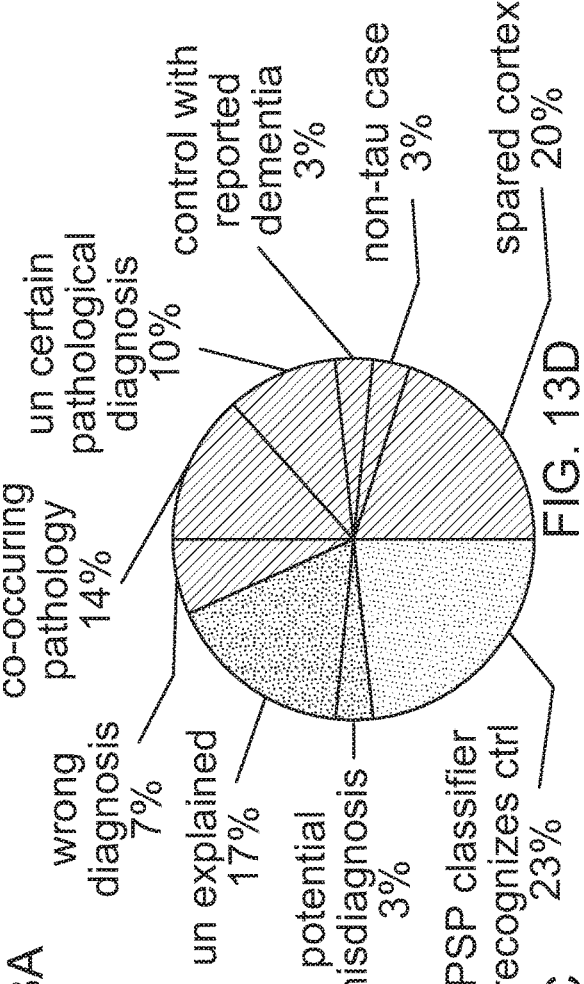

FIG. 13B is a graph showing specificity and sensitivity for an exemplary classifier based on the RF method that was trained for each disease group using the entire training set.

Figure 13C:
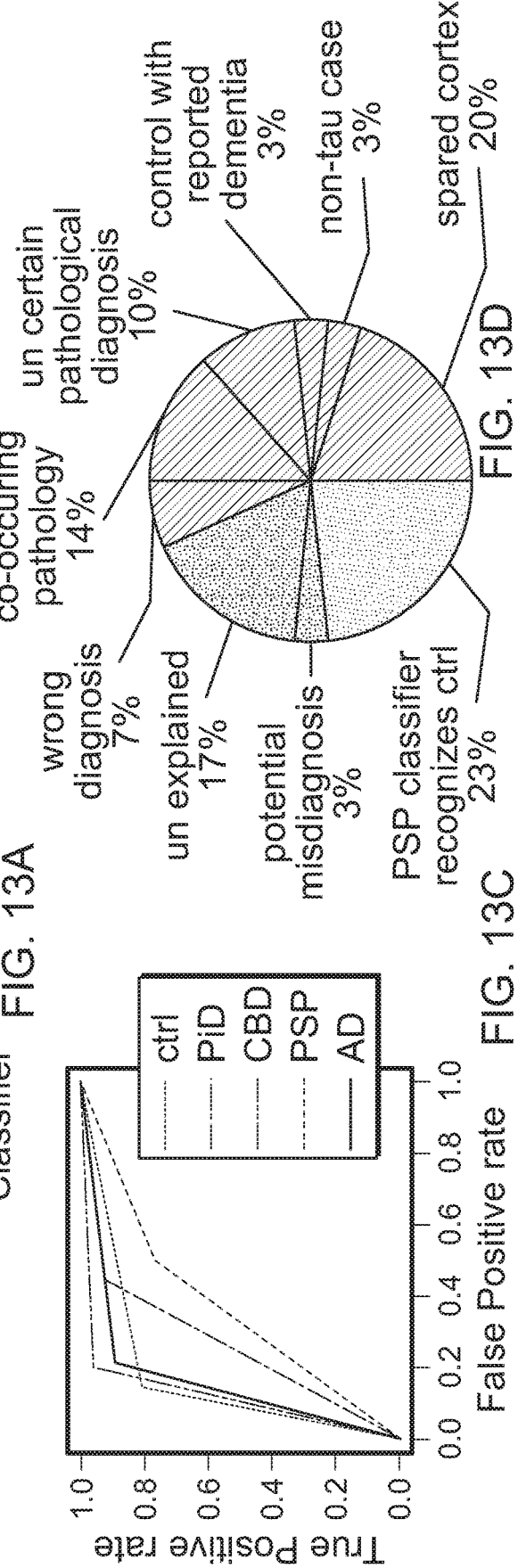

FIG. 13C is a graph showing performance in ROC space for an exemplary classifier based on the RF method that was trained for each disease group using the entire training set.

Figure 13D:
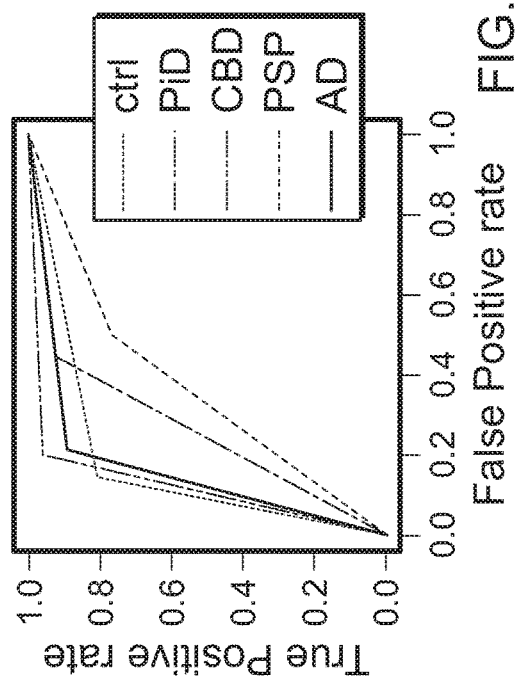

FIG. 13D is a graph showing identification of false negative (FN) cases for each classifier.

Figure 14A:
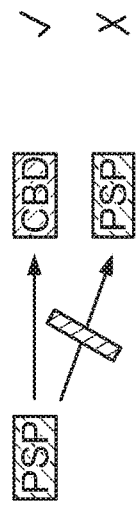

FIG. 14A is a schematic diagram showing that 3 PiD cases were classified as PiD and as AD by the RF classifiers.

Figure 14B:
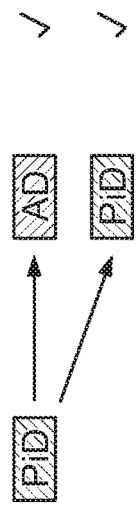

FIG. 14B is a schematic diagram showing that PSP case that was not recognized by the PSP classifier was instead classified as AD by the AD classifier.

Figure 14C:

FIG. 14C is a schematic diagram showing that one exemplary PSP case for evidence of cortical area being spared by tau pathology.

Figure 14D:
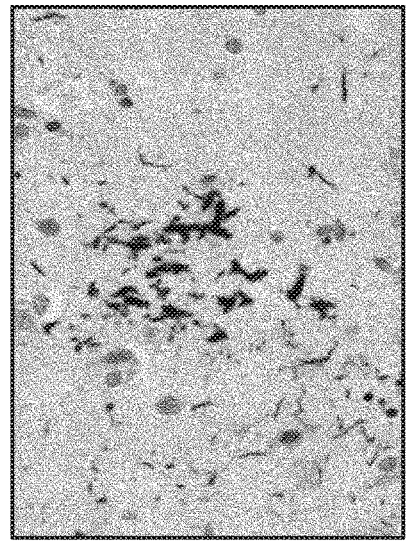

FIG. 14D is a schematic diagram showing that one case diagnosed as PSP with unusual severe pathology in the brainstem was classified as CBD.

Figure 14E:

FIG. 14E is a photo showing that immunohistochemistry (4R tau) of this case shows 4R tau positive astrocytic plaques confirming the correct diagnosis as being CBD.

DETAILED DESCRIPTION

This disclosure provides, in part, methods for evaluating a subject for having a tauopathy, and methods for quantifying the amount of post-translational modifications (PTMs) on a tau protein.

Extensive post-translational modifications of tau protein are implicated in the formation of neurofibrillary tangles, a hallmark of AD and many other related tauopathies, but strategies to address and measure tau PTMs in vitro or in vivo are limited. The number and diversity of tau modifications is large (alone for phosphorylation, over 70 sites have been described), and tau is believed to be regulated by the complex interplay and crosstalk of PTMs. Current approaches to determine tau modifications are not capable of capturing the many possible combinations of PTMs simultaneously, let alone in a quantitative manner. One advantage of the methods described in this disclosure is that the disclosed methods can be used to study a limitless number of modification sites and species without requiring prior information about the number and diversity of modifications, thus circumventing many issues typically encountered when using other methods. The methods further involve the addition of a stable isotope-labeled internal standard that enables the quantification of the tau PTM landscape in a comprehensive manner. This disclosure also provides a highly sensitive, robust tau-specific assay that can measure tau peptides down to amol quantities. Thus, the present disclosure provides an effective tool to precisely measure and compare the extent of tau PTMs in both purified and complex sample backgrounds and is not limited by the number of sites or types of PTMs.

The abnormal tau protein accumulating in characteristic insoluble structures is known to carry many post-translational modifications (PTMs). Thus, it can be hypothesized that the characteristic types and distribution of the tau inclusions have underpinnings which may be defined by the molecular nature of tau, whereby specific PTMs and PTMs found in specific stoichiometries result in these characteristic tau inclusions specific to each tauopathy. Profiling the specific molecular characteristics of tau in these tauopathies will enable the diagnosis, prognosis and the development of directed therapies.

Although extensive effort has been put into studying tau and its modifications, the exact molecular and cellular mechanism leading to tau misfolding and aggregation, in particular the relevant combination of modifications, remains poorly understood. The study of tau PTMs is particularly challenging due to the large number of modified sites. For instance, over 70 phosphorylation sites (out of the 85 putative sites) have been described. Individual modifications have been associated with certain tauopathies, but not others, suggesting that disease-specific PTM patterns exist. The analysis is further complicated by the coexistence of multiple types of modifications present at one time point, sometimes even competing for the same site. Finally, some of the modifications are challenging to detect due to low stoichiometries, as may be the case for ubiquitination or certain phosphorylation sites. Taken together, the PTM landscape of tau is highly complex and heterogeneous and that its investigation requires a systematic and quantitative strategy that can measure tau modifications with high precision and accuracy. Furthermore, substantial overlap in clinical phenotypes and the recent recognition of many atypical manifestations have complicated clinical diagnosis of these disorders (Williams D R, Lees A J. Progressive supranuclear palsy: clinicopathological concepts and diagnostic challenges. The Lancet Neurology 2009; 8(3): 270-9; Respondek G, Stamelou M, Kurz C, et al. The phenotypic spectrum of progressive supranuclear palsy: a retrospective multicenter study of 100 definite cases. Movement disorders: official journal of the Movement Disorder Society 2014; 29(14): 1758-66; Ling H, Ling H, de Silva R, et al. Characteristics of progressive supranuclear palsy presenting with corticobasal syndrome: a cortical variant. Neuropathology and applied neurobiology 2014; 40(2): 149-63). Despite significant progress in developing diagnostic biomarkers for some of these conditions, these methods do not permit their reliable differentiation in vivo. In some cases, an accurate diagnosis depends on post-mortem analysis, involving the investigation of specific types and location of inclusions among the diseases by neuropathological techniques. Post-mortem classification is time consuming and labor intensive as it involves rigorous investigation of anatomical distributions and abnormalities using an array of immunohistological staining methods, and the neuropathological standards are subject to change over time. In addition, even a post-mortem diagnosis is sometimes difficult due to pathological heterogeneity, disease-overlapping histopathological features, and co-morbidities. Furthermore, post-mortem diagnosis of tauopathies is labor intensive, involving extensive gross and histological analysis. The diagnosis is often based on the identification of characteristic morphologies, neuron loss, tau lesions and their distribution using classical histological and, immunohistochemical staining techniques (Kovacs G G. Invited review: Neuropathology of tauopathies: principles and practice. Neuropathology and applied neurobiology 2015; 41(1): 3-23). Variability in protocols and staining quality as well as the visual evaluation of histopathological findings by each pathologist complicates diagnosis and may cause inter-brain bank inconsistencies in diagnosis (Alafuzoff I, Arzberger T, Al-Sarraj S, et al. Staging of neurofibrillary pathology in Alzheimer's disease: a study of the BrainNet Europe Consortium. Brain Pathol 2008; 18(4): 484-96; Alafuzoff I, Pikkarainen M, Al-Sarraj S, et al. Interlaboratory comparison of assessments of Alzheimer disease-related lesions: a study of the BrainNet Europe Consortium. J Neuropathol Exp Neurol 2006; 65(8): 740-57).

The most commonly used method to analyze tau PTMs are immuno-based approaches. A large array of tau antibodies specific to phosphorylated or otherwise modified epitopes exists. These antibodies have been useful tools in the study of tau pathogenesis and the role of phosphorylation in neurodegeneration. However, immunoassays are limited by low throughput and suffer from variable affinity and specificity. Furthermore, given the molecular diversity of tau, their selectivity has often been questioned, and a priori knowledge of particular PTMs is required.

Mass spectrometry (MS)-based proteomics approaches are a powerful alternative method used to identify proteins and characterize modifications. In the case of tau, exploitation of this technology resulted in greatly enhanced protein sequence coverage and high throughput. Furthermore, data-dependent-acquisition (DDA), a data collection mode that depends on the 'detectability' of the modified peptide species, is often used in MS-based proteomics approaches. The limitation of such data-dependent proteomics is the stochastic selection of ions for fragmentation, biasing the analysis towards peptides of highest intensity. This particularly handicaps the identification of PTMs, as the modified species can be present in very low stoichiometries compared to the unmodified counterpart. To overcome this limitation, some studies employed protein and peptide enrichment methods such as immunopurification and affinity separation. Notably, apart from being laborious, these techniques introduce a bias into the peptide population and are thus not compatible with absolute quantification. Thus, existing approaches lack the capability of providing a comprehensive, quantitative analysis of tau modifications.

To address the critical need for a quantitative analytical method to measure tau PTMs, this disclosure provides an MS-based assay, the FLEXIQuant (Full-length expressed stable isotope-labeled protein for quantification) strategy. This assay allows for the unbiased analysis of tau modifications in a highly quantitative fashion, where the addition of a stable isotope labeled tau standard to the biological sample is key to the quantification. Using this standard, endogenous tau peptides (originating from the biological sample) can be quantified relative to their heavy standard cognate peptides. A change in relative abundance of unmodified peptide species directly reflects on the amount of endogenous PTM. One key advantage of this approach is that no prior knowledge of PTM type or isoforms are required.

To maximize reproducibility and sensitivity, this disclosure provides a selected reaction monitoring acquisition method (SRM) and developed a highly sensitive, robust, tau-specific assay, which is named as FLEXiTau. This assay was validated by employing it on an Sf9 expressed human tau used to study tau expression. This model generates tau in an exceptionally high phosphorylated state and tau extracted from these is predisposed to form oligomers.

The assays described in this disclosure can measure the precise phosphorylation state of hyperphosphorylated tau species, mapping and quantifying over 20 phosphorylations in a site-specific manner. To demonstrate the versatility of the assay further, the assay was also applied to tau aggregates derived from post-mortem AD brain tissue. It is determined that the performance of the assay is not compromised by the complexity of the human sample or the heterogeneity of the modifications on tau.

Thus, the present disclosure provides the first method to provide a comprehensive, global analysis of tau PTMs.

This disclosure also exploited a defining pathological hallmark of tauopathies, abnormal tau deposition, to identify and classify this group of neurodegenerative diseases. Based on reports of disease-specific modifications and reported differences in spliceform homeostasis, and the differences in glial and neuronal deposits, it is hypothesized that the molecular nature of tau may show disease specificity. The analyses using post-mortem cerebral cortex included patients with AD, CBD, PSP, and PiD, as well as control subjects. To identify the molecular signature in these diseases, this disclosure used a targeted FLEXITau SRM strategy to profile the peptide landscape of tau in 129 post-mortem brain samples. These data included identification and quantification of specific tau peptides that provided us with a unique molecular readout of tau across the tauopathies. In addition, this disclosure also identified the associated modifications, producing the most comprehensive PTM map of tau in diseased tissue to date. The FLEXITau data were then used to build and test a diagnostic classifier for each diagnostic group. A supervised RF machine learning method was trained on a well-characterized group of patients and subsequently tested on a highly heterogeneous, independent test set. Cases identified by more than one classifier and those that did not match the primary diagnosis in the pathology reports were evaluated by referencing pathology reports and clinical data, if available, and by personal correspondence with neuropathologists at each brain bank.

The disclosure also demonstrates that tau in different tauopathies carries a unique molecular signature that can be used to distinguish between the diseases. The discrimination between diseases is likely to be caused by a unique combination of isoform and PTM distribution characteristic for each condition. The use of MS in conjunction with a computational classifier provides a powerful tool for the classification of tauopathies and may enable future in vivo diagnostic and prognostic tools as well as therapeutic approaches.

The present disclosure also provides diagnostic classification using MS-based quantitative proteomics that employs specific patterns of proteins or peptides in body fluids or other tissues to uniquely define a disease state. MS is currently the most quantitative and specific tool for the measurement of proteins and thus offers enhanced diagnostic accuracy. In addition, MS-based proteomics can accommodate biological heterogeneity in disease expression, with successful applications to cancer diagnostics, alcoholism, schizophrenia, and several other diseases. Given the prevalent disease-specific modifications of tau, the variety of tau structures, as well as distinct isoform distributions found in sporadic tauopathies, a targeted quantitative MS-based assay to precisely and accurately is developed to measure this tau signature and the associated PTMs. Supervised machine learning approaches are then used to evaluate the data and determine if specific features could accurately classify the disease categories. The final classifier developed achieved excellent diagnostic accuracy of 95.9% for both CBD and ctrl, 93.9% for AD, and 91.8% for PiD. Good diagnostic accuracy was achieved for PSP with 81.6% accuracy, despite low pathological tau levels in the tissue examined. Most discriminating peptide features were located in the MT-binding region of tau, including exon 10 that is prone to alternative splicing leading to 3R and 4R isoforms. This quantitative and qualitative approach provides a molecular signature for each tauopathy that allows a healthcare professional to distinguish between the disorders. The use of an MS assay for the post-mortem diagnosis of tauopathies circumvents many of the issues associated with traditional histopathological assessments and could provide information for the most efficient use of diagnostic immunohistochemistry. The sensitivity of the SRM technique employed in the described methods allows for the detection of attomolar amounts of tau, thus requiring a minimal amount of tissue. The methods described in this disclosure is also relatively simple to implement, requiring heavy isotope labeled recombinant protein and a state-of-the-art mass spectrometer, and tens of samples can be analyzed in parallel. Coupled with the computational classifier, the described workflow provides a uniform diagnostic platform that is transferable across centers. Notably, the testing of a single cortical brain specimen (in contrast to multiple sections) proves to be sufficient to achieve accurate diagnosis in 92% of cases.

Tauopathies

Tauopathies represent a large group of proteopathies featuring aggregates of an altered form of the microtubule associated protein tau. The term "tauopathy" refers to tau-related disorders or conditions, e.g., Alzheimer's Disease (AD), Progressive Supranuclear Palsy (PSP), Corticobasal Degeneration (CBD), Pick's Disease (PiD), Argyrophilic grain disease (AGD), Frontotemporal dementia and Parkinsonism associated with chromosome 17 (FTDP-17), Parkinson's disease, stroke, traumatic brain injury, mild cognitive impairment and the like.

Alzheimer's disease (AD) is a kind of tauopathies. It is a chronic neurodegenerative disease. The most common early symptom is difficulty in remembering recent events (short-term memory loss). As the disease advances, symptoms can include problems with language, disorientation (including easily getting lost), mood swings, loss of motivation, not managing self-care, and behavioral issues.

Several non-AD tauopathies fall into the spectrum of frontotemporal lobar degeneration (FTLD) with tau-immunoreactive inclusions (FTLD-tau) and are characterized by selective atrophy of the frontal and temporal cortex, together with superficial neuronal loss and gliosis (Dickson D W, Kouri N, Murray M E, Josephs K A. Neuropathology of Frontotemporal Lobar Degeneration-Tau (FTLD-Tau). Journal of Molecular Neuroscience 2011; 45(3): 384-9; Seelaar H, Rohrer J D, Pijnenburg Y A L, Fox N C, van Swieten J C. Clinical, genetic and pathological heterogeneity of frontotemporal dementia: a review. Journal of neurology, neurosurgery, and psychiatry 2011; 82(5): 476-86). The most common forms of sporadic FTLD-tau are corticobasal degeneration (CBD), progressive supranuclear palsy (PSP) and Pick's disease (PiD) (Thal D R, von Arnim C A, Griffin W S, et al. Frontotemporal lobar degeneration FTLD-tau: preclinical lesions, vascular, and Alzheimer-related co-pathologies. J Neural Transm (Vienna) 2015; 122(7): 1007-18; Goedert M, Ghetti B, Spillantini M G. Frontotemporal dementia: implications for understanding Alzheimer disease. Cold Spring Harb Perspect Med 2012; 2(2): a006254). Corticobasal degeneration is a progressive neurological disorder characterized by nerve cell loss and atrophy (shrinkage) of multiple areas of the brain including the cerebral cortex and the basal ganglia. Progressive supranuclear palsy is a degenerative disease involving the gradual deterioration and death of specific volumes of the brain. In contrast, Pick's disease, is a rare neurodegenerative disease that causes progressive destruction of nerve cells in the brain. defining characteristic of the disease is build-up of tau proteins in neurons, accumulating into silver-staining, spherical aggregations known as "Pick bodies."

Argyrophilic grain disease (AGD) is another type of dementia. It is marked by the presence of abundant argyrophilic grains and coiled bodies on microscopic examination of brain tissue.

The pathway leading from soluble and monomeric to hyperphosphorylated, insoluble and filamentous tau protein is at the center of tauopathies. Usually, the first tau aggregates form in a few nerve cells in discrete brain areas. These become self propagating and spread to distant brain regions in a prion-like manner. In a clinical setting, the clinical syndromic diagnosis is often determined by the patient's symptoms and deficits, while the pathological diagnosis is defined by characteristic types and distribution of the tau inclusions and of neuron loss.

Subjects

The terms "subject" and "patient" are used interchangeably throughout the specification and describe an animal, human or non-human, to whom treatment according to the methods of the present invention is provided. Human patients can be adult humans or juvenile humans. In some embodiments, humans can have an age of above 10, 20, 30, 35, 40, 45, 50, 55, 60, 65, 70, 75, 80, 85, or 90 years old. In some embodiments, the subject is a mammal. In some embodiments, the term "subject", as used herein, refers to a human (e.g., a man, a woman, or a child).

The subject can be symptomatic (e.g., the subject presents symptoms associated with tauopanthies (e.g., AD, AGD, CBD, PiD, PSP), such as, for example changes in personality, behavior, sleep patterns, and executive function, memory loss, confusion, inability to learn new things, difficulty carrying out multistep tasks, problems coping with new situations, hallucinations, delusions, and paranoia, impulsive behavior, inability to communicate, weight loss, seizures, skin infections, difficulty swallowing, groaning, moaning, grunting, increased sleeping, lack of control of bowel and bladder, disorders of word finding, disorders of reading and writing, disorientation, supranuclear palsy, a wide-eyed appearance, difficulty in swallowing, unwarranted anxiety, irrational fears, oniomania, impaired regulation of social conduct (e.g., breaches of etiquette, vulgar language, tactlessness, disinhibition, misperception), passivity, low motivation (aboulia), inertia, over-activity, pacing and wandering, etc. The subject can be asymptomatic (e.g., the subject does not present symptoms associated with a tauopathy, or the symptoms have not been recognized).

In addition to humans, subjects include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

Sample Collection and Preparation

Samples for use in the methods described herein include various types of samples from a subject.

In some embodiments, the sample is a "biologic sample". As used herein, the term "biological sample" or "sample" refers to a sample obtained or derived from a subject. By way of example, the sample may be selected from the group consisting of body fluids, blood, whole blood, plasma, serum, mucus secretions, urine or saliva. In some embodiments the sample is, or comprises a blood sample. The preferred biological source for detection of the biomarkers is a blood sample, a serum sample or a plasma sample. In some embodiments, the sample is cerebrospinal fluid (CSF) or a brain tissue.

As used herein, "obtain" or "obtaining" can be any means whereby one comes into possession of the sample by "direct" or "indirect" means. Directly obtaining a sample means performing a process (e.g., performing a physical method such as extraction) to obtain the sample. Indirectly obtaining a sample refers to receiving the sample from another party or source (e.g., a third party laboratory that directly acquired the sample). Directly obtaining a sample includes performing a process that includes a physical change in a physical substance, e.g., a starting material, such as a blood, e.g., blood that was previously isolated from a patient. Thus, obtain is used to mean collection and/or removal of the sample from the subject. Furthermore, "obtain" is also used to mean where one receives the sample from another who was in possession of the sample previously.

In some embodiments, a reference sample is obtained from at least one individual not suffering from a tauopathy. In some other embodiments, the reference sample is obtained from at least one individual previously diagnosed as having a tauopathy (e.g., AD, AGD, CBD, PiD, PSP). In some embodiments, the reference sample comprises a predetermined, statistically significant reference analyte levels.

In some embodiments, the sample is collected from the brain of a subject, e.g., brain tissue. In some embodiments, the sample is collected from cerebrospinal fluid or plasma.

In some embodiments, the sample is collected from a biopsy. A biopsy is a sample of tissue taken from the body of a living subject. A biopsy sometimes also refers to the medical procedure that removes tissue from a living subject. In some embodiments, the sample can be collected through a punch biopsy. A punch biopsy is done with a circular blade ranging in size from 1 mm to 8 mm. In some embodiments, the sample can be collected from fine-needle aspiration biopsy (FNAB or FNA). Fine-needle aspiration biopsy is a procedure used to investigate superficial (just under the skin) lumps or masses. In some embodiments, a thin, hollow needle is inserted into the body to collect samples.

In some embodiments, the sample is from a live subject. For example, the sample can be collected from a subject during a medical procedure, e.g., a surgery.

In some embodiments, samples are collected from postmortem specimens, e.g., human post-mortem brain specimens.

In some embodiments, brain tissue can be obtained from Brodmann area 39 (BA39) angular gyrus brain blocks.

In some embodiments, biopsy samples are homogenized and clarified by centrifugation. Supernatants containing tau proteins are pooled and used as a crude tau fraction (unfractionated homogenate).

In some embodiments, samples are collected from cultured cells, e.g., from *E. coli* or sf9 cells. In some embodiments, samples are collected from the brain tissue of model animals.

Full-Length Expressed Stable Isotope-Labeled Tau (FLEXiTau)

In some aspects, the disclosure provides methods for determining post-translational modifications and/or quantifying the amount of post-translational modifications disclosed herein utilizes a stable isotope-labeled ('heavy') full-length tau protein standard that is added to a biological specimen prior to sample processing and MS analysis, which is referred to herein as "FLEXiTau".

The heavy tau standard can generated by various means. In some embodiments, the longest tau isoform (4R2N) is cloned into the various vectors, e.g., FLEX-vector, introducing an N-terminal artificial tag to the protein that is later used for standard purification as well as for absolute quantification of the endogenous tau. The FLEX-vector is described in, e.g., Singh, Sasha, et al. "FLEXIQuant: a novel tool for the absolute quantification of proteins, and the simultaneous identification and quantification of potentially modified peptides." Journal of proteome research 8.5 (2009): 2201-2210, which is incorporated by reference in its entirety.

In some embodiments, heavy tau protein can be expressed in a cell free expression system in the presence of isotopically labeled aspartic acid, lysine and arginine. The triple labeling strategy can minimize co-expressed light tau standard that could lead to a bias in quantification of endogenous tau.

The tau standard is purified and is added to unlabeled endogenous sample ('light') in a predetermined ratio. Various ratios can be used, e.g., approx. 4:1, 3:1, 2:1, 1:1, 1:2, 1:3 or 1:4. The protein mix is subjected to enzymatic digest and LC-MS analysis. Notably, due to the mixing of light and heavy species early in the sample processing, quantification errors that might arise due to sample loss and technical variability of sample preparation are minimized. The protein mix can be digested by various enzymes, e.g., trypsin, Lys-C, Arg-C, Asp-N, Glu-C, Lys-N, thermolysin, elastase, and chymotrypsin. In some embodiments, the labeled sample and the unlabeled sample is subjected to enzymatic digest separately before they are mixed together.

All unmodified tau peptides will be present as pairs, featuring the light (unlabeled) and the heavy (labeled) isotopologue. While each pair of peptide species has varying signal intensities, the light-to-heavy (L/H) intensity ratio of all unmodified peptides reflects the initial mixing ratio (e.g., L/H=1). The phosphorylation causes a mass shift, reducing the amount of detectable unmodified peptide. In consequence, a deviation of the mixing ratio is observed. The extent of modification on that peptide can be inferred by the amount of 'missing' unmodified species.

Plotting the L/H ratio of all peptides sorted from N- to C terminal results in an intuitive representation of the PTM landscape across tau protein, where individual modifications as well as modified peptide regions can be quantitatively inferred.

Figure 1A:
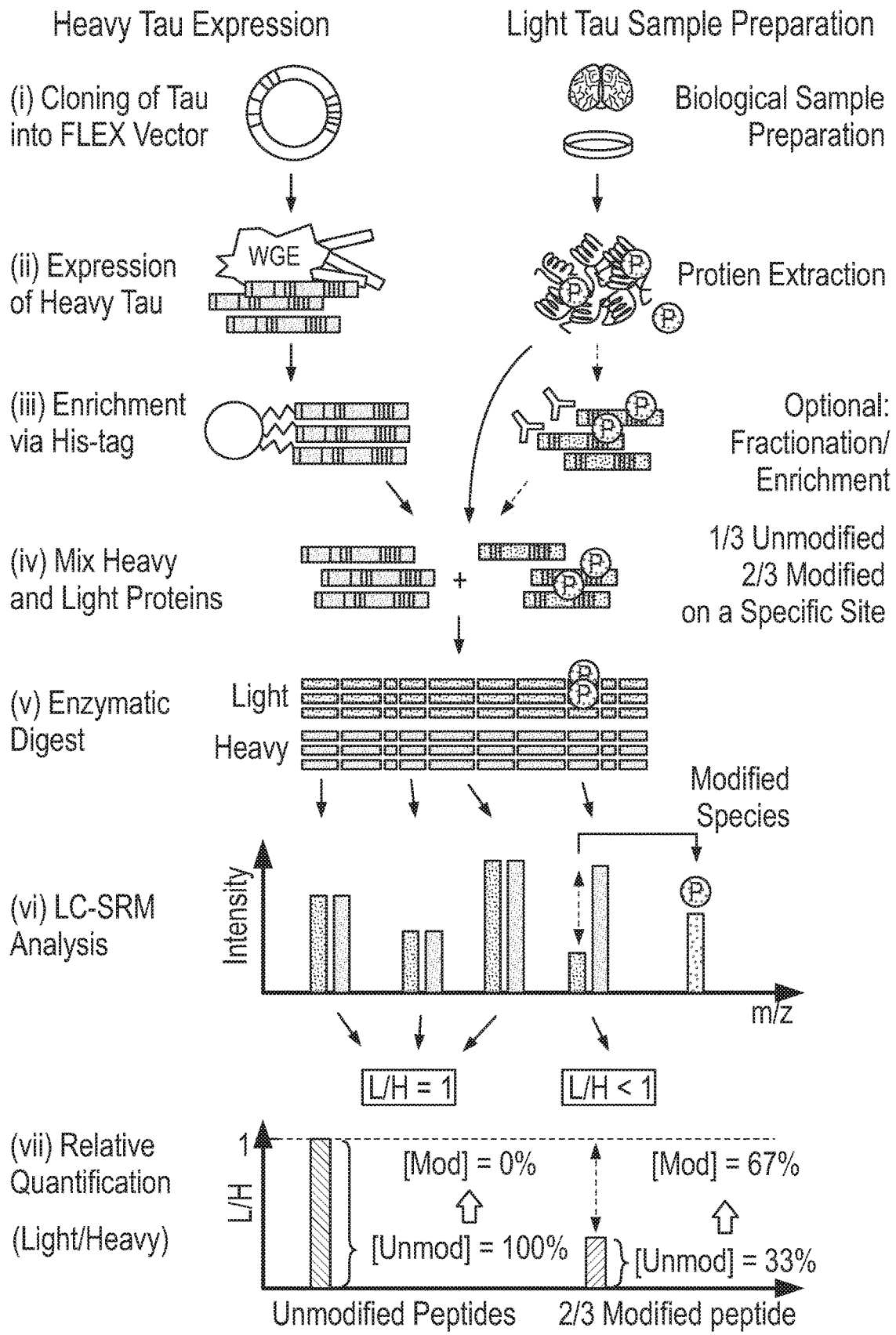
FIGS. 1A-1C are schematic diagrams showing one exemplary workflow of quantifying the amount of post-translational modifications.
Figure 1B:
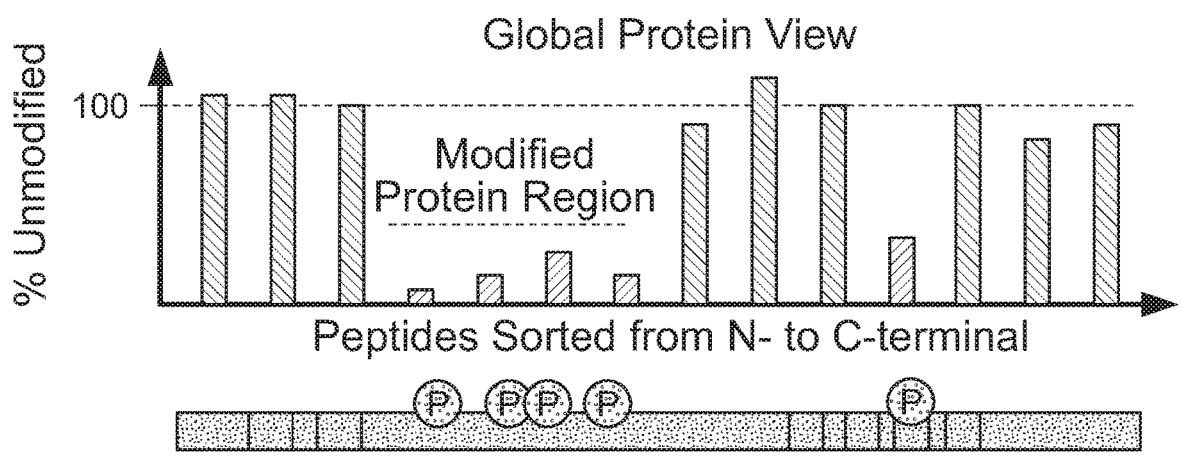
Figure 1C:
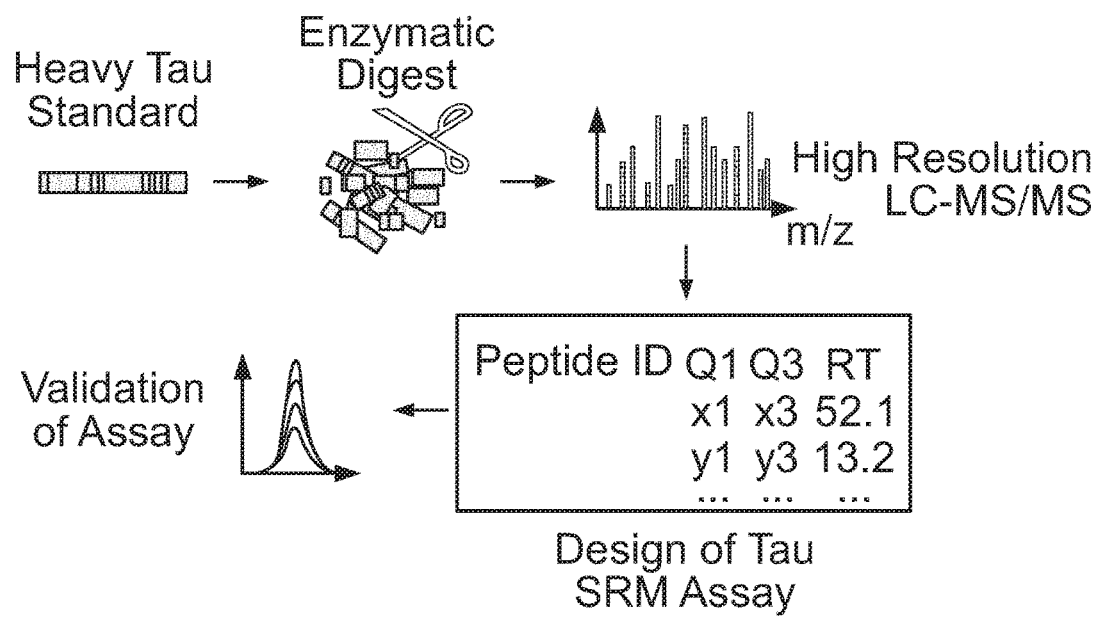

One exemplary workflow is shown in FIGS. 1A-1C. Referring to FIG. 1A, the heavy tau standard is generated using the FLEX vector in the presence of heavily labeled amino acids.

After purification, it is added to unlabeled endogenous sample in a ratio of approx. 1:1. A mix of three species of heavy tau standard and 3 species of endogenous tau proteins is assumed. ⅔ of the endogenous species are phosphorylated on a specific site. The protein mix is subjected to enzymatic digest and Liquid chromatography-mass spectrometry (LC-MS) analysis. All unmodified tau peptides will be present as pairs, featuring the light and the heavy isotopologue. While each pair of peptide species has varying signal intensities, the light-to-heavy (L/H) intensity ratio of all unmodified peptides reflects the initial mixing ratio (here, L/H=1 as an example). The phosphorylation causes a mass shift, reducing the amount of detectable unmodified peptide. In consequence, a deviation of the mixing ratio is observed (here, L/H=0.33 as an example). The extent of modification on that peptide can be inferred by the amount of 'missing' unmodified species (here, [Mod]=0.67 as an example). Referring to FIG. 1B, plotting of peptide L/H ratios sorted from protein N- to C-terminus allows for a global visualization of modified peptides and protein regions. In FIG. 1C, for the development of the tau SRM assay, an enzymatic digest of His-tag purified heavy tau is analyzed by high resolution LC-MS/MS and used to generate a transition list. FIG. 1D shows sequence coverage of quantifiable tau peptides by SRM is shown in bold black (tau sequence of human 4R2N). Additional coverage using LysC is also shown in FIG. 1D.

Isotope-Labeled Samples

An exemplary method for preparing isotope-labeled ('heavy') tau proteins (e.g., Tau isoform 4R2N, GI: 294862262) comprise cloning the tau gene into a vector, and expressing the protein with isotopically labeled amino acids.

In some embodiments, expression of human Tau proteins can be carried out in bacteria or yeast expression system, e.g., from *E. coli* cells. In some embodiments, it can be translated in a cell-free expression system, e.g., wheat germ expression (WGE) system (Cell Free Sciences, Wheat Germ Expression H Kit-NA).

Expression can be carried out in the presence of one or more isotope labeled amino acids. Isotope labeled amino acids include, but are not limited to, e.g., lysine (13C6 15N2), arginine (13C6 15N4) and asparagine (13C4 15N1), etc.

In some embodiments, the isotopes for the isotopically labeled amino acids include $^2H$, $^{13}C$, $^{14}C$, $^{15}N$ and $^{33}P$, etc. Thus, the labeled amino acid residues are "heavier" as compared to unlabeled amino acid residues. However, other isotopes can be used, for example, some isotopes with less atomic mass. In those cases, the labeled amino residues will be "lighter" as compared to unlabeled amino acids.

Tau proteins can be purified by various means. In some embodiments, human Tau proteins can be purified by chromatography, e.g., cation exchange chromatography and/or size exclusion chromatography. In some embodiments, Ni-Sepharose beads are used to purify heavy tau standard. Briefly, after a prewash in binding buffer, beads are incubated with samples. After removal of the unbound fraction, beads are washed with wash buffer, followed by elution of tau.

Selected Reaction Monitoring (SRM) and Parallel Reaction Monitoring (PRM)

The quality of the FLEXiTau data strongly depends on the sensitive and reproducible MS-based detection of the unmodified peptide species. To ensure this, in some embodiments, a targeted assay specifically tailored to monitor the unmodified tau using SRM is devised.

SRM is a mass spectrometry technique for the detection and quantification of specific, predetermined analytes with known fragmentation properties in complex backgrounds. SRM is used for precise quantification of targeted proteins (Kuhn 2014, Picotti 2009, Anderson 2006). It was originally used for the quantification of small molecules (such as metabolites or drugs (Zweigenbaum 2000). SRM is used most effectively in a liquid chromatography-coupled mass spectrometry (LC-MS) system, where a capillary chromatography column is connected in-line to the electrospray ionization source of the mass spectrometer. SRM exploits the unique capability of triple quadrupole (QQQ) (Yost 1979, Yost 1978) mass spectrometers to act as mass filters and to selectively monitor a specific analyte molecular ion and one or several fragment ions generated from the analyte by collisional dissociation (Yost 1979, Yost 1978, Kondrat 1978). The number of such fragment ions that reach the detector is counted over time, resulting in a chromatographic trace with retention time and signal intensity as coordinates. Several such precursor-fragment ion pairs, termed SRM transitions, can be sequentially and repeatedly measured at a periodicity that is fast compared to the analyte's chromatographic elution, yielding chromatographic peaks for each transition that allow for the concurrent quantification of multiple analytes. When multiplexing SRMs the assay is termed as a multiple reaction monitoring (MRM) assay, which is frequently used as a synonym of SRM. Parallel reaction monitoring (PRM) is the application of SRM with parallel detection of all transitions in a single analysis—this assay has recently been facilitated by the development of a high resolution mass spectrometers.

When applied to proteomics, SRM measures peptides produced by the enzymatic digestion of a proteome as surrogates of the corresponding proteins. Molecular ions within a mass range centered around the mass of the targeted peptide are selected in the first mass analyzer (Q1), fragmented at the peptide bonds by collision-activated dissociation (in Q2) and one or several of the fragment ions uniquely derived from the targeted peptide are measured by the second analyzer (Q3) (Kuhn 2014, Lange 2008). Integration of the chromatographic peaks for each transition supports the relative or, if suitable heavy isotope-labeled reference standards are used, absolute quantification of the targeted peptide(s) initially released from the protein and loaded on the LC-MS system. A suitably chosen set of SRM transitions therefore constitutes a specific assay to detect and quantify a target peptide and, by inference, a target protein in complex samples.

A crucial step in developing SRM assays is the identification of the most sensitive and selective transitions (pair of peptide and their fragment ion masses). A spectral library is created in order to find suitable transitions. To this end, high-resolution liquid chromatography tandem mass spectrometry (LC-MS/MS) of purified, digested tau standard is performed and it generates a collection of experimentally detected peptides and their fragment ions (FIG. 1C).

The spectral library is then used to develop a quantitative SRM assay for these peptides, choosing the transitions with highest intensity without interfering signals. The sensitivity of the SRM method can be maximized by acquisition of the transitions in a small retention time window (termed scheduled SRM). Therefore, in some embodiments, a scheduled 30 min LC-SRM method is developed. This method is suitable for pure/low complex tau samples and enables tau modification profile quantification from pure/low complex tau samples in a sensitive and time efficient manner. Methods of implementing SRM is described in various articles, e.g., Lange, Vinzenz; Picotti, Paola; Domon, Bruno; Aebersold, Ruedi (2008). "Selected reaction monitoring for quantitative proteomics: a tutorial". Molecular Systems Biology. 4; Picotti, Paola, and Ruedi Aebersold. "Selected reaction monitoring-based proteomics: workflows, potential, pitfalls and future directions." Nature methods 9.6 (2012): 555-566.

In some embodiments, parallel reaction monitoring is used to monitor the amount of modified and unmodified tau peptide fragments. Parallel reaction monitoring (PRM) is the application of SRM with parallel detection of all transitions in a single analysis using a high resolution mass spectrometer. Methods of implementing Parallel reaction monitoring is described in various articles, e.g., in Peterson, A. C.; Russell, J. D.; Bailey, D. J.; Westphall, M. S.; Coon, J. J. (2012). "Parallel Reaction Monitoring for High Resolution and High Mass Accuracy Quantitative, Targeted Proteomics". Molecular & Cellular Proteomics. 11 (11): 1475-1488.

Data-Independent Acquisition

While the use of SRM ensures optimum sensitivity, accuracy and precision, the analytes of interest have to be defined upfront because only those analytes are monitored with SRM. Mining data for other analytes, defined at a later point as being of interest, is not possible.

To provide such flexibility of mining data post hoc for analytes of interest, the present disclosure provides a totally unbiased mass spectrometric method to monitor all detectable tau-derived peptides using Data Independent Acquisition (DIA); also called "Sequential Window Acquisition of all Theoretical Mass Spectra" or SWATH) routines.

DIA is a mass spectrometry technique for the unbiased identification and quantification of all detectable analytes. In DIA, the first quandrupole is stepped through the entire m/z-range, selecting ranges of e.g. 25 m/z-units (400 to 425, 425 to 450, 450 to 475, etc.). In some embodiments of DIA, the individual m/z steps are adjusted in width according to the complexity within a given m/z range, so that every m/z step features a similar number of precursors. The relevant methods are described in, e.g., Gillet, Ludovic C., et al. "Targeted data extraction of the MS/MS spectra generated by data-independent acquisition: a new concept for consistent and accurate proteome analysis." Molecular & Cellular Proteomics 11.6 (2012): 0111-016717; Law, Kai Pong, and Yoon Pin Lim. "Recent advances in mass spectrometry: data independent analysis and hyper reaction monitoring." Expert review of proteomics 10.6 (2013): 551-566; Rosenberger, George, et al. "A repository of assays to quantify 10,000 human proteins by SWATH-MS." Scientific data 1 (2014); Sidoli, Simone, et al. "Sequential Window Acquisition of all Theoretical Mass Spectra (SWATH) Analysis for characterization and quantification of histone post-translational modifications." Molecular & Cellular Proteomics 14.9 (2015): 2420-2428; Chang, Rachel Yoon Kyung, et al. "SWATH analysis of the synaptic proteome in Alzheimer's disease." Neurochemistry international 87 (2015): 1-12; Zhang, Ying, et al. "The Use of Variable Q1 Isolation Windows Improves Selectivity in LC-SWATH-MS Acquisition." Journal of proteome research 14.10 (2015): 4359-4371; Aebersold, Ruedi, et al. "Applications and Developments in Targeted Proteomics: From SRM to DIA/SWATH." Proteomics 16.15-16 (2016): 2065-2067; each of which is incorporated by reference in its entirety.

All precursors eluting at that moment off the liquid chromatography column within the selected m/z range are simultaneously fragmented and the fragment ions are detected in the second, the high resolution/high accuracy mass analyzer, i.e. Orbitrap or time-of-flight mass analyzer. Based on the elution profiles, the connectivity between the precursors and fragment ions are established. For the subsequent of the detected and fragmented peptides, spectral libraries are used, i.e. spectra for the analytes of interest have to be available in order to identify them. However, this also means if new analytes are identified as being of interest, the data can be re-interrogated with a new spectral library featuring also the spectrum of the novel analyte.

When analyzing samples by DIA, the quantification of the unmodified Tau-derived peptides (endogenous as well as exogenous, i.e. heavy isotope labeled peptides) are easily, accurately and precisely identified and quantified. Simultaneously, all detectable modified Tau-derived peptides are analyzed and fragmented so that they can be identified once an appropriate example fragment ion spectrum is obtained that can be used for the spectral library. Sophisticated quantification algorithms as provided by programs such as Skyline, Spectronaut, or OpenSWATH allows the subsequent quantification of the modified peptides. These quantification algorithms and the methods to use mass spectrometry are described in numerous articles, e.g., MacLean, Brendan, et al. "Skyline: an open source document editor for creating and analyzing targeted proteomics experiments." Bioinformatics 26.7 (2010): 966-968; Schilling, Birgit, et al. "Platform-independent and label-free quantitation of proteomic data using MS1 extracted ion chromatograms in Skyline application to protein acetylation and phosphorylation." Molecular & cellular proteomics 11.5 (2012): 202-214; Schubert, Olga T., et al. "Building high-quality assay libraries for targeted analysis of SWATH MS data." Nature protocols 10.3 (2015): 426-441; Rardin, Matthew J., et al. "MS1 peptide ion intensity chromatograms in MS2 (SWATH) data independent acquisitions. Improving post acquisition analysis of proteomic experiments." Molecular & Cellular Proteomics 14.9 (2015): 2405-2419; Bruderer, Roland, et al. "Extending the limits of quantitative proteome profiling with data-independent acquisition and application to acetaminophen-treated three-dimensional liver microtissues." Molecular & Cellular Proteomics 14.5 (2015): 1400-1410; Bruderer, Roland, et al. "High-precision iRT prediction in the targeted analysis of data-independent acquisition and its impact on identification and quantitation"; Röst, Hannes L., et al. "OpenSWATH enables automated, targeted analysis of data-independent acquisition MS data." Nature biotechnology 32.3 (2014): 219-223; each of which is incorporated by reference in its entirety.

Calculation of Site-Occupancy

Figure 4A:
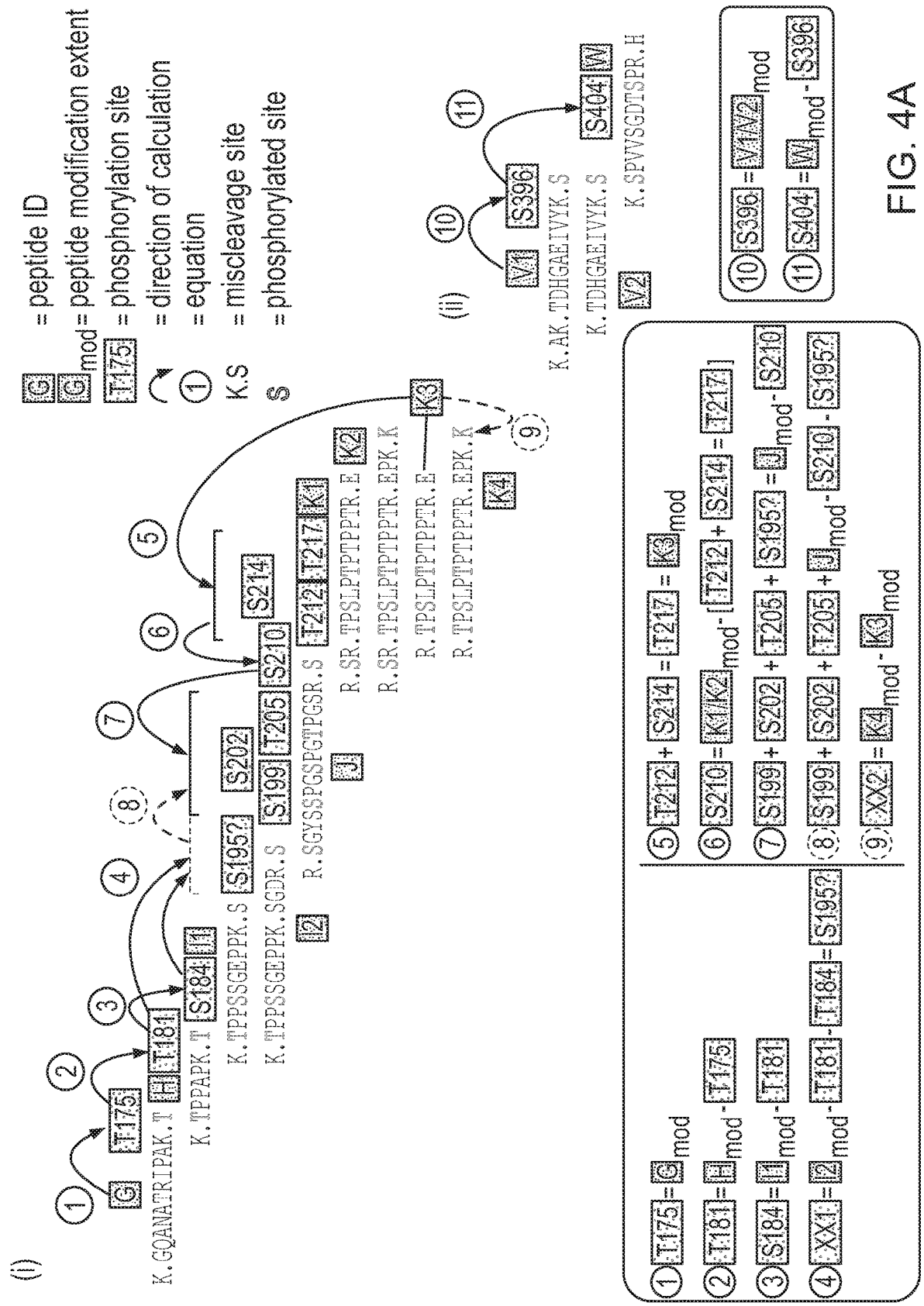
FIG. 4A is a schematic diagram showing one exemplary approach to calculate individual site occupancies by using quantitative information from overlapping peptides.

Individual site occupancies of the mapped phosphorylation sites can be calculated using the equations listed in FIG. 4A, for each biological replicate separately. The sum of site occupancies of all modifications is used to infer the number of phosphates per tau molecule.

A recursive approach can be used to calculate the polynomial probability distribution of observing a specific number of phosphorylations per tau molecule. The input data consisted of site occupancies $X_{ij}$ for the total number of sites for each biological replicate. The probability $p_j$ of a site j (j=1, 2, . . . , N) being modified from a total of r=3 replicates (i=1, 2, 3) was calculated as $$p_j = \frac{1}{r}\sum_{i=1}^{r} X_{ij}$$

Given D={$p_1, p_2, \ldots, p_N$} the entire list of probability values for all N sites, $P(1|p_m)=p_m$ the probability of observing site m in a particular tau species, and $P(0|p_m)=1-p_m$, the probability of not observing site m, the probability of seeing k sites to be modified in that particular species out of all N sites was calculated as $$P(k|D)=p_1(k-1|D-p_1)+(1-p_1)*P(k|D-p_1)$$

With $P(0|D)=\Pi_{i=1}^{17}(1-Pi)$ being the probability of observing 0 sites.

Classifiers

Classifiers are generated via a data processing system by applying one or more mathematical models to a dataset. In some embodiments, a classifier for each patient group is developed. For example, a classifier can be developed for Alzheimer's disease (AD), Argyrophilic grain disease (AGD), Corticobasal degeneration (CBD), Pick's disease (PiD) and Progressive supranuclear palsy (PSP).

In some embodiments, the input data include normalized L/H peptide intensity ratios of peptide. In some embodiments, a sample can be represented by the intensity ratios of 1, 2, 3, 4, 5, 6, 7, 8, 9, 10, 11, 12, 13, 14, 15, 16, 17, 18, 19, 20, or more than 20 peptides (features). In some embodiments, a sample is represented by a vector of 17 peptides (features). In some embodiments, the vector can include the absolute abundance.

In some embodiments, tau peptide fragments are selected from the group consisting of (QEFEVMEDHAGTYGLGDR), SEQ ID NO: 1

(DQGGYTMHQDQEGDTDAGLK), SEQ ID NO: 2

(ESPLQTPTEDGSEEPGSETSDAK), SEQ ID NO: 3

(STPTAEDVTAPLVDEGAPGK), SEQ ID NO: 4

(QAAAQPHTEIPEGTTAEEAGIGDTPSLEDEAAGHVTQAR), SEQ ID NO: 5

(TPPSSGEPPK), SEQ ID NO: 6

(SGYSSPGSPGTPGSR), SEQ ID NO: 7

(TPSLPTPPTR), SEQ ID NO: 8

(TPSLPTPPTREPK), SEQ ID NO: 9

(LQTAPVPMPDLK), SEQ ID NO: 10

(KLDLSNVQSK), SEQ ID NO: 11

(LDLSNVQSK), SEQ ID NO: 12

(HVPGGGSVQIVYKPVDLSK), SEQ ID NO: 13

(IGSLDNITHVPGGGNK), SEQ ID NO: 14

(TDHGAEIVYK), SEQ ID NO: 15

(SPVVSGDTSPR), SEQ ID NO: 16
and (HLSNVSSTGSIDMVDSPQLATLADEVSAVSASSLAK). SEQ ID NO: 17

In some embodiments, the computational classifier is designed for each disease category. In some embodiments, a binary dataset is created including the case category of interest and the reference category. In some embodiments, the reference category includes ubjects who do not have the disease of interest. In some embodiments, the reference category include subjects who do not have any tauopathies (e.g., all subjects in the reference category do not have a tauopathy). For example, a case category of interest can include all subjects have AD, and the reference category can include all non-AD subjects. In some other embodiments, the reference category only includes control subjects (subjects without tauopathies).

Mathematical models useful in accordance with the disclosure include those using both supervised and unsupervised learning techniques. In one embodiment, the mathematical model chosen uses supervised learning in conjunction with a training population to evaluate each possible combination of variables. Various mathematical models can be used, for example, a regression model, a logistic regression model, a neural network, a clustering model, principal component analysis, correlated component analysis, nearest neighbor classifier analysis, linear discriminant analysis, quadratic discriminant analysis, a support vector machine, a decision tree, a genetic algorithm, classifier optimization using bagging, classifier optimization using boosting, classifier optimization using the Random Subspace Method, a projection pursuit, and genetic programming and weighted voting, etc. In some embodiments, the classifier involves a supervised machine learning model.

Many machine learning methods are available for supervised machine learning classifiers. These methods include, but are not limited to, Random forest (RF), Neural networks (Nnet), k-nearest neighbor (KNN), Learning Vector Quantization (LVQ), Linear Discriminant Analysis (LDA), and Support Vector Machines (SVM), etc. These algorithms are known in the art, and are described in various literature, e.g., Leo Breiman J F, Charles J. Stone, R. A. Olshens, J. Classification and Regression Trees. Wadsworth Statistics/Probability 1984; Bishop C M. Neural Networks for Pattern Recognition: Oxford: Oxford University Press; 1995; Altman N S. An Introduction to Kernel and Nearest-Neighbor Nonparametric Regression. The American Statistician 1992; 46(3): 175-85; Kohonen T. Learning vector quantization: MIT Press; 1995; Fisher R A. THE USE OF MULTIPLE MEASUREMENTS IN TAXONOMIC PROBLEMS. Ann Eugen 1936; 7(2): 179-88; Cortes C, Vapnik V. Support-Vector Networks. Machine Learning 1995; 20(3): 273-97).

In some embodiments, a recursive feature elimination method based on the Random Forest (RF) algorithm is used to select the feature set that provides optimal separation of the case category and reference category in the training dataset.

Classifier can be evaluated using an independent testing dataset. This approach can be repeated for each case category, i.e. also PSP, PiD, CBD, and ctrl. The performance of the classifiers is assessed by accuracy (ac), defined as the total number of correctly classified cases (True Positives, TP, and True Negatives, TN) relative to the total number of cases in the testing set. Sensitivity (se) of the classifier is calculated as the number of TP divided by the total number of cases with given condition, that is TP and False Negatives (FN) (se=TP/(TP+FN)). Specificity is determined as the proportion of TN to the number of cases without given condition, that is TN plus False Positives (FP) (sp=TN/(TN+FP)). The performance (the positive diagnostic likelihood ratio) of a classifier, expressed by its true positive rate (TPR, or sensitivity), and false positive rate (FPR, or 1−specificity), is plotted in a receiver operator curve (ROC) space. The predictive power of each classifier can be further assessed by calculating the area under the ROC curve (AUC; AUC: 0.9-1.0=excellent; 0.8-0.9=good; 0.7-0.8=fair; 0.6-

0.7=poor; 0.5-0.6=fail). Description of various statistics to evaluate the performance of the classifier can be found, e.g., in Sing T, Sander O, Beerenwinkel N, Lengauer T. ROCR: visualizing classifier performance in R. Bioinformatics 2005; 21(20): 3940-1. A perfect ROC area score of 1.0 is indicative of both 100% sensitivity and 100% specificity.

In some embodiments, classifiers are selected on the basis of the evaluation score. In some embodiments, the evaluation scoring system used is a receiver operating characteristic (ROC) curve score determined by the area under the ROC curve. In some embodiments, classifiers with scores of greater than 0.95, 0.9, 0.85, 0.8, 0.7, 0.65, 0.6, 0.55, or 0.5 are chosen. In some embodiments, where specificity is important to the use of the classifier, a sensitivity threshold can be set, and classifiers ranked on the basis of the specificity are chosen. For example, classifiers with a cutoff for specificity of greater than 0.95, 0.9, 0.85, 0.8, 0.7, 0.65, 0.6, 0.55, 0.5 or 0.45 can be chosen. Similarly, the specificity threshold can be set, and classifiers ranked on the basis of sensitivity (e.g., greater than 0.95, 0.9, 0.85, 0.8, 0.7, 0.65, 0.6, 0.55, 0.5 or 0.45) can be chosen. Thus, in some embodiments, only the top ten ranking classifiers, the top twenty ranking classifiers, or the top one hundred ranking classifiers are selected. The ROC curve can be calculated by various statistical tools, e.g., Statistical Analysis System (SAS®), and R (a language and environment for statistical computing and graphics).

A supervised classifier can be computed for patient categories of interest. In some embodiments, for the training of a classifier for a certain disease category a binary approach is used whereby the case category (for example AD) is classified against the remaining 'mixed' reference category (including all non-AD samples, e.g. CBD, PSP, PiD and ctrl). In some embodiments, the training process is repeated several times, for example, 5, 10, 15, 20, 50 times, i.e. each time a different subset of the reference category is randomly selected in order to obtain a stable classifier.

Generally, the training data set includes data obtained from a training population (e.g., a group of individuals whose diagnoses are determined). As described above, a data processing system applies a mathematical model to a training dataset and generates and trains a classifier. The classifier is the resultant mathematical model including the values for various parameters of the mathematical model. In turn, a data processing system applies one or more of these generated classifiers to a testing dataset for one or more test subjects to determine whether the test subject(s) have, or likely to have any tauopathies, e.g., Alzheimer's disease (AD), Argyrophilic grain disease (AGD), Corticobasal degeneration (CBD), Pick's disease (PiD) and Progressive supranuclear palsy (PSP).

Classifiers can be used alone or in combination with each other to create a formula for determining whether a subject has any tauopathies. One or more selected classifiers can be used to generate a formula. It is not necessary that the method used to generate the data for creating the formulas be the same method used to generate data from the test subject.

In some embodiments, the individuals of the training dataset used to derive the model or the classifier are different from the individuals of a population used to test the model or the classifier. As would be understood by a person skilled in the art, this allows a person skilled in the art to characterize an individual whose phenotypic trait characterization is unknown, for example, to determine the disease status of a subject, or the likelihood that an induvial have a disease.

Applying a mathematical model to the data will generate one or more classifiers. In some embodiments, multiple classifiers are created that are satisfactory for the given purpose (e.g., all have sufficient AUC and/or sensitivity and/or specificity). In some embodiments, a formula is generated that utilizes more than one classifier. For example, a formula can be generated that utilizes classifiers in series. Other possible combinations and weightings of classifiers would be understood and are encompassed herein.

Diagnostics

The methods described in this disclosure can be used for diagnosis, including in vivo and in vitro diagnostic tools. In some embodiments, the development of tau-based biomarkers in cerebrospinal fluid (CSF), plasma or brain biopsy tissue can be used for clinical diagnostics.

In some embodiments, the subject is suspected of having a tauopathy, e.g., Alzheimer's disease, progressive supranuclear palsy, corticobasal degeneration, Pick's disease. A sample containing tau proteins is collected from the subject. The extent of post translational modification is determined by the methods as described in the present disclosure, and a dataset is generated. A dataset can have one or more data records. A classifier is applied to the dataset to determine whether the subject has a tauopathy, or the likelihood that the subject has a tauopathy.

Table 14 lists fractions of unmodified peptides for different tauopathies. In some embodiments, the amount of PTMs of peptide for these peptide fragments from can be used in a classifier to determine whether a test subject having a tauopathy, the method includes the steps of inputting, into a classifier, data representing the amount of post translational modifications (PTMs) for a set of tau protein peptide fragments from a test subject, wherein the classifier being for determining whether the amount of PTMs for the set of tau protein peptide fragments classifies with (A) a set of data repressing the amount of PTMs for the set of tau protein peptide fragments from a first group of individuals who have the tauopathy; as opposed to classifying with (B) a set of data repressing the amount of PTMs for the set of tau protein peptide fragments from a second group of individuals who does not have the tauopathy; applying, by the one or more data processing devices, the classifier to the data representing the amount of PTMs for the set of tau protein peptide fragments from the test subject; and determining whether the test subject is classified with the first group of individuals who have the tauopathy or the second group of individuals who do not have the tauopathy.

In some embodiments, evaluating a subject for having a tauopathy involves determining whether determine whether the level of tau PTM associated with tau peptide fragments in a sample from the test subject is are significantly altered relative to the level for each tau peptide fragment in a reference group. In some embodiments, the reference group is a control group (e.g., a group of subjects who do not have tauopathies). In some embodiments, the reference group includes all subjects who does not have the tauopathy of interest (e.g., AD), and these subjects may have some other diseases (e.g., PSP).

In some embodiments, the tauopathy is AD, and the set of the tau peptide fragments comprises one or more tau peptide fragments selected from the group of SEQ ID NO: 8, SEQ ID NO: 10, SEQ ID NO: 11, SEQ ID NO: 13, SEQ ID NO: 14, and SEQ ID NO: 17. In some embodiments, the set of the tau peptide fragments comprises SEQ ID NO: 8 and/or SEQ ID NO: 17.

In some embodiments, the tauopathy is CBD, and the set of the tau peptide fragments comprises one or more tau peptide fragments selected from the group of SEQ ID NO: 4, SEQ ID NO: 11, SEQ ID NO: 12, SEQ ID NO: 13, SEQ ID NO: 14, and SEQ ID NO: 15. In some embodiments, the set of the tau peptide fragments comprises SEQ ID NO: 4.

In some embodiments, the tauopathy is PiD, and the set of the tau peptide fragments comprises one or more tau peptide fragments selected from the group of SEQ ID NO: 1, SEQ ID NO: 10, SEQ ID NO: 12, SEQ ID NO: 13, SEQ ID NO: 14, and SEQ ID NO: 17. In some embodiments, the set of the tau peptide fragments comprises SEQ ID NO: 13.

In some embodiments, the tauopathy is PSP, and the set of the tau peptide fragments comprises one or more tau peptide fragments selected from the group of SEQ ID NO: 3, SEQ ID NO: 7, SEQ ID NO: 8, SEQ ID NO: 11, SEQ ID NO: 12, and SEQ ID NO: 15. In some embodiments, the set of the tau peptide fragments comprises SEQ ID NO: 3.

In some embodiments, the methods described in the present disclosure can be used for post-mortem classification of tissues and re-evaluation. In some embodiments, these samples are from brain banks.

In one aspect, the disclosure provides a computer-implemented method for determining whether a test subject has a tauopathy. In one embodiment, the method comprises, inputting, into a classifier, data representing the amount of post translational modifications (PTMs) for a set of tau protein peptide fragments from a test subject, wherein the classifier being for determining whether the amount of PTMs for the set of tau protein peptide fragments classifies with (A) a set of data repressing the amount of PTMs for the set of tau protein peptide fragments from a first group of individuals who have the tauopathy; as opposed to classifying with (B) a set of data repressing the amount of PTMs for the set of tau protein peptide fragments from a second group of individuals who does not have the tauopathy; applying, by the one or more data processing devices, the classifier to the data representing the amount of PTMs for the set of tau protein peptide fragments from the test subject; and determining whether the test subject is classified with the first group of individuals who have the tauopathy or the second group of individuals who do not have the tauopathy.

In some embodiments, the set of the tau peptide fragments comprises:

(QEFEVMEDHAGTYGLGDR), SEQ ID NO: 1

(DQGGYTMHQDQEGDTDAGLK), SEQ ID NO: 2

(ESPLQTPTEDGSEEPGSETSDAK), SEQ ID NO: 3

(STPTAEDVTAPLVDEGAPGK), SEQ ID NO: 4

(QAAAQPHTEIPEGTTAEEAGIGDTPSLEDEAAGHVTQAR), SEQ ID NO: 5

(TPPSSGEPPK), SEQ ID NO: 6

(SGYSSPGSPGTPGSR), SEQ ID NO: 7

(TPSLPTPPTR), SEQ ID NO: 8

(TPSLPTPPTREPK), SEQ ID NO: 9

(LQTAPVPMPDLK), SEQ ID NO: 10

(KLDLSNVQSK), SEQ ID NO: 11

(LDLSNVQSK), SEQ ID NO: 12

(HVPGGGSVQIVYKPVDLSK), SEQ ID NO: 13

(IGSLDNITHVPGGGNK), SEQ ID NO: 14

(TDHGAEIVYK), SEQ ID NO: 15

(SPVVSGDTSPR), SEQ ID NO: 16
and (HLSNVSSTGSIDMVDSPQLATLADEVSAVSASSLAK). SEQ ID NO: 17

In some embodiments, the classifier is based on Random forest (RF), Neural networks (Nnet), k-nearest neighbor (KNN), Learning Vector Quantization (LVQ), Linear Discriminant Analysis (LDA), and Support Vector Machines (SVM).

In some embodiments, the tauopathy is selected from the group consisting of Alzheimer's disease (AD), Argyrophilic grain disease (AGD), Corticobasal degeneration (CBD), Pick's disease (PiD) and Progressive supranuclear palsy (PSP).

In some embodiments, the tauopathy is AD, and the set of the tau peptide fragments comprises one or more tau peptide fragments selected from the group of SEQ ID NO: 8, SEQ ID NO: 10, SEQ ID NO: 11, SEQ ID NO: 13, SEQ ID NO: 14, and SEQ ID NO: 17.

In some embodiments, the tauopathy is AD, and the set of the tau peptide fragments comprises SEQ ID NO: 8 and/or SEQ ID NO: 17.

In some embodiments, the tauopathy is CBD, and the set of the tau peptide fragments comprises one or more tau peptide fragments selected from the group of SEQ ID NO: 4, SEQ ID NO: 11, SEQ ID NO: 12, SEQ ID NO: 13, SEQ ID NO: 14, and SEQ ID NO: 15.

In some embodiments, the tauopathy is CBD, and the set of the tau peptide fragments comprises SEQ ID NO: 4.

In some embodiments, the tauopathy is PiD, and the set of the tau peptide fragments comprises one or more tau peptide fragments selected from the group of SEQ ID NO: 1, SEQ ID NO: 10, SEQ ID NO: 12, SEQ ID NO: 13, SEQ ID NO: 14, and SEQ ID NO: 17.

In some embodiments, the tauopathy is CBD, and the set of the tau peptide fragments comprises SEQ ID NO: 13.

In some embodiments, the tauopathy is PSP, and the set of the tau peptide fragments comprises one or more tau peptide fragments selected from the group of SEQ ID NO: 3, SEQ ID NO: 7, SEQ ID NO: 8, SEQ ID NO: 11, SEQ ID NO: 12, and SEQ ID NO: 15.

In some embodiments, the tauopathy is CBD, and the set of the tau peptide fragments comprises SEQ ID NO: 3.

In some embodiments, the set of the tau peptide fragments comprises one or more tau peptide fragments selected from the group of SEQ ID NO: 1-17, and 18-57. In some embodiments, the set of the tau peptide fragments comprises one or more tau peptide fragments selected from the group of

```
QEFEVMEDHAGTYGLGDR;                            (SEQ ID NO: 1)

DQGGYTMHQDQEGDTDAGL;                           (SEQ ID NO: 55)

ESPLQTPTEDGSEEPGSETSDAK;                       (SEQ ID NO: 3)

STPTAEDVTAPLVDEGAPGK;                          (SEQ ID NO: 4)

QAAAQPHTEIPEGTTAEEAGIGDTPSLEDEAAGHVTQAR;       (SEQ ID NO: 5)

TPPSSGEPPK,                                    (SEQ ID NO: 6)

SGYSSPGSPGTPGSR;                               (SEQ ID NO: 7)

TPSLPTPPTR,                                    (SEQ ID NO: 8)

TPSLPTPPTREPK;                                 (SEQ ID NO: 9)

LQTAPVPMPDLK;                                  (SEQ ID NO: 10)

11 =
KLDLSNVQSK;                                    (SEQ ID NO: 11)

LDLSNVQSK;                                     (SEQ ID NO: 12)

13 =
HVPGGGSVQIVYKPVDLSK;                           (SEQ ID NO: 13)

IGSLDNITHVPGGGNK;                              (SEQ ID NO: 14)

TDHGAEIVYKSPVVSGDTSPR;                         (SEQ ID NO: 56)
and

HLSNVSSTGSIDMVDSPQLATLADEVSASLAK.              (SEQ ID NO: 54)
```

In some embodiments, the set of the tau peptide fragments comprises one or more tau peptide fragments selected from the group of

```
QEFEVMEDHAGTYGLGDR;                            (SEQ ID NO: 1)

ESPLQTPTEDGSEEPGSETSDAK;                       (SEQ ID NO: 3)

STPTAEDVTAPLVDEGAPGK;                          (SEQ ID NO: 4)

SGYSSPGSPGTPGSR;                               (SEQ ID NO: 7)

TPSLPTPPTR;                                    (SEQ ID NO: 8)

LQTAPVPMPDLK;                                  (SEQ ID NO: 10)

KLDLSNVQSK;                                    (SEQ ID NO: 11)

LDLSNVQSK;                                     (SEQ ID NO: 12)

HVPGGGSVQIVYKPVDLSK;                           (SEQ ID NO: 13)

IGSLDNITHVPGGGNK;                              (SEQ ID NO: 14)

TDHGAEIVYK;                                    (SEQ ID NO: 15)
and

HLSNVSSTGSIDMVDSPQLATLADEVSASLAK.              (SEQ ID NO: 54)
```

Tau Peptides with PTMs

Table 1 lists peptides detected with their sequence being ordered by their amino acid location in tau (N- to C-terminal). Peptide modification extent is determined by the difference of normalized L/H ratio to ctrl-tau, where 100% represents a peptide that is fully modified (no unmodified peptide detected). P-values were calculated in comparison to control tau (student t-test). Corresponding phosphorylation sites detected by complementary LC-MS/MS analysis are also shown.

Peptide fragments with the modifications as listed in Table 1 and Table 7 can be used as epitopes. Antibody or antibody fragments that immunospecifically bind to these epitopes can be used for various purposes, e.g., diagnosis and treatment.

Antibodies and Antibody Fragments

Peptides that immunospecifically bind to tau proteins with PTMs can be prepared from immune cells and molecular biology techniques. In some embodiments, these peptides do not bind to tau proteins without such PTMs.

The method herein involves preparation of peptides directed against one or more different antigens. In some embodiments, the antigen is a full length tau protein with one or more PTMs of interest. In some embodiments, the antigen is a tau peptide fragment with one or more PTMs of interest.

In some embodiments, an animal or host to be immunized with the antigens is selected. In the preferred embodiment, the animal is a rodent, e.g. a mouse. The amount of antigen of interest administered to the host animal may, for example, range from about 0.01 µg to about 250 µg, preferably from about 0.1 µg to about 100 µg. Where the primary response is weak, it may be desirable to boost the animal at spaced intervals until the antibody titer increases or plateaus. After immunization, samples of serum (test bleeds) may be taken to check the production of specific antibodies. Preferably, the host animal is given a final boost about 3-5 days prior to isolation of immune cells from the host animal. Monoclonal antibodies may be made using the hybridoma method first described by Kohler et al., Nature, 256:495 (1975). In the hybridoma method, "immune cells" that produce or are capable of producing polyclonal antibodies are obtained from the animal immunized as described above. Various immune cells are described above, with lymph nodes or spleen being the preferred source of immune cells for generating monoclonal antibodies. Such cells may then be fused with myeloma cells using a suitable "fusing agent", such as polyethylene glycol or Sendai virus, to form a hybridoma cell. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferred myeloma cells are those that fuse efficiently, support stable high-level production of antibody by the selected antibody-producing cells, and are sensitive to a medium such as HAT medium.

In some embodiments, obtaining or targeting immune cells can include one or more and/or combinations of, for example: obtaining or providing an antigen (e.g., peptide fragments with modifications as shown in Table 1 and Table 7) that can bind (e.g., bind specifically) to a target immune cell; contacting the antigen with a sample; detecting the antigen; determining whether the antigen is bound to a target immune cell; and, if the antigen is bound to a target immune cell, then obtaining the target immune cell.

Methods for isolating or purifying genetic material (e.g., DNA and/or mRNA) from the obtained target immune cell are known in the art and are exemplified herein. Once such genetic material has been obtained, methods for using it to produce the therapeutic compositions disclosed herein are known in the art and/or are summarized below. Genetic material can be varied, using techniques known in the art to create polypeptide variants disclosed herein. Generating polypeptides from nucleic acids (e.g., cDNA) contained within or obtained from the target cell can include, for example, analysis, e.g., sequencing of heavy and light chain variable domains from target immune cells (e.g., single or isolated identified target immune cells).

In some embodiments, methods can include generating fully human antibodies, or fragments thereof (e.g., as disclosed above), and humanization of nonhuman antibodies. DNA can be readily isolated and/or sequenced from the obtained immune cells using conventional procedures (e.g., by using oligonucleotide probes that are capable of binding specifically to genes encoding the heavy and light chains of murine antibodies).

Once isolated, DNA can be placed into expression vectors, which are then transfected into host cells such as Escherichia coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol: 2 6-262 (1993) and Pluckthun, Immunol. Revs., 130:1 1-188 (1992).

Recombinant expression of an antibody or variant thereof generally requires construction of an expression vector containing a polynucleotide that encodes the antibody. The invention, thus, provides replicable vectors comprising a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., U.S. Pat. Nos. 5,981,216; 5,591,639; 5,658,759 and 5,122,464) and the variable domain of the antibody may be cloned into such a vector for expression of the entire heavy, the entire light chain, or both the entire heavy and light chains.

Once the expression vector is transferred to a host cell by conventional techniques, the transfected cells are then cultured by conventional techniques to produce an antibody. Thus, the invention includes host cells containing a polynucleotide encoding an antibody of the invention or fragments thereof, or a heavy or light chain thereof, or portion thereof, or a single-chain antibody of the invention, operably linked to a heterologous promoter. In certain embodiments for the expression of double-chained antibodies, vectors encoding both the heavy and light chains may be co-expressed in the host cell for expression of the entire immunoglobulin molecule, as detailed below.

Mammalian cell lines available as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), SP20, CRL7O3O and HsS78Bst cells. In some embodiments, human cell lines developed by immortalizing human lymphocytes can be used to recombinantly produce monoclonal antibodies.

Therapeutic and Diagnostic Use

The disclosure provides methods of treatment that include administering to a subject a composition disclosed herein.

In some embodiments, subject selection can include obtaining a sample from a subject (e.g., a candidate subject) and testing the sample for an indication that the subject is suitable for selection. In some embodiments, the subject can be confirmed or identified, e.g. by a health care professional, as having had or having a condition or disease. In some embodiments, exhibition of a positive response towards a condition or disease can be made from patient records, family history, and/or detecting an indication of a positive response. In some embodiments multiple parties can be included in subject selection. For example, a first party can obtain a sample from a candidate subject and a second party can test the sample. In some embodiments, subjects can be selected and/or referred by a medical practitioner (e.g., a general practitioner). In some embodiments, subject selection can include obtaining a sample from a selected subject and storing the sample and/or using the in the methods disclosed herein.

In some embodiments, the composition disclosed herein can be used for treating various tauopathies. For example, an antibody or an antibody fragment thereof that targets tau protein with one or more specific PTMs can be used to treat a tauopathy, if the tauopathy is associated with tau proteins having these specific PTMs.

In some embodiments, the antibodies or the fragments thereof can be used in imaging agents. These imaging agents can target tau proteins with specific modification as described in this disclosure. In some embodiments, these in vivo biomarkers and imaging reagents can be used for diagnosis and prognosis, e.g. for staging disease and to measure efficacy of treatment in clinical trials.

In some embodiments, the antibodies or the fragments thereof can be used for various diagnosis purpose. In some embodiments, a sample is collected from a subject. An antibody or antibody fragment thereof that target one or more PTMs of interest can be used to determine whether the tau protein in the subject has PTMs of interest. In some embodiments, the PTMs of interest may be associated with a tauopathy. If it is determined that the subject has the PTMs of interest, then the subject is determined to have the tauopathy (e.g., Alzheimer's disease (AD), Argyrophilic grain disease (AGD), Corticobasal degeneration (CBD), Pick's disease (PiD) and Progressive supranuclear palsy (PSP)).

Methods of Treatment

The methods described herein include methods for the treatment of disorders associated with tauopathies (e.g., AD, AGD, CBD, PiD, PSP). In some embodiments, the disorder is Alzheimer's disease. Generally, the methods include administering a therapeutically effective amount of a composition as described herein (e.g., antibody or antibody fragment thereof), to a subject who is in need of, or who has been determined to be in need of, such treatment.

As used in this context, to "treat" means to ameliorate at least one symptom of the disorder associated with tauopathies. Often, the treatment results in improvement of symptoms. In some embodiments, a treatment can result in a reduction in tau protein aggregation.

In some embodiments, the treatment reduces the risk of developing disorders associated with tauopathies (e.g., AD, AGD, CBD, PiD, PSP). Generally, the methods include administering a therapeutically effective amount of a composition as described herein (e.g., antibody or antibody fragment thereof), to a subject who is determined to have a risk of developing disorders associated with tauopathies (e.g., AD, AGD, CBD, PiD, PSP). In some embodiments, the subjects have some early symptoms for tauopathies, e.g., changes in personality, behavior, sleep patterns, and executive function, memory loss, confusion, inability to learn new things, and difficulty carrying out multistep tasks, etc.

Pharmaceutical Compositions

The methods described herein include the use of pharmaceutical compositions comprising a polypeptide that immunospecifically binds the tau proteins with PTMs as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active composition in the required amount in an appropriate solvent with one or a combination of ingredients enumerated above, as required, followed by filtered sterilization. Generally, dispersions are prepared by incorporating the active composition into a sterile vehicle, which contains a basic dispersion medium and the required other ingredients from those enumerated above.

The pharmaceutical compositions can be included in a container, pack, or dispenser together with instructions for administration.

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of an active agent (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Methods of Screening

Included herein are methods for screening test compounds, e.g., polypeptides, polynucleotides, inorganic or organic large or small molecule test compounds, to identify agents useful in the treatment of disorders associated with tau protein aggregation, and tauopathies, e.g., Alzheimer's Disease (AD), Progressive Supranuclear Palsy (PSP), Corticobasal Degeneration (CBD), Pick's Disease (PiD), Argyrophilic grain disease (AGD), Frontotemporal dementia and Parkinsonism associated with chromosome 17 (FTDP-17), Parkinson's disease, stroke, traumatic brain injury, mild cognitive impairment and the like. Agents useful in the treatment of disorders associated with tau protein aggregation include, for example, compounds, e.g., polypeptides, such as an antibody or other antigen binding molecule, polynucleotides, inorganic or organic large or small molecule compounds that bind to one or more tau PTM and/or inhibit association of PTM tau proteins.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a protein sample, a cell or living tissue or organ, e.g., an eye, and one or more effects of the test compound is evaluated. In a cultured or primary cell for example, the ability of the test compound to inhibit the PTM of interest or promote the PTM of interest is determined.

In some embodiments, the test sample is, or is derived from (e.g., a sample taken from) an in vivo model of a disorder as described herein. For example, an animal model, e.g., a rodent such as a rat, can be used.

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. *Modern genetic Analysis*, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect an effect on PTMs. Ability to modulate PTMs can be evaluated, e.g., using methods as described in this disclosure.

A test compound that has been screened by a method described herein and determined to inhibit PTMs of interest, or inhibit tau protein aggregation, or promote the PTM of interest can be considered a candidate compound. A candidate compound that has been screened, e.g., in an in vivo model of a disorder, e.g., AD, PSP, CBD, PiD, AGD, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that have the ability to inhibit certain PTMs, promote certain PTM, or inhibit tau protein aggregations) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating tauopathies, e.g., AD, AGD, CBD, PiD, PSP, or symptoms associated with tauopathies. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of a tauopathy (e.g., AD, AGD, CBD, PiD, PSP), as described herein. The animal can be monitored for a change in the disorder, e.g., for an improvement in a parameter of the disorder, e.g., a parameter related to clinical outcome. In some embodiments, the parameter is memory, and an improvement would be an increase in short-term memory.

EXAMPLES

The invention is further described in the following examples, which do not limit the scope of the invention described in the claims.

Example 1: Quantifying the Extent of Tau PTMs In Vitro

Experiments were performed to quantify the extent of Tau PTMs by FLEXiTau in vitro.
Materials and Methods
Cells and Viruses
Sf9 cells were obtained from Invitrogen (San Diego, Calif.) and grown at 27° C. in monolayer culture Grace's medium (Life Technologies, Gaithersburg, Md.) supplemented with 10% fetal bovine serum, 50 µg/ml Gentamycin, and 2.5 µg/ml Amphotericin. Sapphire™ baculovirus DNA was obtained from Orbigen/Biozol (Eching, Germany), and pVL1392 was from Invitrogen.

Baculovirus Construction
The hTau40 cDNA, the longest Tau isoform in human CNS (2N4R), was excised from the bacterial expression vector pNG2 (37) with XbaI and BamHI and inserted into the baculovirus transfer vector pVL1392. For the construction of Tau containing baculovirus vectors, Sapphire™ baculovirus DNA was used for homologous recombination with pVLhtau40 plasmid in Sf9 cells.
Sf9 Tau Protein Preparation and Purification
Phosphorylated Sf9 tau ("P-tau") was purified by the procedure as described in Tepper, K., et al. "Oligomer formation of tau protein hyperphosphorylated in cells." Journal of Biological Chemistry 289.49 (2014): 34389-34407. Briefly, Sf9-cells were infected with recombinant virus at a MOI of 1-5, typically in six T150 cell culture flasks containing 75% confluent Sf9 cells. Cells were incubated for three days at 27° C. and collected directly in lysis buffer (50 mM Tris HCl pH 7.4, 500 mM NaCl, 10% glycerol, 1% Nonidet-P40, 5 mM dithiothreitol (DTT), 10 mM ethylene glycol tetra-acetic acid (EGTA), 20 mM NaF, 1 mM orthovanadate, 5 µM microcystin, 10 µg/ml each of protease inhibitors leupeptin, aprotinin, and pepstatin). For the generation of "PP-tau" (higher phosphorylated Sf9 P-tau), Sf9 cells were treated for 1 h with 0.2 µM okadaic acid (OA, a phosphatase inhibitor, Enzo-Lifescience, Farmingdale, N.Y.) 1 hour prior to harvesting. Lysates were boiled in a water bath at 100° C. for 10 min and cell debris was removed by centrifugation for 15 min at 16,000×g. The supernatant containing soluble tau protein was concentrated in Millipore Amicon Ultra-4 Centrifugal filter units (MWCO 3 kDa). The concentrated material was applied to a size exclusion column Superdex G200 (GE Healthcare, Little Chalfont, UK) and eluted with PBS Buffer (pH 7.4; 1 mM DTT), collecting 1 ml fractions.

A second purification step was performed, using anion exchange chromatography on a MonoQ HR 16/10 column (GE Healthcare, Little Chalfont, UK). For this purpose the tau-containing fractions of the G200-column were pooled and dialyzed against buffer A (100 mM MES (pH 6.8), 2 mM DTT, 1 mM NaEGTA, 1 mM MgSO4, 0.1 mM PMSF), before loading onto the MonoQ column. Tau protein was eluted by a three step salt gradient (Buffer A supplemented with 1 M NaCl was used to create salt gradient steps of 0-0.2 M, 0.2-0.3 M and 0.3-1 M NaCl). To generate dephosphorylated Sf9 tau ("deP-tau") 30 µg purified P-tau protein was incubated with 10 U of alkaline phosphatase (FastAP, Invitrogen, Carlsbad, Calif.) for ~16 hours at 37° C. The enzyme was removed afterwards by precipitation (5 mM DTT, 0.5 M NaCl), followed by centrifugation and dialysis to PBS. Protein amounts were estimated by a bicinchoninic acid test (BCA, Sigma, St. Louis, Mo.). Samples were additionally analyzed by SDS-PAGE to verify purity and protein degradation.
Preparation of Human Tau40 from E. coli
Expression and purification of human Tau40 from E. coli cells was carried out by the procedure as described in Barghorn, S., et al., "Purification of recombinant tau protein and preparation of Alzheimer-paired helical filaments in vitro." Amyloid Proteins: Methods and Protocols (2005): 35-51. Note that human Tau40 is purified differently to Sf9 tau, as it does not carry the negative charges of phosphates. Human Tau40 was first purified by cation exchange chromatography (SP sepharose; GE healthcare, Little Chalfont, UK), and then by size exclusion chromatography (G200), as described above.

Extraction of PHF-Tau from AD Brain

Human AD brain tissue was obtained from the Human Brain and Spinal Fluid Resource Center, West Los Angeles and the Memory and Aging Center at the University of California, San Francisco. BA39 angular gyms brain blocks (1-3 g) were dissected from frozen brain slabs and shipped to Boston Children's Hospital on dry ice. While still frozen, 0.3 g sections were homogenized in 5 volumes 25 mM Tris-HCl buffer, pH 7.4, containing 150 mM NaCl, 10 mM ethylene diamine tetraacetic acid (EDTA), 10 mM EGTA, 1 mM DTT, 10 mM nicotinamide, 2 µM trichostatin A, phosphatase inhibitor cocktail (Sigma, St. Louis, Mo.), protease inhibitor cocktail (Roche, Basel, Switzerland). Crude brain homogenates were then clarified by centrifugation at 11,000×g for 30 min at 4° C. Pellets were re-homogenized in half the volume of buffer used before and re-centrifuged at 11,000×g for 30 min at 4° C. Supernatants were pooled and used as a crude tau fraction (unfractionated homogenate). Part of the crude tau fraction was treated with sarkosyl (1% final concentration) for 60 min at 4° C. and ultracentrifuged at 100,000×g for 2 h at 4° C. The supernatant was transferred to a new tube (sarkosyl soluble fraction). The pellet was airdried, washed twice with 50 µl ddH2O and solubilized in Tris buffer containing 1 SDS, 10 mM nicotinamide, 2 µM trichostatin A, and phosphatase and protease inhibitor cocktail (0.3 µl buffer per mg wet weight of the starting material). Solubilized pellets were used as the sarkosyl insoluble tau fraction. All samples were stored at −80° C. until use.

Preparation of Heavy Tau Standard

Full-length human 4R2N (GI: 294862262) was subcloned into the previously generated pEU-E01-TEV-N1-AQUA vector as described in Venne, A. et. al., "The next level of complexity: crosstalk of posttranslational modifications." Proteomics 14.4-5 (2014): 513-524. After verification by DNA sequencing (Molecular Genetics Core Facility, Children's Hospital Boston), tau was in vitro transcribed and translated in a cell-free wheat germ expression (WGE) system according to the manufacturer's protocols (Cell Free Sciences, Wheat Germ Expression H Kit-NA). Expression was carried out in the presence of isotope labeled lysine (13C6 15N2), arginine (13C6 15N4) and asparagine (13C4 15N1). Heavy tau standard was batch-purified using Ni-Sepharose beads (Ni-Sepharose High Performance resin, GE Healthcare, Little Chalfont, UK). Briefly, after a prewash in binding buffer (20 mM phosphate buffer, pH7.5, 500 mM NaCl, 10 mM imidazole) beads were incubated with WGE (ratio 1:4) for 1 h rotating head-over-head at 4° C. for binding. After removal of the unbound fraction, beads were washed once with 50 µl and 3 times with 500 µl wash buffer (20 mM phosphate buffer, pH7.5, 500 mM NaCl, 10 mM imidazole). Elution of tau was carried out in three steps (50 µl binding buffer with 100/300/500 mM imidazole, respectively). Purification was verified by SDS-PAGE and western blot analysis. Pooled elutes were stored at −20° C. in 50 µl aliquots.

SDS-PAGE and Silver Stained

Samples were boiled 5 min at 98° C. in 2× Laemmli buffer and separated by SDS-PAGE (4-12% Bis-Tris, NuPage, Invitrogen, Carlsbad, Calif.) at 120 V. Gels were stained with colloidal blue (Nuvex, Invitrogen, Carlsbad, Calif.). Silver staining was performed by fixing the gels in 30% ethanol/10% acidic acid solution, cross-linking the proteins (in 0.5% glutarealdehyde) and staining in 0.1% AgNO3 solution, followed by development with 2.5% $Na_2CO_3$/1% formaldehyde until the protein marker was visible.

Sample Preparation for MS

Heavy tau standard was subjected to incubation with lambda protein phosphatase (New England Biolabs, Ipswich, Mass.) for 30 min at 30° C. at 300 rpm. FASP digestion—filter aided sample preparation was performed using 1 µg of Sf9 tau and brain-derived tau (20% volume of solubilized sarkosyl pellets). For spikes, dephosphorylated standard was added prior to digest. Samples were reduced with 50 mM DTT (20 min, 56° C.) and alkylated with 1% acrylamide (30 min, RT). Samples were diluted with 8 M urea and processed using filter-aided sample preparation (FASP) following the manufacturer's protocol (FASP Protein Digestion Kit, Expedeon, San Diego, Calif.). Briefly, filters were washed twice with 8 M urea, 3 times with 50 mM ammonium bicarbonate (ABC) and samples were digested with 2 ng/µl trypsin (sequencing grade modified trypsin, Promega, Madison, Wis.) overnight at 37° C. For LysC digest, the last two washes were performed using LysC buffer (0.1 M Tris, pH 9.2, 1 mM EDTA), followed by overnight incubation at 37° C. with 4 ng/µl LysC (endoproteinase Lys-C sequencing grade, Roche, Basel, Switzerland) in LysC buffer. After digestion, peptides were eluted from the membrane by two washes with 50 mM ABC (or LysC buffer for LysC samples) and one wash with 0.5 M NaCl. Peptides were acidified with formic acid, desalted using C18 microspin tips (Nest Group, Southborough, Mass.) and dried under vacuum. Peptides were reconstituted in sample buffer (5% formic acid, 5% acetonitrile) containing 10 fmol/µl non-labeled FLEX-peptide (TENLYFQGDISR, synthesized by Sigma Life Science, quantified via amino acid analysis of Molecular Biology Core Facilities, Dana Farber Cancer Institute, Boston) and indexed retention time (iRT) peptides (Biognosys) by the methods as described in Escher, Claudia, et al. "Using iRT, a normalized retention time for more targeted measurement of peptides." Proteomics 12.8 (2012): 1111-1121.

LC-MS/MS Measurements

Heavy tau standard was analyzed on a quadrupole Orbitrap tandem mass spectrometer (Q Exactive, Thermo Fisher Scientific, Waltham, Mass.) hyphenated with a micro-autosampler AS2 and a nanoflow HPLC pump (both Eksigent, Dublin, Calif.), using the trap-elute chip system (cHiPLC nanoflex, Eksigent, Dublin, Calif.). Peptides were first loaded onto the trap-chip (200 µm×75 µm, ChromXP C18-CL 3 µm 120 A, Nano cHiPLC Eksigent, Dublin, Calif.) and then separated using an analytical column-chip (75 µm×15 cm, ChromXP C18-CL 3 µm 120 A, Nano cHiPLC Eksigent) by a linear 30 min gradient from 95% buffer A (0.1% (v/v) formic acid in HPLC-$H_2O$) and 5% buffer B (0.2% (v/v) formic acid in ACN) to 35% buffer B. A full mass spectrum with resolution of 70,000 (relative to an m/z of 200) was acquired in a mass range of 300-1500 m/z (AGC target $3\times10^6$, maximum injection time 20 ms). The 10 most intense ions were selected for fragmentation via higher-energy c-trap dissociation (HCD, resolution 17,500, AGC target $2\times10^5$, maximum injection time 250 ms, isolation window 1.6 m/z, normalized collision energy 27%). The dynamic exclusion time was set to 20 s and unassigned/singly charged ions were not selected. In addition, heavy tau standard was analyzed on an Sciex Triple TOF 5600 to generate fragment-ion spectra comparable to the employed SRM instrument (Sciex QTRAP 5500), using the same LC setup as described above. The Triple TOF was operated in data-dependent TOP30 mode with following settings: MS1 mass range 350-1300 Th with 175 ms accumulation time; MS2 mass range 100-1500 Th with 25 ms accumulation time and following MS2 selection criteria: UNIT resolution, intensity threshold 8 cts; charge states 2-5. To identify sites of modifications on tau, Sf9 tau digests were analyzed on the Q-Exactive applying the settings described above, replacing the chip-system with an in-house packed C-18 analytical column (Magic C18 particles, 3 µm, 200 Å, Michrom Bioresource, Auburn, Calif.). After initial measurements, an inclusion list containing all identified phosphorylated tau peptides was created using Skyline. For final measurements, following settings were used in order to increase peptide identification: AGC target $5\times10^6$, maximum injection time 120 ms, MS/MS resolution 35,000, AGC target $2\times10^5$, maximum injection time 200 ms, isolation window 2 m/z. The dynamic exclusion time was set to 4 s and unassigned and charge state 1 and >5 ions were rejected. The inclusion list was turned on allowing picking others if idle.

LC-MS/MS Data Processing

Q Exactive raw files were converted into mgf data format using ProteoWizard as described in Kessner, Darren, et al. "ProteoWizard: open source software for rapid proteomics tools development." Bioinformatics 24.21 (2008): 2534-2536. The spectra were centroided and filtered using ms2preproc to select the 6 most intense peaks in a 30 Th window. MS/MS spectra from mgf or wiff files were assigned to peptides and corresponding proteins using ProteinPilot™ Software 4.5 Beta (Paragon Algorithm 4.5.0.0. 1575, Sciex). The following settings were applied: sample type 'SILAC (Lys+8, Arg+10, Asp+5)', instrument: 'Orbi MS (1-3 ppm)', 'Orbi MS/MS' and 'TripleTOF 5600' respectively; 'Urea denaturation'; 'rapid' search mode. Spectra were searched against a custom database containing wheat germ proteins and the human 4R2N Tau sequence tagged with the FLEX peptide. For the mapping of Sf9 tau PTMs, raw files were converted and processed in ProteinPilot as described above except for following search parameters: 'thorough' search mode, 'phosphorylation emphasis', 'acetylation emphasis', 'ID focus on biological modifications' and using *Homo Sapiens* database. Note that ProteinPilot doesn't allow the user to pick mass tolerances and number of missed cleavages. All MS/MS spectra of identified posttranslationally modified peptides were subjected to manual verification.

SRM Assay Development

MS analysis of a tryptic digest of the expressed purified heavy tau standard was used to develop the SRM assay. Tau peptides and corresponding product ions for each peptide were first characterized by LC-MS/MS using the setup described above. Multiple measurements of up to 400 fmol of tau were performed using two different instruments platforms: First, a Thermo Scientific Q Exactive was used to maximize the number of peptide identifications. In addition, the purified tau standard was analyzed on a Sciex Triple TOF 5600 to generate fragmentation spectra comparable to the employed SRM instrument (Sciex QTRAP 5500, Framingham, Mass.). To generate a spectral library from these datasets, xml files were extracted from ProteinPilot and loaded into Skyline using cut off score of 0.5 as described in MacLean, Brendan, et al. "Skyline: an open source document editor for creating and analyzing targeted proteomics experiments." Bioinformatics 26.7 (2010): 966-968. A FASTA file containing the 4R2N tau protein sequence tagged with the FLEX-peptide was imported, using a wheat germ protein database as a background proteome. Filter settings for tryptic peptides (Trypsin/P KR|−) were as follows: a maximum of 2 missed cleavages, a peptide length between 5 and 40 amino acids, a maximum of 3 variable structural modifications (cysteine propionamidation, serine/threonine phosphorylation, methionine oxidation and asparagine/glutamine deamidation) and a maximum of 1 neutral loss. The spectra were used to confirm identities, extract the optimal fragment ions for SRM analysis and obtain retention times (for SRM assay development, see below). An initial transition list for each tryptic and LysC samples were generated choosing 8 most intense product ions from the library spectrum, considering only y ions with charges 1 and 2 (from precursor ions with charges 2, 3 and 4) from ion 3 to last ion −1. The transition lists were validated and optimized after SRM measurements.

SRM Measurements and Data Processing

The SRM assay using the transition lists developed above was tested using the tau standard. Measurements were performed on a triple quadrupole mass spectrometer (5500 QTRAP, Sciex, Framingham, Mass.) using the same LC trap-elute chip setup as described above. Measurements were done using a scheduled SRM mode. Final measurements were performed using a retention time window of 7 min and a maximum of 250 transitions per method. Resulting SRM data were analyzed and manually validated in Skyline. Transition groups corresponding to the targeted peptides were evaluated based on specific parameters (in order of importance): co-elution of light and heavy peptides; rank correlation between the SRM relative intensities and the intensities obtained in the MS/MS spectra; and consistence among technical and biological replicates. Using these criteria, the transition lists were reduced from 8 to 4-5 most intense product ions per peptide. Absolute quantification of the standard was carried out using SRM relative intensities between the heavy FLEX-peptide and its light counterpart FLEX-peptide, as described in Venne, A. S., Kollipara, L., and Zahedi, R. P. (2014) The next level of complexity: crosstalk of posttranslational modifications. Proteomics 14, 513-524. To ensure linearity of product ion signals and to determine detection limit of the assay, a dilution series of heavy tau standard spanning four orders of magnitude from 0.8-800 fmol was prepared and measured in triplicates using the optimized transition list.

Figure 3A:
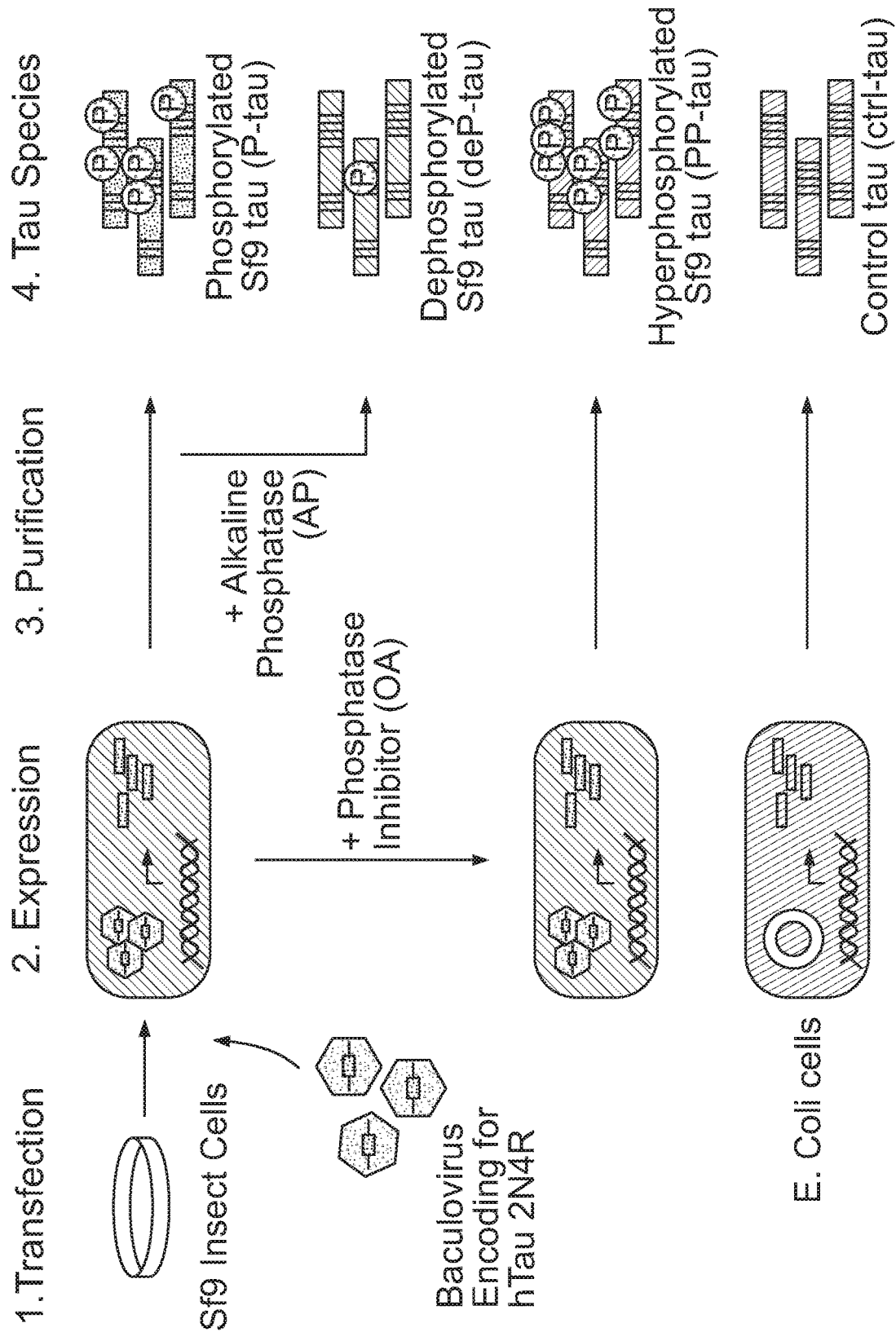
FIG. 3A is a schematic diagram showing an exemplary method for hyper-phosphorylated tau sample preparation.
Figure 3B:
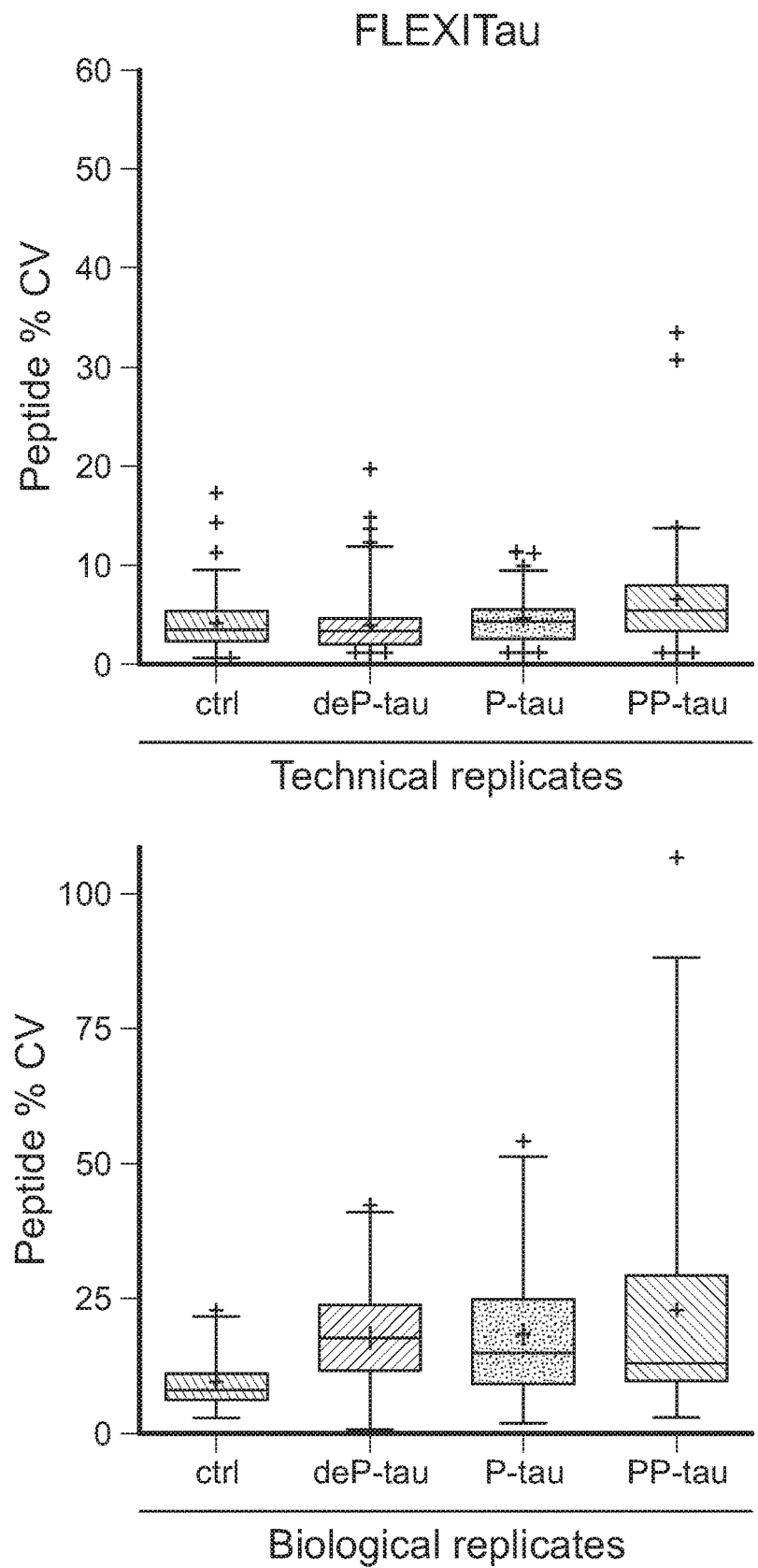
FIG. 3B is a graph showing reproducibility of one exemplary method of quantifying the amount of post-translational modifications.

Final measurements of samples were performed in scheduled SRM mode using the validated transition lists, a retention time window of 5 min and a total scan time of 1.2 s, which ensured a dwell time over 20 ms per transition. To achieve the desired concentration range, data from a 1:10 dilution of the samples were initially collected and the injection amount was adjusted appropriately. Blank runs between SRM measurements ensured minimal sample carry over, and three replicate injections were measured per sample (MS injection on separate days). SRM data were analyzed and manually validated in Skyline. Peptide transitions were re-evaluated for variability, similarity between y-ion ratios, elution times, and interfering signals by manual analysis. For quantification, the 3 highest intense transitions were used. Ratios of light-to-heavy (L/H) peak intensities were normalized using the median of the 3 peptides with highest ratio. To assess quantification precision of technical and biological replicates, averages of normalized L/H ratio coefficient of variation (CVs) were calculated from the triplicate measurements for each biological replicate, and subsequently the average and % CV from the three biological replicates was calculated for each species. FLEXiTau data was expressed as mean+/−STDEV and statistically analyzed by the Student's t test between two groups (FIG. 3B). Statistical significance was accepted at $p<0.05$ level. For the calculation of the modification extent of each peptide, first the average of technical replicates (normalized L/H ratio) was taken, followed by normalization of each sample by the average of all control samples. The modification extent for each biological replicate was then calculated by subtracting this value from 1. Negative values were transformed to zero and averages of the three biological replicates were calculated. FLEXITau data was expressed as mean+/−STDEV of normalized L/H ratio of biological replicates and analyzed by the Student's t test (two-sided). Statistical significance was accepted at the p<0.05 level.

Calculation of Site-Occupancy

Figure 4B:
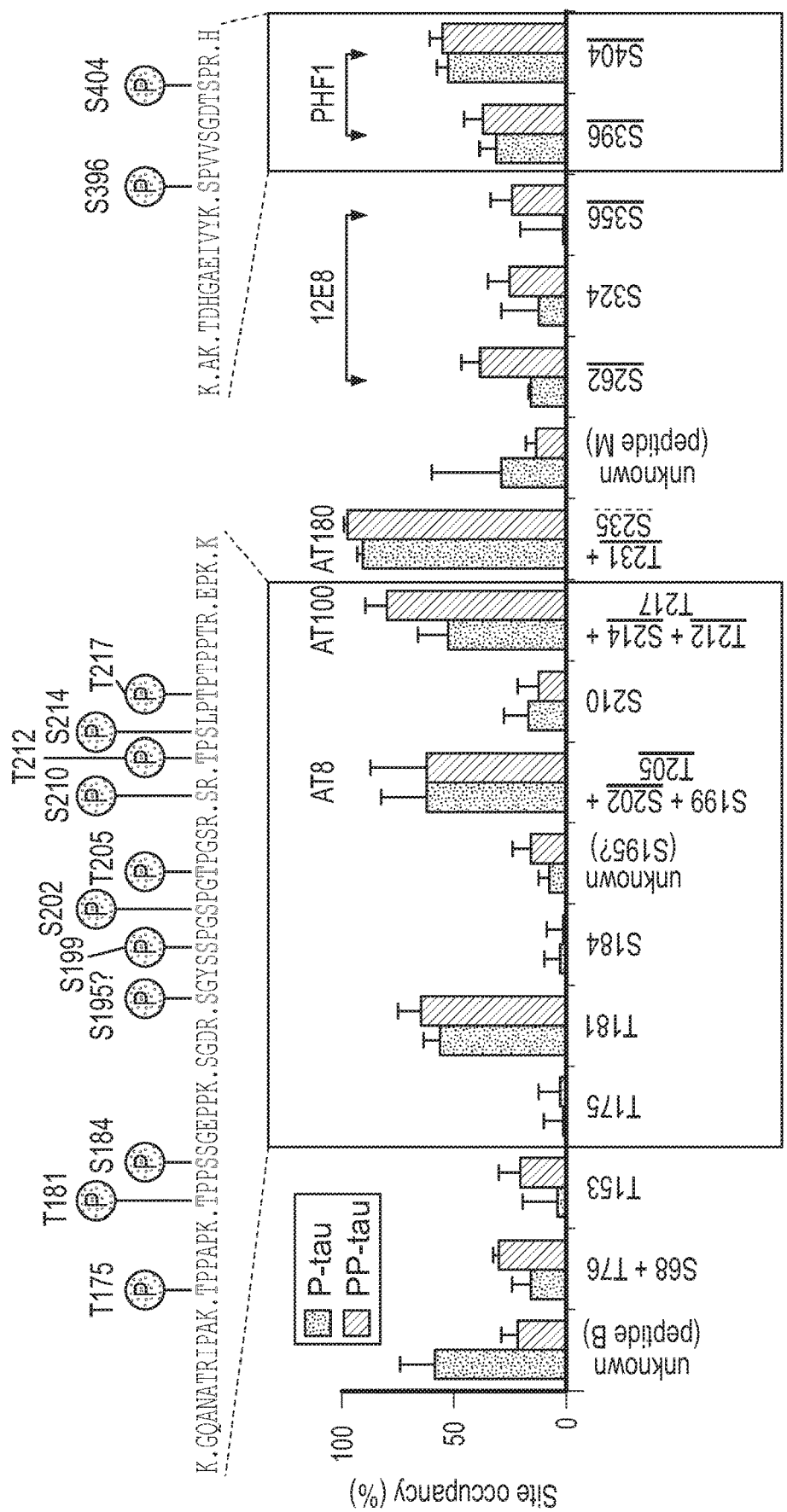
FIG. 4B is a graph showing the extent of phosphorylation for identified sites.
Figure 4C:
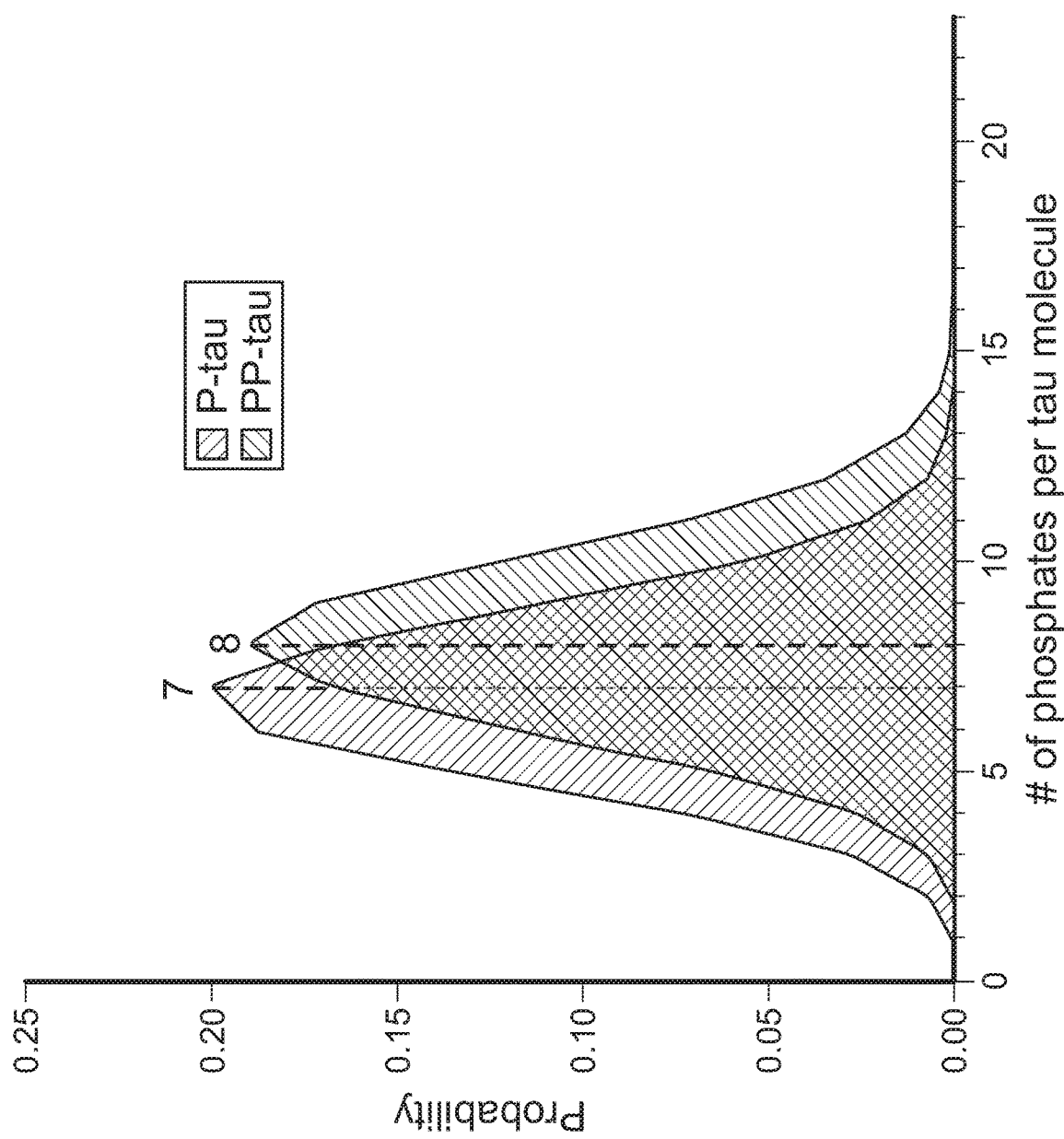
FIG. 4C is a graph showing frequency distribution of a particular number of phosphates per tau molecule being modified.

Individual site occupancies of the mapped phosphorylation sites were calculated using the equations listed in FIG. 4A, for each biological replicate separately. Negative values were transformed to zero and the average site occupancy across biological replicates was calculated (FIG. 4B). The sum of site occupancies of all modifications was used to infer the number of phosphates per tau molecule. Next a recursive approach was used to calculate the polynomial probability distribution of observing a specific number of phosphorylations per tau molecule (FIG. 4C). The input data consisted of site occupancies $X_{ij}$ for a total number of N=17 sites for each biological replicate (P-tau and PP-tau, three replicates each). The probability $p_j$ of a site j (j=1, 2, . . . , N) being modified from a total of r=3 replicates (i=1, 2, 3) was calculated as $$p_j = \frac{1}{r}\sum_{i=1}^{r} X_{ij}$$

Given D={$p_1$, $p_2$, . . . , $p_N$} the entire list of probability values for all N sites, $P(1|p_m)=p_m$ the probability of observing site m in a particular tau species, and $P(0|p_m)=1-p_m$, the probability of not observing site m, the probability of seeing k sites to be modified in that particular species out of all N sites was calculated as $P(k|D)=p_1(k-1)|D-p_1)+(1-p_1)*P(k|D-p_1)$ With $P(0|D)=\Pi_{i=1}^{17}(1-Pi)$ being the probability of observing 0 sites.

Results

Quantitative SRM FLEXiTau Assay Development

An SRM workflow was developed for the unbiased quantification of the modification extent of tau protein. This approach utilizes a stable isotope-labeled ('heavy') full-length tau protein standard that is added to any biological specimen prior to sample processing and MS analysis (FIG. 1A). The heavy tau standard was generated by cloning the longest tau isoform (4R2N) into the FLEX-vector, introducing an N-terminal artificial tag to the protein that is later used for standard purification as well as for absolute quantification of the endogenous tau. Heavy tau protein was expressed in a cell free expression system in the presence of isotopically labeled aspartic acid, lysine and arginine. The triple labeling strategy can minimize co-expressed light tau standard that could lead to a bias in quantification of endogenous tau.

In some embodiments of methods disclosed herein, the tau standard is then purified and added to the unlabeled endogenous ('light') sample, which is digested using trypsin or other proteolytic enzymes (FIG. 1A). Notably, due to the mixing of light and heavy species early in the sample processing, quantification errors that might arise due to sample loss and technical variability of sample preparation are minimized. The digested peptide mixture, containing light and heavy tau peptides species is then analyzed by mass spectrometry. All observed tau peptides should be present as pairs, featuring the light and the heavy isotopologues. The light-to-heavy (L/H) ratio of unmodified peptides reflects the initial mixing ratio. In the case of a modified endogenous peptide, the modification adds a mass shift to the light peptide mass and reduces the amount of unmodified peptide relative to heavy. Thus, any deviation of the L/H ratio thus indicates that this particular peptide is modified. The extent of modification is calculated as the difference in L/H ratio of its unmodified counterpart to the mixing ratio. Plotting the L/H ratio of all peptides sorted from N- to C terminal results in an intuitive representation of the PTM landscape across tau protein, where individual modifications as well as modified peptide regions can be quantitatively inferred (FIG. 1B).

The quality of the data depends on the sensitive and reproducible MS-based detection of the unmodified peptide species. To ensure this, a targeted assay specifically tailored to monitor the unmodified tau using SRM was devised. A step in developing SRM assays is the identification of the most sensitive and selective transitions (pair of peptide and their fragment ion masses).

A spectral library was created in order to find suitable transitions. To this end, high-resolution liquid chromatography tandem mass spectrometry (LC-MS/MS) of purified, digested tau standard was performed and it generated a collection of experimentally detected peptides and their fragment ions (FIG. 1C). To maximize the sequence coverage of tau, the tau standard was digested by trypsin and LysC. Collectively the spectral library peptides covered 84.6% of tau sequence.

The spectral library was then used to develop a quantitative SRM assay for these peptides, choosing the transitions with highest intensity without interfering signals. The sensitivity of the SRM method can be maximized by acquisition of the transitions in a small retention time window (termed scheduled SRM). Therefore, a scheduled 30 min LC-SRM method was developed. This method is suitable for pure/low complex tau samples and enables tau modification profile quantification from pure/low complex tau samples in a sensitive and time efficient manner.

When analyzing high concentrations of purified trypsin-digested standard using the developed SRM assay, a sequence coverage of 71% (23 peptides) was achieved reproducibly, and the 5 complementary LysC peptides increased this number to 75.3% (FIG. 1D). Notably, for the analysis of highly complex samples, longer gradient should be used in order to maintain specificity and minimize interfering background signals. iRT values for all transitions are provided, which can be used for quick and accurate retention time calculation.

Figure 2B:
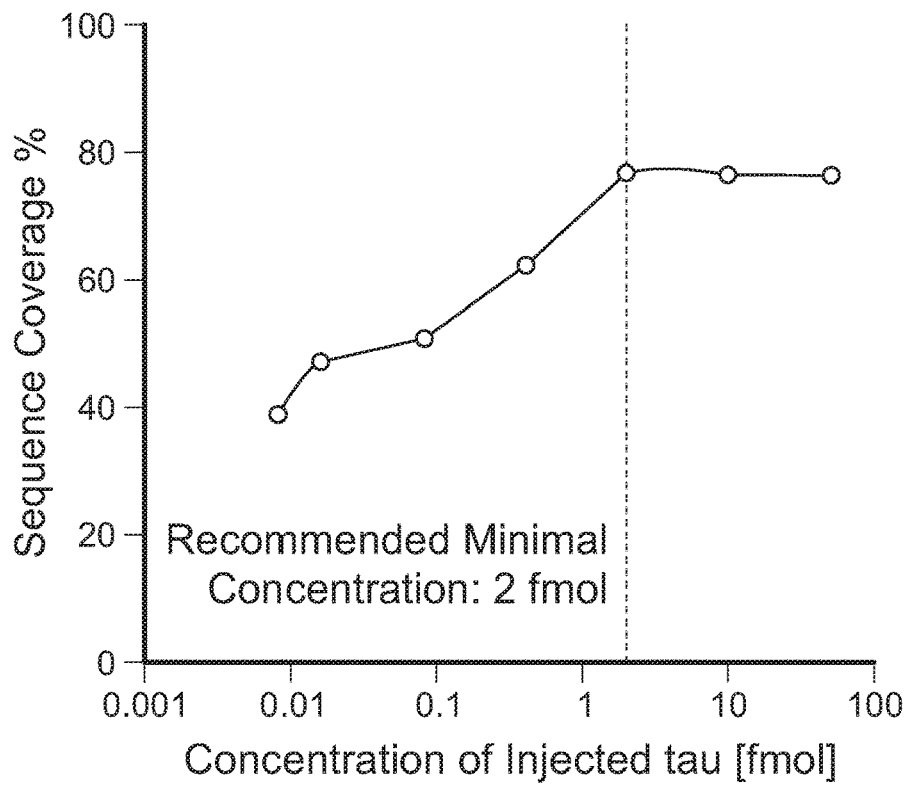
FIG. 2B is a graph showing the sequence coverage of tau relative to injection amount for one exemplary method described in this disclosure.
Figure 2C:
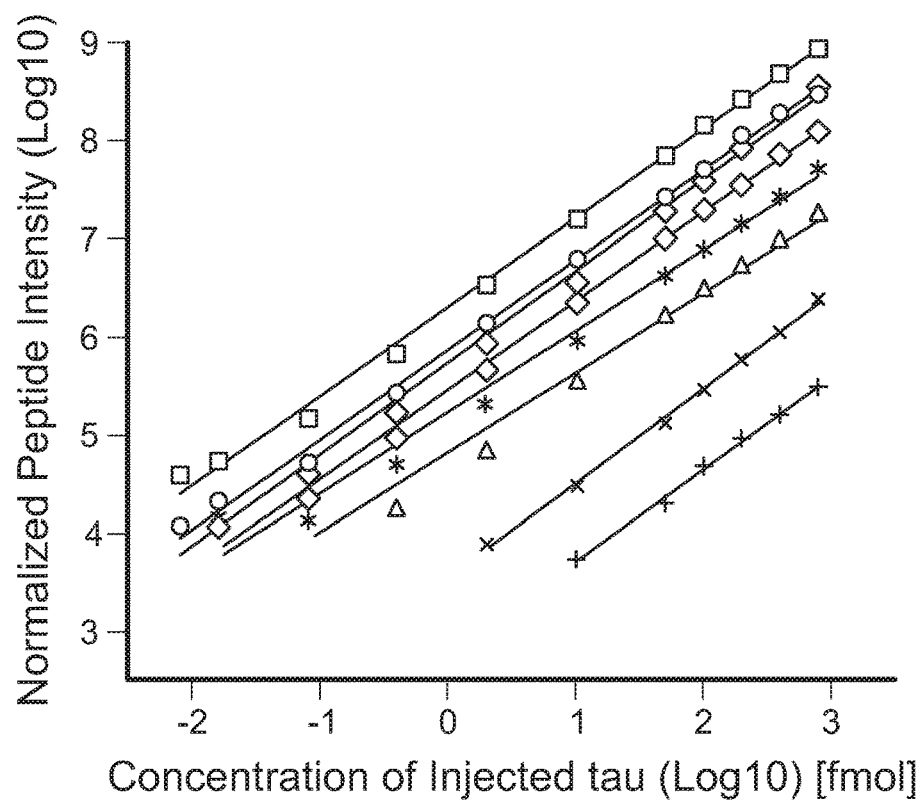
FIG. 2C is a graph showing different intensity ranges of 8 representative peptides by using one exemplary method described in this disclosure.

The methods described herein provide good coverage of tau down to attomolar concentrations. To determine the detection limit of the assay and the concentration dependency of the sequence coverage, a dilution series of digested heavy tau standard from 800 fmol to 8 amol in 11 dilution steps was prepared. The FLEX peptide was used as described previously to determine initial tau concentrations. These samples were measured in triplicate using the developed scheduled SRM assay and the signal intensities of the heavy peptides were monitored. In FIG. 2A, Log 2 peptide abundances (mean value of triplicate measurement) are shown as a heat map for the quantified peptides, sorted from N- to C-terminus. For maximal sequence coverage, at least 2 fmol of tau is injected. Amounts below that led to a decrease in sequence coverage. FIG. 2B shows achieved sequence coverage of tau relative to injection amount. In FIG. 2B, minimal concentration for maximum sequence coverage is indicated by dotted line. At 80 amol, a sequence coverage of 51% (25 quantifiable peptides) was measured. At the lowest end of the dilution series, 8 amol, the sequence coverage was 38.7% with 15 quantifiable peptides (FIG. 2B). The peptide quantification was linear over the range of the dilution series for most peptides, with some deviating from linearity at the lower and/or higher end. The average R2 value for the peptides assayed in the dilution curve experiment was 0.97. In the concentration range with highest linearity (0.4 to 400 fmol injected on column), a $R^2$ value of >0.98 was observed for approx. 90% of the targeted peptides. FIG. 2C shows representative curves of 8 peptides covering different intensity ranges.

In summary, the sensitivity of our assay is highlighted by the successful quantification of peptides across 5 orders of magnitude, down to 8 amol of injected tau. To achieve maximum sequence coverage and linearity of quantification, a working range between 2 and 400 fmol of tau is required. It is noteworthy that in biological settings a significant number of peptides will likely be modified, potentially to a very high extent, leading to a strong decrease in light peptide abundance and thus an increase in absolute ratio of light and heavy. Given these data, aiming for the higher end of this range (100-400 fmol) will ensure a highly reproducible quantification of light and heavy species for all peptides, independent of their modification extent. It is worth noting that the optimal working range and reproducibility of the assay can be affected by interfering signals and should be reassessed in each individual sample background, particularly in highly complex samples.

Assessing Analytical Precision of FLEXiTau

To evaluate the assay, the insect Sf9 cell system that offers a reproducible method of preparing human tau protein via baculovirus transfection was utilized. This is an in vitro model system, where the modifications present are well-defined. Tau expressed in these cells show multiple phosphorylation sites with a similar phosphorylation patterns to PHF tau from AD (51). The system has been used to study tau aggregation (36) and sequential phosphorylation by multiple kinases (52).

Four different species were analyzed: (i) tau from untreated Sf9 cells, phosphorylated at a native level (hereafter termed P-tau), (ii) tau from Sf9 cells treated with a phosphatase inhibitor (okadaic acid, OA), resulting in an increased level of phosphorylation (PP-tau), (iii) tau purified from Sf9 cells subsequently treated with alkaline phosphatase (AP) to remove the phosphorylations (deP-tau), and (iv) tau expressed in *E. coli* as unmodified control (ctrl-tau) (FIG. 3A). The detail is shown in FIG. 3A. Sf9 insect cells were transfected with recombinant baculovirus encoding for human 2N4R wild type tau. Purified Sf9 tau (P-tau) was treated with OA to generate dephosphorylated Sf9 tau (deP-tau). Phosphatase inhibition of prior to cell harvest and tau purification gives rise to hyperphosphorylated Sf9 (PP-tau). As control, unmodified tau was expressed in *E. coli*. 3 independent preparations of each species were subjected to the FLEXiTau workflow and each sample was analyzed for 3 times.

To ensure a high level of precision in peptide quantification, the data were manually curated. For modified species (P-tau and PP-tau), L/H ratios were normalized by the average of the 3 highest L/H ratios among all peptides for each individual sample, and for control species normalization was performed using all ratios above the median ratio. The same normalization factor was used for the LysC sample as calculated for the trypsin-digested sample. Using the criteria described, all 28 targeted peptides in all samples were quantified achieving a sequence coverage of 75%.

First, the quantification precision of technical replicates (replicate injections) and biological replicates (different Sf9 cell batches) were assessed. To assess reproducibility on technical and biological level, three independent preparations of each Sf9 tau species were subjected to FLEXiTau SRM analysis (three SRM measurements each). Unmodified peptide fraction (normalized L/H ratio) was extracted for each peptide and the averages of these values were taken for the three technical replicates and % CV calculated (left panel; "Technical replicates"). In FIG. 3B, the average of these values was then taken and % CV calculated for each species (right panel, "Biological replicates"). Data is represented in a boxplot (5%-95% whiskers, mean indicated by +). On average, the median coefficient of variation (CV) across replicate injections was 3.9% (FIG. 3B). Ctrl-tau presented the lowest (3%), and PP-tau the highest variability (5.2%). The vast majority of peptides (90%) showed a % CV below 10%. The biological variability was higher than the technical variability, with an average median % CV of 13.2% (3.5 fold compared to CV of technical replicates). Again, ctrl-tau presented the lowest variability (median % CV of 8.2%). In comparison to the technical variability, apart from the increase in median % CV, a broadening of the CV distribution was observed. On average, 74% of all peptides presented with a % CV below 20% (for the control tau species, more than 90% of peptides).

These results were compared using peptide intensities only (peak area) as a means of quantification, opposed to the FLEXitau quantification using the internal standard. To this end, light peak areas for all monitored peptides in the same dataset was extracted. Compared to the FLEXiTau quantification, quantification using peak area intensity results in an approx. 4 fold increase in technical variability (from 3.9% to 15.3%) and 2 fold increase in biological variability (from 13.2% to 25.3%). This corroborates that the employment of the internal standard is highly beneficial to the precision and reproducibility of the analyzed samples.

Quantitative PTM Profiling of Hyperphosphorylated Tau

Figures 3C, 3D:
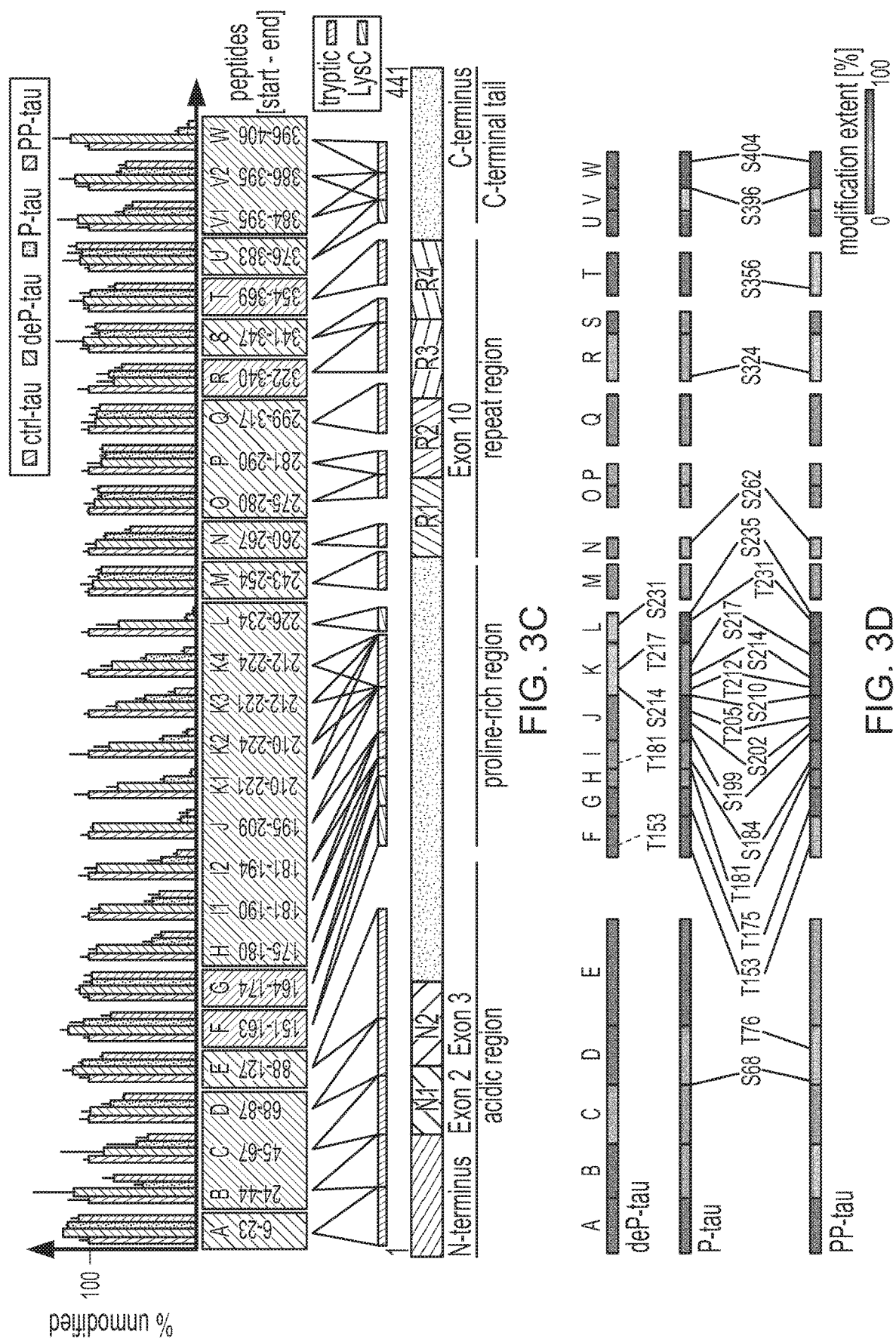
FIG. 3C is a schematic diagram showing each tau species (normalized L/H ratios) as determined by one exemplary methods described herein for each quantified peptide sorted from N- to C-terminus.
FIG. 3D is a schematic diagram showing phosphorylated sites identified by one exemplary method as described in this disclosure.

The relative peptide modification extent of the Sf9 hyperphosphorylated species in comparison to ctrl-tau was analyzed. FIG. 3C shows the quantification of unmodified tau peptides in the global FLEXiTau representation (see also FIG. 1C). Peptides were defined as 'modified' if the average of the biological replicates resulted in a value below 100% and were significantly different from vs. ctrl-tau (student t-test, p<0.05). In FIG. 3C, each tau species (normalized L/H ratios) for each quantified peptide sorted from N- to C-terminus is shown. Peptides are projected onto a schematic of 2N4R tau protein, respective to their amino acid location. Exons prone to splicing (exon 2, 3 and 10) are depicted.

Table 1 lists all quantified peptides and their respective modification extent, including the significance value. On average (mean value of all modified peptides), the modification extent of PP-tau was 25% higher compared to P-tau (34.1% for PP-tau, compared to 42.4% for P-tau). 7 peptides (39% of the quantified sequence) appeared to be unmodified in both species, while the remaining 21 peptides (nearly half of the quantified sequence) were found to be modified in either P-tau or PP-tau. From these, the vast majority was modified both in P-tau and PP-tau. Only 3 peptides (peptides F, R and T) were modified in PP-tau, but not P-tau, suggesting that phosphorylation sites in these regions are more accessible to phosphatases, which are inhibited by okadaic acid ($_{151}$IATPRGAAPPGQK$_{163}$ (SEQ ID NO: 20), $_{322}$CGSLGNIHHKPGGGQVEVK$_{340}$ (SEQ ID NO: 29), and $_{354}$IGSLDNITHVPGGGNK$_{369}$ (SEQ ID NO: 14)).

In Table 1, peptides detected are shown with their sequence ordered by their amino acid location in tau (N- to C-terminal). Peptide modification extent was determined by the difference of normalized L/H ratio to ctrl-tau, where 100% represents a peptide that is fully modified (no unmodified peptide detected). P-values were calculated in comparison to control tau (student t-test). Corresponding phosphorylation sites detected by complementary LC-MS/MS analysis are shown. Note that a modification site on the first amino acid after the cleavage site will contribute to the previous (N-terminal) peptide as well and will be listed twice (e.g. T175).

To gain a more functional view of the data, peptides were grouped into their corresponding tau domains, from N- to C-terminal: acidic region, proline-rich region, repeat region, and C-terminal tail. The data indicated that each tau domain presented with a characteristic modification extent (and this trend was maintained upon treatment with phosphatase inhibitor). The repeat region was the least modified with an average modification extent of 10.1% and 14.8% for P-tau and PP-tau, respectively; most of the peptides in this region were unmodified (student t-test, p>0.05, see above). The acidic region and c-terminal tail showed moderate modification extents (acidic region: 23.1% and 24.5% and c-terminal tail: 48.9% and 55.9%, for P-tau and PP-tau, respectively). The proline rich region depicted the highest modification extent (on average 55.2% and 71.0% for P-tau and PP-tau, respectively). This region harbored the peptide with the highest modification extent of all peptides, with 90.6% in P-tau and 97.2% in PP-tau (peptide L, $_{226}$VAVVRTPPK$_{234}$ (SEQ ID NO: 20)) (FIG. 3C and Table 1).

The dephosphorylated Sf9 tau species deP-tau appeared to contain residual phosphorylation, mostly located in the proline-rich region. The highest modification extent was observed on peptide K and L ($_{210}$SRTPSLPTPPTR$_{221}$ (SEQ ID NO: 24) and $_{226}$VAVVRTPPK$_{234}$ (SEQ ID NO: 26)), both 27%.

Complementation of FLEXiTau with LC-MS/MS Data Results in a Quantitative PTM Map The FLEXiTau experiments revealed absolute modification extent of tau peptides as well as relative differences between P-tau and PP-tau. These findings were validated by identifying the modifications present on these peptides. To this end, the same samples to LC-MS/MS analysis and mapped the identified PTMs to their corresponding peptides (FIG. 3D and Table 1) were submitted. FIG. 3D shows Phosphorylated sites identified by LCMS/MS shotgun analysis were mapped onto tau peptides color coded according to their modification extent as quantified by the SRM analysis (1−L/H ratio).

In total, 21 phosphorylation sites were identified, 12 serine and 7 threonine phosphorylation sites on the Sf9 P-tau and 2 additional phosphorylation sites were identified for PP-tau only (2×S). Consistent with the FLEXiTau data, the proline-rich domain depicted the highest density of phosphorylation sites with up to 4 detected sites per peptide (13 sites total, both P-tau and PP-tau). A comprehensive list of detected modified peptide species can be found in Table 2.

20 out of the 21 peptides that were determined as modified (in both P-tau and PP-tau) in the FLEXiTau experiment could be verified by the presence of one or more phosphorylation site. Only for peptide B ($_{24}$KDQGGYTMQDQEGDTDAGLK$_{44}$ (SEQ ID NO: 19)) no corresponding modification could be identified. In this case, FLEXiTau analysis showed a significant modification extent in both P-tau and PP-tau (51%, p=0.008 and 22%, p=0.046, respectively), clearly indicating the presence of a modification. For the 3 peptides exclusively modified in PP-tau, but not on P-tau phosphorylation sites were identified on T153, S324 and S356. Unexpectedly, T153 and S324 were not only found in PP-tau but also on P-tau. However, the quantitative FLEXiTau data showed that the extent of modification of these peptides in P-tau is minimal (4.2% and 12.4%, respectively; p-value across biological replicates non-significant). Corroborating the quantitative FLEXiTau data, no PTM on peptides that were measured as unmodified by FLEXiTau were found. The only exception is the peptide $_{164}$GQANATRIPAK$_{174}$ (SEQ ID NO: 21), on which T175 was detected as being phosphorylated both in P-tau and PP-tau. However, the FLEXiTau data suggested that the modification extent is very low (<3% for both species), which is below the precision of the assay (% CV=3.9%, see above).

In summary, these findings show that the FLEXiTau and LC-MS/MS datasets are complementary. FLEXiTau adds quantitative information to the well-established qualitative DDA approaches, resulting in a quantitative PTM map. In addition, FLEXiTau can point towards potential novel (e.g. un-described) sites when no matching modification is found.

In one special case, FLEXiTau suggested an additional PTM, although a matching modification was identified. Peptide C ($_{45}$ESPLQTPTEDGSEEPGSETSDAK$_{67}$ (SEQ ID NO: 3)) presented with a modification extent of 44.7% (P-tau) and 54.0% (PP-tau), and S68 was identified as responsible modification (located right after the cleavage site a phosphorylation leads to a miscleavage, in turn leading to a drop in L/H ratio). Notably, its modification extent is higher than the one from its C-terminal neighbor, peptide D ($_{68}$STPTAEDVTAPLVDEGAPGK$_{87}$ (SEQ ID NO: 4)), although the latter shares this sites plus an additional one. This led to the speculation that peptide C harbored an additional modification site that was not detected by our LCMS/MS analysis, to account for the 'unexplained' higher modification extent.

In the case of peptides with missing modifications (e.g. here peptides B and C), it is speculated that an optimization of LC-MS/MS analysis is required for a successful detection of the corresponding modified species (e.g. phospho-peptide enrichment). Despite the vast amount of information, in this region only one site has been previously described in vivo. Other putative phosphorylation sites in this region are Y29 and T39 (peptide B) and T50, T52 and S56 (peptide C).

Using FLEXiTau for the Calculation of Site Occupancy

FLEXiTau was used to determine modification extent on peptide level, and qualitative LC-MS/MS data was acquired to match the quantitative FLEXiTau data. Next these two complementary datasets were combined to infer site-specific modification extents, e.g. site occupancy. For peptides harboring a single modification, the peptide modification extent directly reflects on the occupancy of that modified site. Notably this only holds true under the premise that no modification other than the one detected is present on the respective peptide. In this dataset, this direct approach applies to T175, S262, S324, S356, and S416/422. However, for many peptides, multiple phosphorylated sites were identified (in particular in the proline-rich region, as well as in the C-terminal tail). In these cases, the direct correlation of peptide modification extent and site occupancy is constrained. Each site may contribute to varying degrees to the overall peptide modification extent. Thus, for multiply modified peptides, the peptide modification extent equals to the sum of all individual site occupancies, and site-specific stoichiometries cannot be directly inferred.

To overcome this constraint, a combinatorial strategy was developed to use information of 'overlapping' peptides, to deduce quantitation of single sites even when multiple modifications are present (for a schematic, see FIG. 4A). Referring to FIG. 4A, for peptides containing a single modification site, the site occupancy equals the peptide modification extent calculated by the FLEXiTau assay. For multiply modified peptides, a combinatorial approach was designed to stepwise calculate individual site occupancies by using quantitative information from overlapping peptides. (i) the proline-rich region; equations 1-9, with equation 1 starting from N-terminus and equation 5 starting from the C-terminus. (ii) the C-terminal tail; equations 10-11.

Overlapping peptides are produced by a missed tryptic cleavage which is typically is caused by closely located lysines and arginines (see peptides I1/I2, K1-K4, and V1/V2). In these cases, the primary tryptic peptide has a miscleaved counterpart whose sequence equals the nonmiscleaved primary peptide species plus a short amino acid sequence until the following cleavage site. In addition, a missed cleavage can also occur if a phosphorylation is present on the amino acid in the first position after the cleavage site (see peptides G/H, I2/J, J/K, and V2/W). In these cases, cleavage is impaired due to steric hindrance by the phosphate group. Although strictly speaking the modification is located on the second peptide, due to the phosphorylation-induced miscleavage it contributes to the modification extent of the first peptide as well.

Starting with a peptide with a single modification (thus with known stoichiometry), the stoichiometry of additional sites was stepwise inferred by using the quantitative information of the subsequent 'overlapping' peptide. For example, in the case of the proline-rich region, this method started with peptide G in the N-terminal periphery. Its modification extent equals the occupancy of its single phosphorylation site on residue T175. The adjacent overlapping peptide (peptide H) contained two detected phosphorylations, T175 as well as T181. Here, the modification extent of T181 equals the difference of modification extent of peptide G (T175) to peptide H (T181+T175), in this case 56.3% (P-tau) and 64.4% (PP-tau). This combinatorial strategy can successfully quantify the individual stoichiometry of sites T181, S184, S210, S396 and S404. A summary of site occupancies for all phosphorylations detected in P-tau and PP-tau is depicted in FIG. 4B (see also Table 3). In FIG. 4B, phosphorylation extents for all identified sites are shown in %. Sites are sorted by the amino acid location in the tau sequence N- to C terminus. The boxes indicate the highly modified region (i) and (ii) shown in FIG. 4A.

When the total modification extent of a peptide was higher than the sum of its quantified single components, it is speculated that the remaining value corresponds to an additional modification that has not been identified in the LC-MS/MS experiments. For example, the modification extent of miscleaved peptide $_{181}$TPPSSGEPPKSGDR$_{195}$ (SEQ ID NO: 23) compared to its non-miscleaved counterpart indicated the existence of an unmapped modification event (7.3% and 16.3% in P-tau and PP-tau, respectively) in addition to the detected and quantified sites T181 and S184. This missing phosphorylation was tentatively assigned to serine S195, a site that was reported previously by antibody staining as well as mass spectrometry approaches.

In summary, FLEXiTau complemented with LC-MS/MS data enables the quantification of stoichiometries of individual phosphorylation sites. The completeness of this data can infer several characteristics that can be used to compare tau species from each other. The sum of all individual site occupancies of phosphorylations across tau (including unmapped, hypothetical ones) provides a measure for the average number of phosphates per tau molecule. In the experiment, P-tau carried 4.9 phosphates per tau molecule, whereas PP-tau carried 6.1 phosphates. While it has been reported that Sf9 P-tau and PP-tau carry up to 12 and 20 phosphates per tau molecules, respectively, the result shows that there is a heterogeneous population. While the total number of phosphorylation sites were identified to be up to 23, the average number of phosphates per molecule is determined to be 5 and 6, respectively. In comparison, adult soluble cytosolic tau has been estimated to carry ~2-3 phosphates per molecule, whereas tau from PHFs of AD brains is 3-4 fold higher phosphorylated. This is in agreement with the data, showing that Sf9 tau species are more phosphorylated than cytosolic tau, with PP-tau nearly reaching the phosphorylation extent of AD-tau. Furthermore, the average site occupancy was 29.5% (P-tau) and 35.7% (PP-tau). As expected, these values are lower than the peptide modification extent (34.1% and 42.4%, P-tau and PP-tau respectively), as there are peptides containing several sites. Lastly, all site occupancies were used to calculate the probability distribution of observing a specific number of phosphates per molecule in each species. The resulting distributions for P-tau and PP-tau show that both species are similar to each other regarding the number of possible phosphorylation states, as indicated by similar broadness of the distribution (Full width at half maximum (FWHM) of 3.8 and 3.9, P-tau and PP-tau, respectively) (FIG. 4C). In FIG. 4C, frequency distribution of a particular number of phosphates per tau molecule being modified. Maximum likelihood estimate is indicated by vertical line. P, phosphate groups. As expected, a shift of the distribution of PP-tau towards to a higher phosphorylation state by 1 phosphate, compared to P-tau (maximum likelihood of 6 phosphates per tau molecule, compared to 5, for PP-tau and P-tau, respectively). As a result, approx. 60% of PP-tau molecules are expected to contain 6 phosphates or more, while it is 40% for P-tau. Notably, this probability estimation does not take into account site crosstalk or dependencies between specific phosphorylation sites. If such data is available, it should be incorporated into this calculation, as this will provide additional accuracy for the distribution estimation.

Example 2: Quantifying the Extent of Tau PTMs in Human Disease

Experiments were performed to quantify the extent of Tau PTMs in human samples using appropriate methods as described in Example 1. For applications in a number of different biological settings, its applicability to complex, disease-related samples is crucial. Recent studies suggest that Sf9 tau has similar characteristics to tau isolated from AD brain, as shown by diagnostic AD antibodies as well as MALDI-MS analysis and it has been used as a cellular model for pathological tau in various studies. This prompted testing the assay on tau aggregates derived from AD patient brains and to compare this quantitative data to the earlier results of Sf9 tau, thus evaluating the Sf9 tau species as a model proxy for disease tau.

Figure 5A:
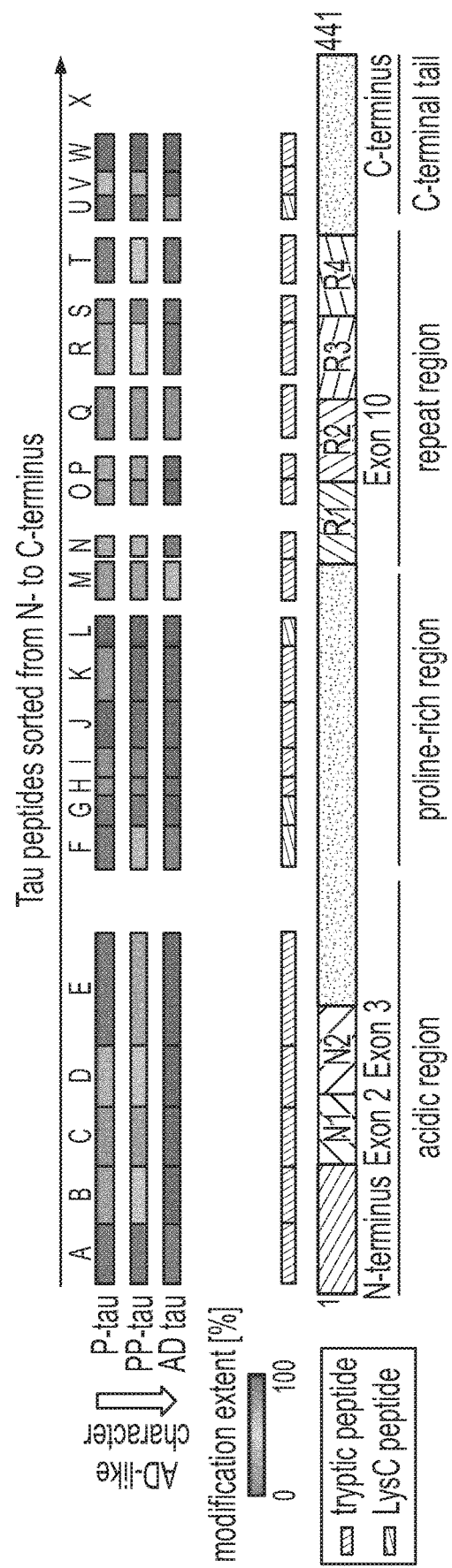
FIG. 5A is a schematic diagram showing quantified peptides for insoluble PHF-tau preparations from three different AD brains.

To enrich for insoluble pathological tau species, tau fibrils from post-mortem cortical brain tissue derived from three individual AD patients (AD-tau) were extracted and they were subjected to the FLEXiTau workflow. A comparison of the acquired quantitative data to P-tau and PP-tau is presented in FIG. 5A. In FIG. 5A, three independent preparations of insoluble PHF-tau preparations from three different AD brains were subjected to the FLEXiTau workflow (triplicate SRM measurements). The modification extent of each peptide was calculated as 1−L/H ratio. Quantified peptides are shown from N- to C-terminus, in-scale mapped to a schematic tau protein.

The overall modification extent was more than twofold in AD-tau compared to Sf9 model tau (AD-tau 77.2%, compared to 34.1% in P-tau and 42.4% PP-tau, respectively). Overall, most of the peptides that were found as unmodified in both P-tau and PP-tau were highly modified in AD-tau (6 out of 7 peptides). Interestingly, 2 out of the 3 peptides that were exclusively modified in PP-tau were found to be unmodified in AD-tau. In summary this resulted in a total of 3 peptides unmodified peptides in AD-tau. Notably these peptides (peptides R, S, and T) were all adjacent to each other, located in the repeat region ($_{322}$CGSLGNIHHKPGGGQVEVK$_{340}$ (SEQ ID NO: 29), $_{341}$SEKLDFK$_{347}$ (SEQ ID NO: 30) and $_{354}$IGSLDNITHVPGGGNK$_{369}$ (SEQ ID NO: 14)). Compared to Sf9 model tau, the acidic region as well as the C-terminal tail showed the highest difference in modification extent.

To systematically assess these quantitative differences in modification extent between Sf9 tau and ADTau, a hierarchical cluster analysis was performed for the FLEXiTau data (Euclidean Distance, Ward criteria). This analysis grouped the peptides into 6 distinct classes (I-VI, FIG. 5B). In FIG. 5B, peptides were sorted into categories using hierarchical clustering (Euclidean distance, Ward's criteria). Modifications reported on AD tau are listed next to the corresponding peptide. P, phosphorylation; grey, low confidence site; ub, ubiquitination, ac, acetylation, bold, modifications detected in Sf9 tau species.

Class I and II peptides (each 12.5%, 3 peptides) contained peptides with no or little modification extent, with class I showing none at all and class II showing minor modification in AD-tau. Class III and IV peptides (each 20.8%, 5 peptides) showed high modification extent in AD, while Sf9 tau was not (class III) or little (class IV) modified. Finally, class V and VI peptides were highly modified in all three species, whereas class V contained peptides that showed enhanced modification in AD tau (20.8%, 5 peptides), and class VI peptides were modified to similar extent in all species (12.5%, 3 peptides). In summary, one third of the quantified peptides (31% of tau sequence analyzed) were modified to similar extent in AD-tau as the Sf9 species, while the remaining two thirds of the peptides showed significantly higher modification extent in AD tau.

The PTMs of PHF-tau from AD brain has been extensively studied using different types of enrichment strategies and reviewed here. To investigate the quantitative differences between AD-tau and Sf9 in a complete, precise manner, all reported modifications were mapped to the peptides from FLEXiTau dataset (FIG. 5B, right panel). The references shown in FIG. 5B are (a) Cripps, D., Thomas, S. N., Jeng, Y., Yang, F., Davies, P., and Yang, A. J. (2006) Alzheimer disease-specific conformation of hyperphosphorylated paired helical filament-Tau is polyubiquitinated through Lys-48, Lys-11, and Lys-6 ubiquitin conjugation. The Journal of biological chemistry 281, 10825-10838; (b) Hanger, D. P., Byers, H. L., Wray, S., Leung, K.-Y., Saxton, M. J., Seereeram, A., Reynolds, C. H., Ward, M. A., and Anderton, B. H. (2007) Novel phosphorylation sites in tau from Alzheimer brain support a role for casein kinase 1 in disease pathogenesis. The Journal of biological chemistry 282, 23645-23654; (c) Cohen, T. J., Guo, J. L., Hurtado, D. E., Kwong, L. K., Mills, I. P., Trojanowski, J. Q., and Lee, V. M. Y. (2011) The acetylation of tau inhibits its function and promotes pathological tau aggregation. Nature Communications 2, 252; (d) Martin, L., Latypova, X., and Terro, F. (2011) Post-translational modifications of tau protein: implications for Alzheimer's disease. Neurochemistry International 58, 458-471; (e) Thomas, S. N., Funk, K. E., Wan, Y., Liao, Z., Davies, P., Kuret, J., and Yang, A. J. (2012) Dual modification of Alzheimer's disease PHF-tau protein by lysine methylation and ubiquitylation: a mass spectrometry approach. Acta Neuropathologica 123, 105-117; (f) Noble, W., Hanger, D. P., Miller, C. C. J., and Lovestone, S. (2013) The importance of tau phosphorylation for neurodegenerative diseases. Frontiers in Neurology 4, 83; (g) Grinberg, L. T., Wang, X., Wang, C., Sohn, P. D., Theofilas, P., Sidhu, M., Arevalo, J. B., Heinsen, H., Huang, E. J., Rosen, H., Miller, B. L., Gan, L., and Seeley, W. W. (2013) Argyrophilic grain disease differs from other tauopathies by lacking tau acetylation. Acta neuropathologica 125, 581-593; (h) Dammer, E. B., Lee, A. K., Duong, D. M., Gearing, M., Lah, J. J., Levey, A. I., and Seyfried, N. T. (2015) Quantitative phosphoproteomics of Alzheimer's disease reveals cross-talk between kinases and small heat shock proteins. Proteomics 15, 508-519.

Most of the differences of AD-tau to Sf9 tau could be explained by additional modifications on the respective peptide. The peptides that reflected the biggest changes between Sf9 tau and AD tau (class III and class IV peptides) harbor multiple additional phosphorylations and acetylation sites (such as Ac-K274 and Ac-K280), highlighting the importance of analyzing modifications other than phosphorylation when studying tau aggregation. Interestingly, all ubiquitinylation sites reported so far are located on peptides that contain few other modifications and show little modification extent (class I and II peptides). This suggests that ubiquitinylation occurs at very low stoichiometries, consistent with a previous study that used semi-quantitative spectral counting approach to infer the amount of ubiquitinylated compared to unmodified species. Furthermore, peptides with high similarity between AD-tau and Sf9 tau (class V and VI) exclusively harbored phosphorylation (and no other type of modification). With few exceptions, most of these phosphorylation sites were detected in both Sf9 and AD-tau. Notably, the epitopes of the most commonly used AD diagnostic antibodies are located on these peptides. This finding corroborates the notion that the hyperphosphorylated species represents an accurate model for AD-specific phosphorylation sites particularly when studying hyperphosphorylated regions such as the proline-rich domain.

Overall the data shows that the performance of the assay is uncompromised by the heterogeneity and number of tau modifications. FLEXiTau was validated by an application to highly modified tau expressed in Sf9 insect cells, a cellular system that generates tau in a distinct, exceptionally high phosphorylated state (Tepper, K., Biernat, J., Kumar, S., Wegmann, S., Timm, T., Hubschmann, S., Redecke, L., Mandelkow, E. M., Muller, D. J., and Mandelkow, E. (2014) Oligomer formation of tau protein hyperphosphorylated in cells. J Biol Chem 289, 34389-34407). FLEXiTau was used to measure the precise phosphorylation state of various hyperphosphorylated tau species derived from these Sf9 cells. Complementing the quantitative peptide information with LC-MS/MS data about the phosphorylations present, the present disclosure maps and quantifies over 20 phosphorylations in a site-specific manner, even for peptides that harbor multiple modifications.

This example provides methods for diagnostic purposes, and demonstrated the versatility of the assay by employing the workflow to tau aggregates derived from post-mortem AD brain tissue. This result demonstrates that FLEXiTau is applicable to samples of varying complexity and is uncompromised by the extent or heterogeneity of modifications. Furthermore, a comparative analysis to the Sf9 cells allowed for a precise assessment of the Sf9 tau species as a disease proxy.

Overall the work presented here shows that FLEXiTau is a versatile, useful tool to assess tau PTMs in an accurate, precise manner. The assay, for the first time, provides a global, 'complete' picture of the PTM landscape. The absolute quantitative 'PTM signature' can be used to determine relative changes between different tau species in a very precise manner. The quantitative data obtained suggests the presence of modifications that can then be complemented qualitatively using traditional LC-MS/MS experiments. It can also be followed up using directed and targeted analysis, thus showing the versatility of the unbiased quantitation as a tool to identify novel, non-described modifications.

This example chose the longest tau isoform as the standard in the assay to specifically measure 2N4R expressed in Sf9 cells. However, FLEXiTau is not limited to the measurement of full-length tau and may be extended to other splice variants. Other assay variants can conveniently be designed to include alternate species (e.g. mouse tau). Given its precision and versatility, the application of this assay may be applied to a wide range of biological settings and questions. For instance, FLEXiTau will enable the evaluation of tau model systems and the assessment of their proximity to specific tauopathies. This will allow us to determine which mouse model is most reflective of a particular disease. With its ability to measure small changes in the PTM landscape, our assay could facilitate the screening of small compounds, as well as monitor and validate the progress of treatment. FLEXITau is currently being applied to study the clearance of tau aggregates in cell-based systems. This is especially important given the recent interest in tau-targeted therapeutic approaches since the failure of many amyloid-beta-targeted therapeutics in phase III clinical trials. Furthermore, recent insights point towards disease-specific modifications and FLEXiTau will help in determining tau profiles specific for each disease and disease progression state. Finally, offering both the necessary sensitivity and specificity, FLEXiTau has potential as in vivo diagnostic biomarker for tau derived from peripheral fluids such as CSF or blood, an effort that has been hampered so far by the lack of methods capable of dealing with the molecular heterogeneity and low abundance of tau present in CSF.

Example 3: Identifying Diagnostic Signatures for Neurodegenerative Tauopathies Experiments were performed to identify diagnostic signatures for neurodegenerative tauopathies.
Materials and Methods
Selection of Tauopathy Patients and Controls Human post-mortem brain specimens from patients with AD, PSP, PiD and CBD, and non-demented controls were obtained from 5 different brain banks: 1) the Neurodegenerative Disease Brain Bank (NDBB), Memory and Aging Center, University of California, San Francisco (UCSF), CA; 2) the University of Maryland Brain & Tissue Bank at the University of Maryland School of Medicine, Baltimore, Md.; 3) the Harvard Brain Tissue Resource Center, McLean Hospital, Harvard Medical School, Belmont, Mass.; 4) the University of Miami (UM) Brain Endowment Bank, Miller School of Medicine, Miami, Md.; 5) the Human Brain and Spinal Fluid Resource Center (HBSFRC), VA West Los Angeles Healthcare Center, Los Angeles, Calif. Tissue from brain banks 2) to 5) were acquired through the NIH NeuroBioBank (U.S. Department of Health and Human Services, National Institutes of Health). Pathological and clinical information, if available, was de-identified. Human brain tissue samples were obtained from the parietal cortex (Brodmann Area (BA) 39, angular gyrus). This area was selected due to the likelihood that it would be affected in all four diseases yet would be spared of comorbid AD-type pathology in PSP, PiD and CBD. In all cases, brain blocks of 1-4 g were dissected from frozen brain slabs and shipped to Boston Children's Hospital on dry ice. Demographic details of patients and control individuals are given in Table 4.
Preparation of Tissue Samples for MS While still frozen, 0.25-0.35 g sections of cortical brain specimens were lysed and clarified by centrifugation at 11,000×g for 30 min at 4° C. To obtain insoluble tau fractions, sarkosyl fractionation was performed. Briefly, lysates were treated with 1% sarkosyl for 60 min at 4° C. and ultracentrifuged at 100,000×g for 2 h at 4° C. The sarkosyl insoluble fraction was solubilized in 1% SDS and processed using the FLEXITau workflow in order to quantify absolute tau amounts and determine the level of tau modifications. Light FLEX-peptide is added in predetermined concentration to calculate absolute quantity of endogenous tau. The relative peptide abundance of light and heavy tau peptides can be used to infer modification extent of tau for each peptide. In brief, heavy tau was expressed in the presence of heavy isotope (i.e. $^{13}C$ and $^{15}N$) labeled lysine, arginine and aspartate and subsequently purified using Ni-Sepharose beads (Ni-Sepharose High Performance resin, GE Healthcare, Marlborough, Mass.). Purified heavy tau standard or sarkosyl insoluble tau fractions were diluted with 8 M urea and processed separately using filter-aided sample preparation (FASP) (FASP Protein Digestion Kit, Expedeon, San Diego, Calif.). Protein mixtures were digested with 12.5 ng/µl trypsin (sequencing grade modified trypsin, Promega, Madison, Wis.) overnight at 37° C. Acidified peptides were desalted using C18 extraction plates (Waters). Vacuum-dried peptides were reconstituted in sample buffer (5% formic acid, 5% acetonitrile (ACN)) containing indexed retention time (iRT) peptides (Biognosys, Schlieren/Zurich, Switzerland) and 50 fmol/µl non-labeled FLEX-peptide (TENLYFQGDISR, synthesized by Sigma Life Science, quantified via amino acid analysis of Molecular Biology Core Facilities, Dana Farber Cancer Institute, Boston, Mass.) (Escher C, Reiter L, MacLean B, et al. Using iRT, a normalized retention time for more targeted measurement of peptides. Proteomics 2012; 12(8): 1111-21). Heavy tau standard peptides were added to insoluble (light) tau peptides to achieve approximately a 1:1 ratio of Light-to-Heavy (L/H) tau.
LC-SRM Measurements and Data Analysis LC-SRM measurements of tau L/H peptide ratios were performed as described in early examples. The FLEXITau SRM assay was optimized for the analysis of post-mortem tissue, guided by an extensive list of validated transitions generated in-house through LC-MS/MS analysis of sarkosyl insoluble tau on a quadrupole Orbitrap tandem mass spectrometer (Q Exactive, Thermo Fisher Scientific, Waltham, Mass.). After optimization of the transition list, peptide mixtures were analyzed on a triple quadrupole mass spectrometer (5500 QTRAP, Sciex) using a micro-autosampler AS3 and a nanoflow UPLC pump (Eksigent, Dublin, Calif.; Sciex, Framingham, Mass.), using the trap-elute chip system (cHiPLC nanoflex, Eksigent, Dublin, Calif.). Briefly, peptides were first loaded onto the trap-chip (200 µm×75

ChromXP C18-CL 3 µm 120 A, Nano cHiPLC Eksigent, Dublin, Calif.) and then separated using a 120 min gradient from 95% buffer A (0.1% (v/v) formic acid in HPLC-$H_2O$) and 5% buffer B (0.2% (v/v) formic acid in ACN) to 35% buffer B on the analytical column-chip (75 µm×15 cm, ChromXP C18-CL 3 µm 120 A, Nano cHiPLC Eksigent, Dublin, Calif.). The retention time window was set to 5 min and total scan time to 1.2 s, which ensured a dwell time over 20 ms per transition. To avoid sample carry over, blanks were analyzed between every SRM run. To ensure no bias in acquisition, samples were run in randomized order (three technical replicates per sample). SRM data were analyzed and validated in Skyline (version 2.6, MacCoss Lab Software, University of Washington, Seattle, Wash.) (MacLean B, Tomazela D M, Shulman N, et al. Skyline: an open source document editor for creating and analyzing targeted proteomics experiments. Bioinformatics 2010; 26(7): 966-8). All peptide transitions were evaluated for variability, similarity between y-ion ratios, elution times, and interfering signals by manual analysis. Peak boundaries were manually inspected and reassigned as needed to ensure correct peak detection and accurate integration. Peptides were considered 'quantifiable' if the peptide transitions had a signal-to-noise of >3 and at least three light and three heavy high-quality SRM transitions were observed. Peptides were kept for further downstream analysis if quantifiable in every patient sample. The final peptide list consisted of 17 tau peptides. To compensate for differences in mixing ratio, samples were normalized by the L/H ratio of the least modified peptides. To this end, in each sample, the L/H ratio of peak intensities of each peptide was divided by the average of the three tau peptides with highest ratio in that particular sample. Absolute abundance of tau was calculated using the FLEX peptide L/H ratio as described in Singh S, Springer M, Steen J, Kirschner M W, Steen H. FLEXIQuant: a novel tool for the absolute quantification of proteins, and the simultaneous identification and quantification of potentially modified peptides. J Proteome Res 2009; 8(5): 2201-10. Amounts of insoluble tau in each patient samples was calculated in the unit of fmol tau per mg brain wet weight (average of 5 technical replicates).

Analytical Procedure

A computational classifier for each patient group was developed based on supervised machine learning. The input data consisted of normalized L/H peptide intensity ratios of each peptide measured by SRM, i.e. each sample was represented by a vector of 17 peptides (features). The use of absolute abundance as an 18th feature was examined, however results showed the performance of the classifier did not improve (see FIGS. 12A-12D). The inventors constructed a supervised machine learning model for each disease category using the following procedures (the workflow is summarized in FIG. 7): First, a binary dataset was created consisting of the case category of interest (e.g. AD) and the remaining reference category (e.g. a combination of all non-AD samples). Then, a recursive feature elimination method based on the Random Forest (RF) algorithm was used to select the feature set that provides optimal separation of the case category and reference category in the training dataset. Finally, the optimized RF classifier was evaluated using an independent testing dataset. This approach was repeated for each case category, i.e. also PSP, PiD, CBD, and ctrl.

The performance of the classifiers was assessed by accuracy (ac), defined as the total number of correctly classified cases (True Positives, TP, and True Negatives, TN) relative to the total number of cases in the testing set. Sensitivity (se) of the classifier was calculated as the number of TP divided by the total number of cases with given condition, that is TP and False Negatives (FN) (se=TP/(TP+FN)). Specificity was determined as the proportion of TN to the number of cases without given condition, that is TN plus False Positives (FP) (sp=TN/(TN+FP)). The performance (the positive diagnostic likelihood ratio) of a classifier, expressed by its true positive rate (TPR, or sensitivity), and false positive rate (FPR, or 1−specificity), was plotted in a receiver operator curve (ROC) space. The predictive power of each classifier was further assessed by calculating the area under the ROC curve (AUC; AUC: 0.9-1.0=excellent; 0.8-0.9=good; 0.7-0.8=fair; 0.6-0.7=poor; 0.5-0.6=fail) (Sing T, Sander O, Beerenwinkel N, Lengauer T. ROCR: visualizing classifier performance in R. Bioinformatics 2005; 21(20): 3940-1).

The entire patient cohort of 129 cases was divided into a training and a test dataset with a similar number of patients in each dataset (Table 5). For the training set, only samples that showed typical and definitive pathological features were included in order to achieve a reliable classifier. In addition, the training dataset was required to contain similar numbers of specimens for each category (68 cases total). For the test dataset an inclusive approach was taken, whereby all remaining tauopathy specimens received from the brain banks were utilized without further exclusion criteria, resulting in a heterogeneous set of samples (61 cases total): These included cases that had been diagnosed over 15 years ago when criteria for diagnoses were less advanced (5 cases). For other samples, the pathology reports described co-occurring pathologies, i.e. the patient brain showed the pathologies of two different tauopathies (5 cases). Finally there were subjects with less confident diagnosis, i.e. that displayed less pronounced or atypical pathological features (4 cases), or reported unavailability of sections routinely evaluated as part of the diagnosis (1 case). Given this heterogeneity, the inventors hypothesized that the output of the developed classifier for the test set would reflect the ambiguity of the sample set and perhaps allow the reclassification of the same cases.

Figure 7:
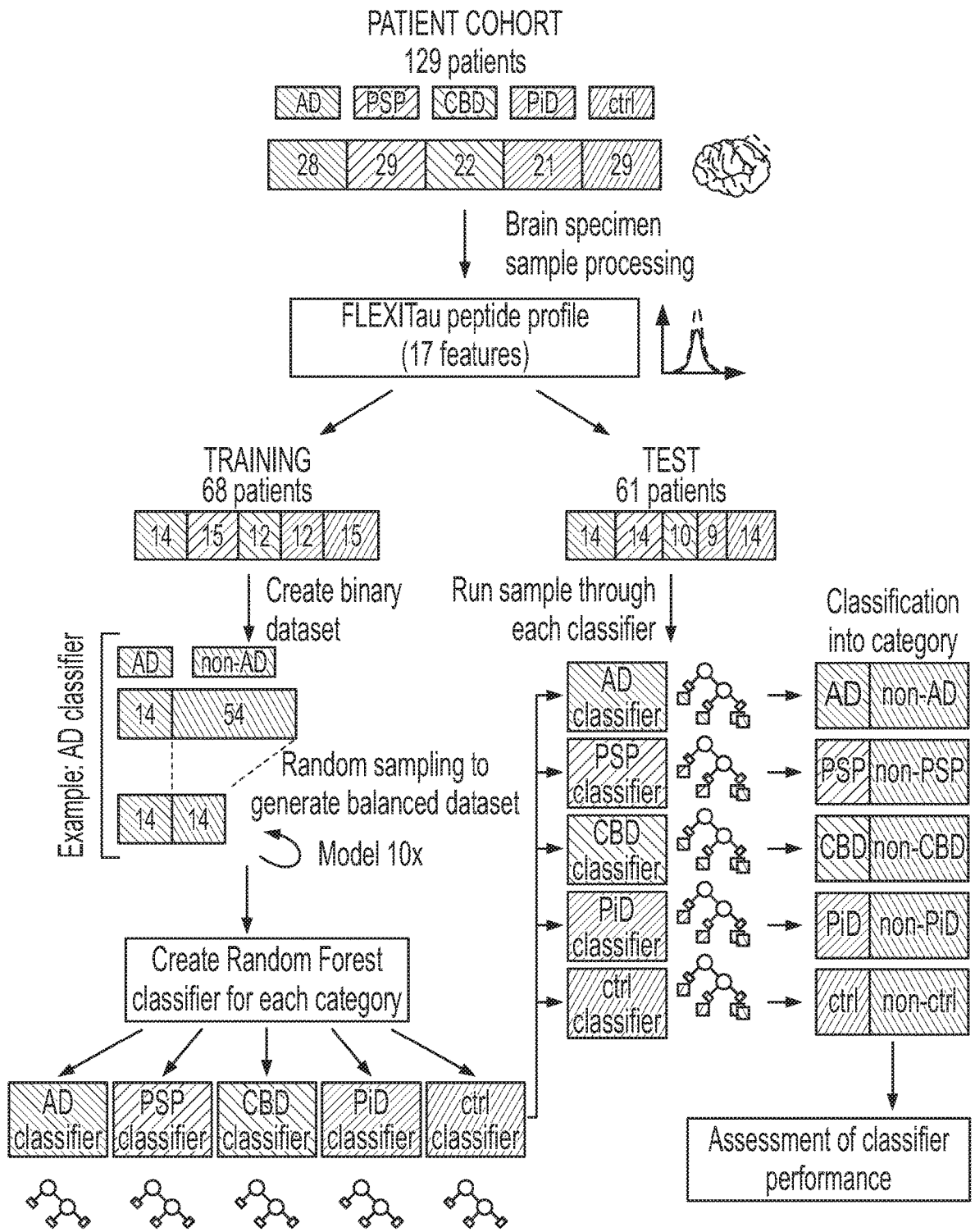
FIG. 7 is a schematic diagram showing the training and test phases involved in one exemplary process for the classifier development.

A supervised classifier was computed for each of the five patient categories under study, i.e. for AD, CBD, PSP, PiD and ctrl. For the training of a classifier for a certain disease category a binary approach was used whereby the case category (for example AD) is classified against the remaining 'mixed' reference category (consisting of all non-AD samples, e.g. CBD, PSP, PiD and ctrl). Given that the number of samples of each category in the training dataset is similar, the binary dataset is highly unbalanced. To remove the bias of training an unbalanced dataset, the 'mixed' reference category was down-sampled to create a unique balanced dataset with equal number of samples in both the case category and reference category in all subsequent model training and testing (FIG. 7). FIG. 7 shows that after sample processing of brain specimens, the training cohort was used to construct a computational classifier to discriminate each category using RF. The modeled classifier was then applied to an independent test data set and its performance in correctly predicting the category of each sample was evaluated.

The training process was repeated 10 times, i.e. each time a different subset of the reference category was randomly selected in order to obtain a stable classifier.

Figures 10A, 10B:
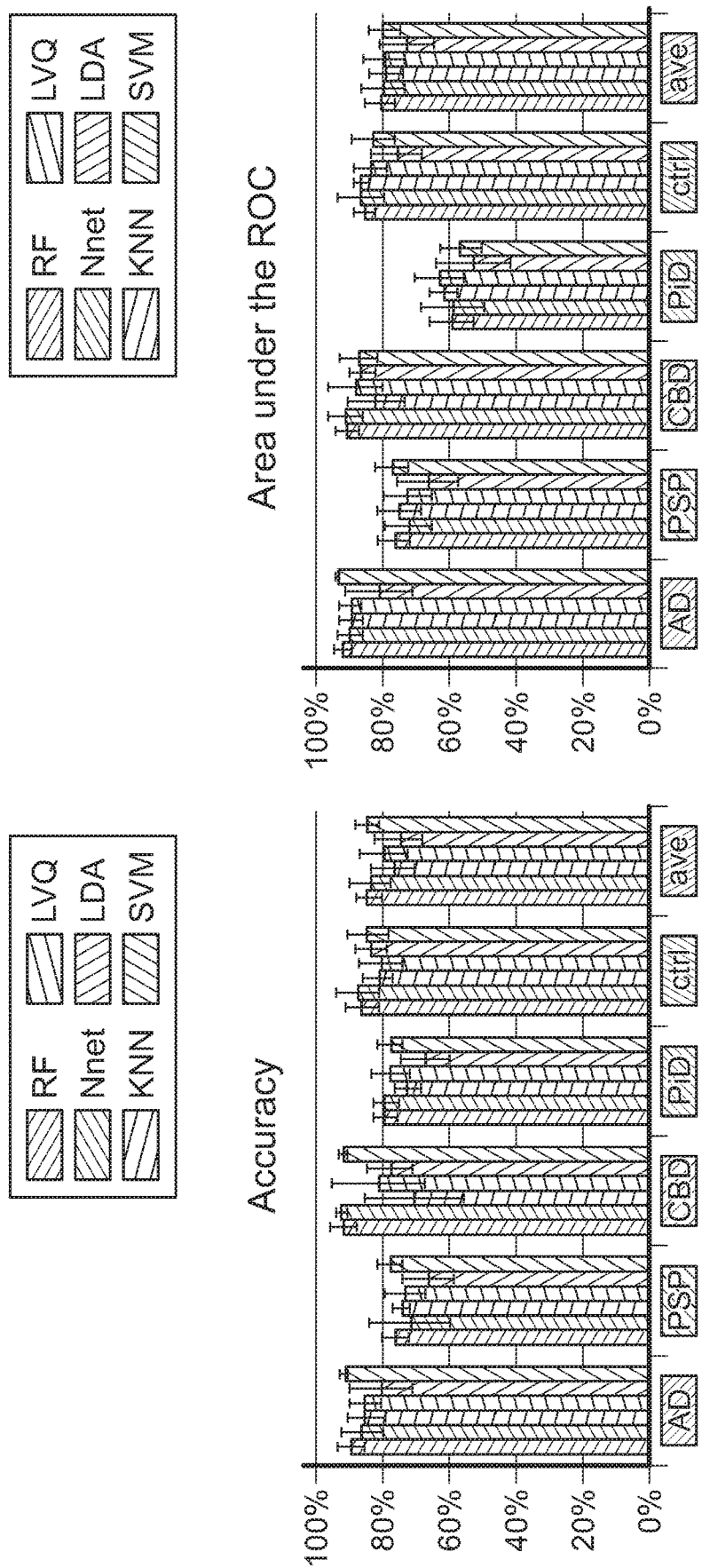
FIG. 10A is a graph showing accuracy of predicting each category from all others within the training set by Random forest (RF), Neural networks (Nnet), k-nearest neighbor (KNN), Learning Vector Quantization (LVQ), Linear Discriminant Analysis (LDA), and Support Vector Machines (SVM).
FIG. 10B is a graph showing area under the curve (AUC) of predicting each category from all others within the training set by RF, Nnet, KNN, LVQ, LDA, and SVM.
Figure 10C:
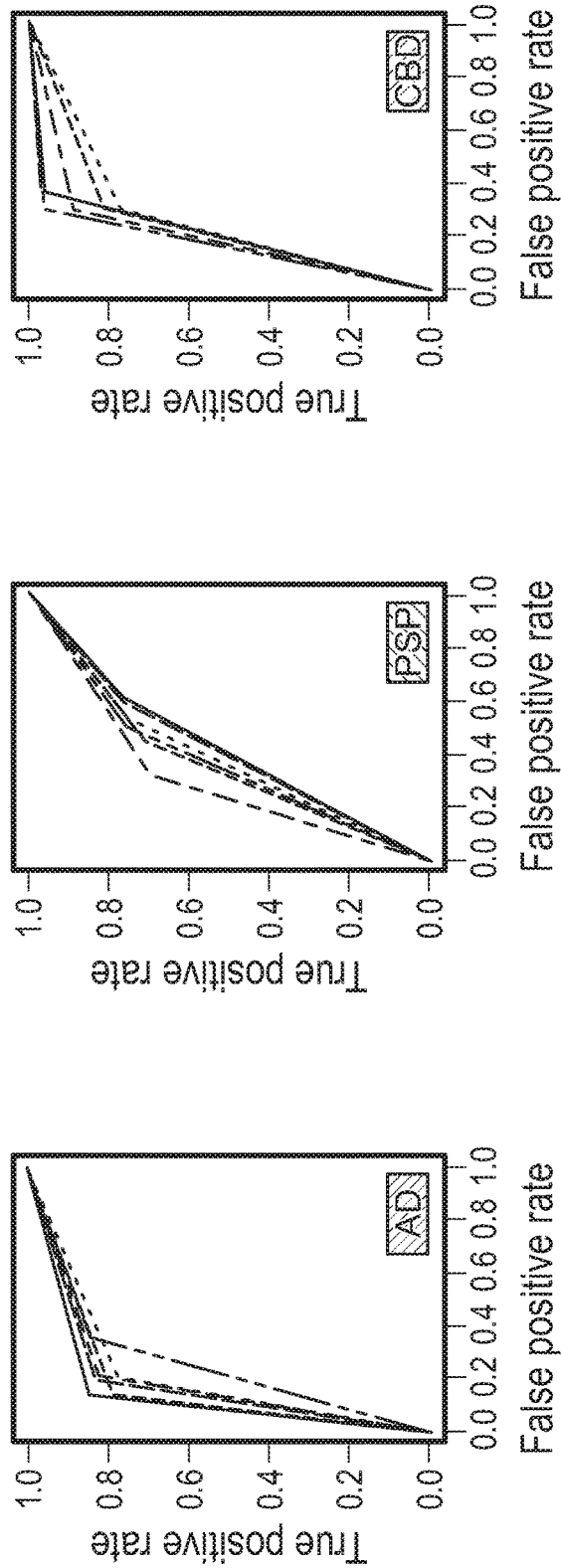
FIG. 10C is a set of graphs showing classifier performance plotted in receiver operating characteristic (ROC) space.
Figure 10C:
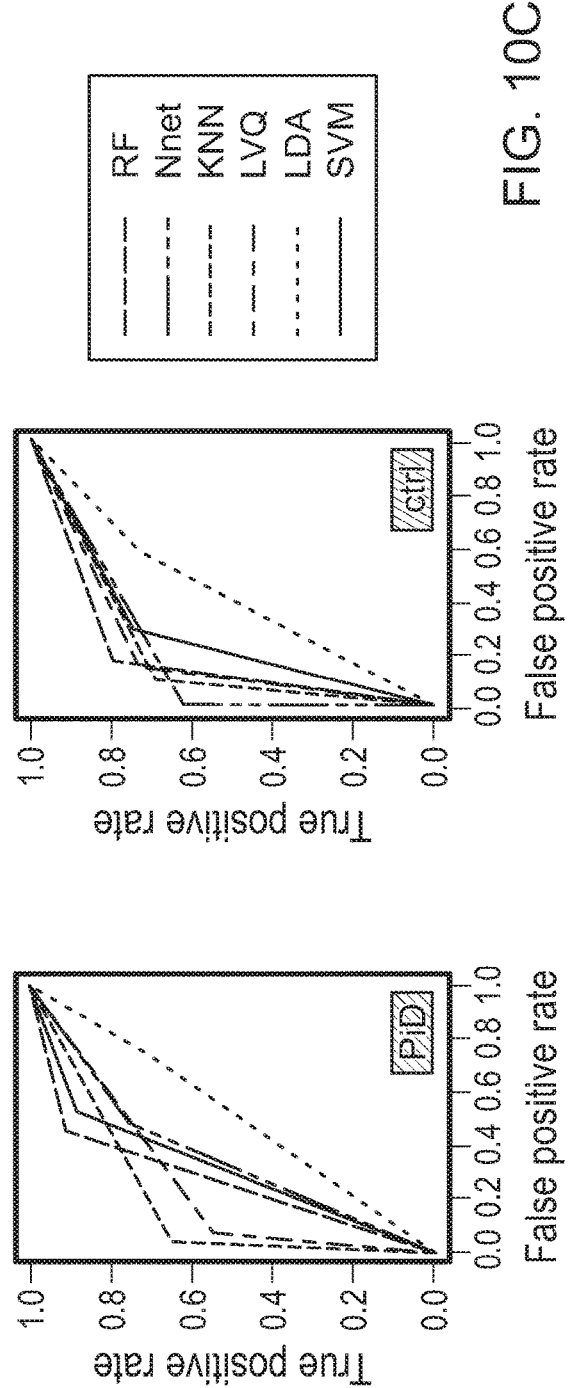

Five widely used supervised machine learning methods were initially evaluated: Random forest (RF) (Leo Breiman J F, Charles J. Stone, R. A. Olshens, J. Classification and Regression Trees. Wadsworth Statistics/Probability 1984; 1st Edition), Neural networks (Nnet) (Bishop C M. Neural Networks for Pattern Recognition: Oxford: Oxford University Press; 1995), k-nearest neighbor (KNN) (Altman N S. An Introduction to Kernel and Nearest-Neighbor Nonparametric Regression. The American Statistician 1992; 46(3): 175-85), Learning Vector Quantization (LVQ) (Kohonen T. Learning vector quantization: MIT Press; 1995), Linear Discriminant Analysis (LDA) (Fisher R A. THE USE OF MULTIPLE MEASUREMENTS IN TAXONOMIC PROBLEMS. Ann Eugen 1936; 7(2): 179-88), and Support Vector Machines (SVM) (Cortes C, Vapnik V. Support-Vector Networks. Machine Learning 1995; 20(3): 273-97). To determine performance, the average and standard deviation (SD) of accuracy and area under the ROC curve of 10 models were calculated. While the supervised classifiers performed comparably in the given data set, suggesting that the dataset does not favor a particular method, slightly better results were obtained for RF and SVM classifiers (FIGS. 10A-10C and Table 7). Variance of below 5% for both accuracy and AUC indicated that both RF and SVM performed robustly with different randomly selected subsets of the dataset. The RF method holds the advantage over SVM that features associated with the discrimination of the groups can be easily extracted and was thus selected as method for the classification. Another reason for selecting the RF classifier is that the method provides an unbiased estimate of the classification error named the "Out Of Bag" (OOB) error.

Statistical Methods

Figure 6A:
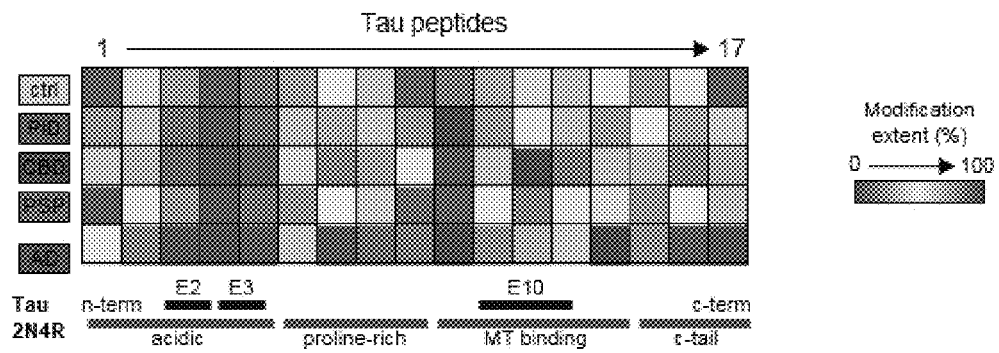
FIG. 6A is a diagram showing a heatmap for FLEXITau data obtained by targeted SRM.
Figure 6B:
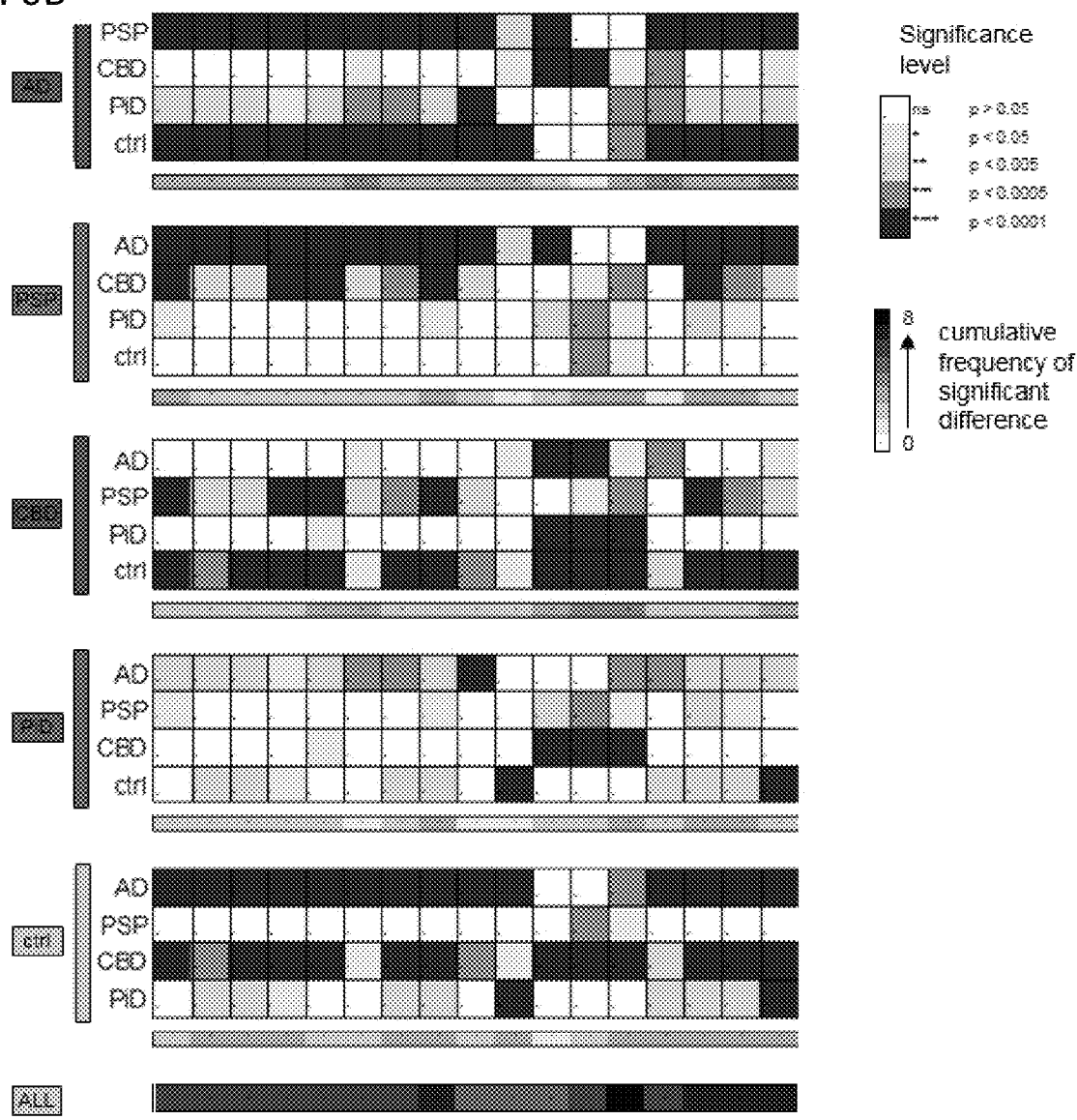
FIG. 6B is a diagram showing the comparison of the extent of peptide modification in AD, PSP, CBD, PiD, ctrl categories.
Figure 6C:
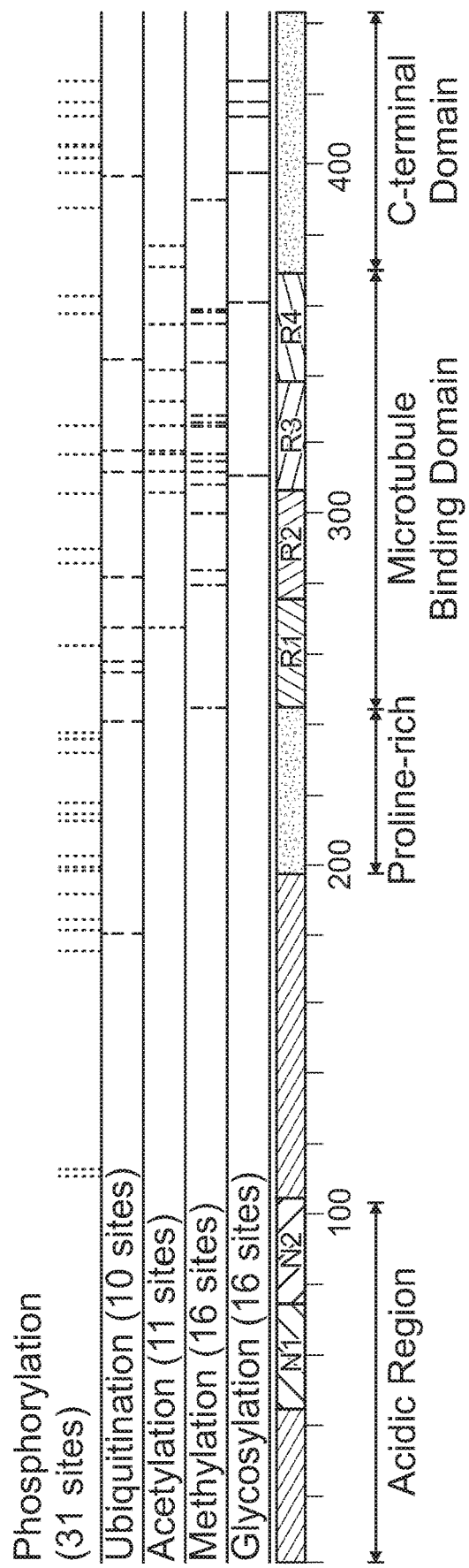
FIG. 6C is a schematic diagram showing the cumulative PTM map derived by MS shotgun analysis from the sarkosyl insoluble fraction of 17 AD patient samples.

To test whether features differed across groups, the Kruskal-Wallis test was used, which is a nonparametric multigroup comparison test, followed by Dunn's multiple comparisons test with adjusted P-value for comparison between two groups. All P-values were two-sided and P<0.05 was considered significant (FIGS. 6A-6C). FLEXITau peptide data was represented as boxplots for each category, showing the median of all samples with boxes representing 25% and 75% percentiles, and whiskers 5% and 95% percentiles. For the analysis of 4R-tau specific peptides, for each disease the average value of the three Exon 10 spanning peptides was calculated and normalized by the average value of that particular peptide in ctrl. Data is presented as average of the three peptides+/−relative error. Significance was analyzed by ANOVA, followed by the post hoc pairwise Bonferroni test with adjusted P-value for multiple comparisons. Analyses were carried out in Microsoft Excel (version 14.2.2), Prism 6.0 (GraphPad Software, La Jolla, Calif.) and the freely available software R (versions 3.2.1).

Results

It is well established that pathological tau carries a large number of PTMs and that, in certain tauopathies, tau spliceform homeostasis is perturbed (Yoshida M. Cellular tau pathology and immunohistochemical study of tau isoforms in sporadic tauopathies. Neuropathology 2006; 26(5): 457-70; Sergeant N, Delacourte A, Buee L. Tau protein as a differential biomarker of tauopathies. Biochim Biophys Acta 2005; 1739(2-3): 179-97; Martin L, Latypova X, Terro F. Post-translational modifications of tau protein: implications for Alzheimer's disease. Neurochem Int 2011; 58(4): 458-71; Espinoza M, de Silva R, Dickson D W, Davies P. Differential incorporation of tau isoforms in Alzheimer's disease. J Alzheimers Dis 2008; 14(1): 1-16). Based on the fact that pathological deposits in neurons and glia show characteristic differences in each tauopathy, the inventors hypothesized that pathological tau in each tauopathy presents with a unique molecular composition—a signature—, determined by its modification state and isoform distribution, and that this signature could be used to distinguish between tauopathies. However, identification and quantification of the different PTM states and splice forms of tau is challenging even with the most advanced analytical methods due to the complexity and molecular heterogeneity of tau. To circumvent this challenge, the inventors employed an alternative strategy, FLEXITau, an MS-based assay that measures the abundance of the portion of tau peptides which are left unmodified, relative to heavy tau peptides from an isotope labeled tau standard that is added to the sample, thus accurately inferring the extent of modification on each endogenous tau peptide.

To assess the PTM and splice landscape of tau in the various tauopathies, the FLEXITau assay was used to profile the peptide landscape of tau from a total of 129 post mortem cortical brain specimens from 5 different brain banks including the following 5 diagnostic groups: 28 AD, 29 PSP, 22 CBD, 21 PiD, and 29 non-demented controls (Table 4). Insoluble tau was isolated by classical sarkosyl fractionation from each specimen and processed using the FLEXITau workflow, which requires the addition of an isotope-labeled heavy tau standard, followed by SRM analysis of the L/H peptide ratio. A total of 17 tau peptides, which were quantified robustly in each patient sample across the entire cohort, were selected for further analysis.

Figure 9A:
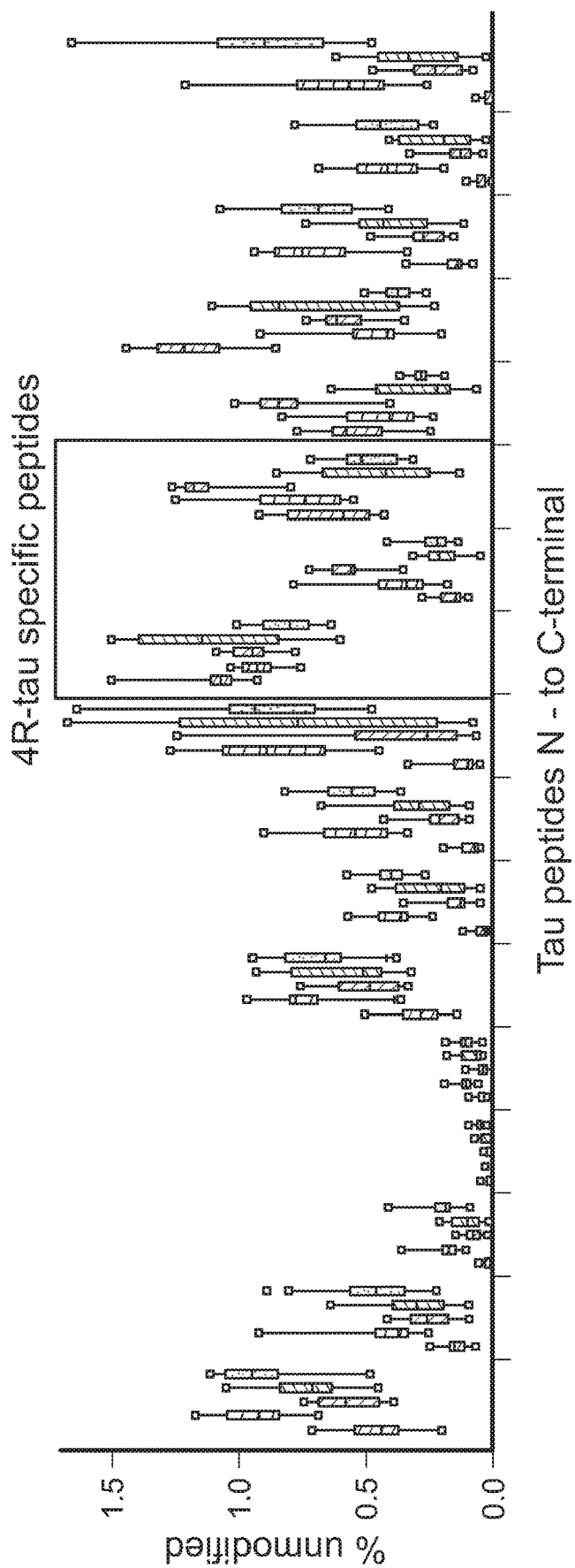
FIG. 9A is a graph showing normalized light-to-heavy ratio of signal intensities for 17 targeted peptides.

First, the inventors examined the molecular characteristics responsible for the separation of the diseases. The FLEXITau data obtained by targeted SRM allows for the quantitation of peptide modification extent (FIG. 9A). In FIG. 9A, normalized light-to-heavy ratio of signal intensities for the 17 targeted peptides was calculated for each sample. FIG. 9A shows boxplots for each disease as median with boxes representing 25% and 75% percentiles, and whiskers 5% and 95% percentiles.

Figure 9B:
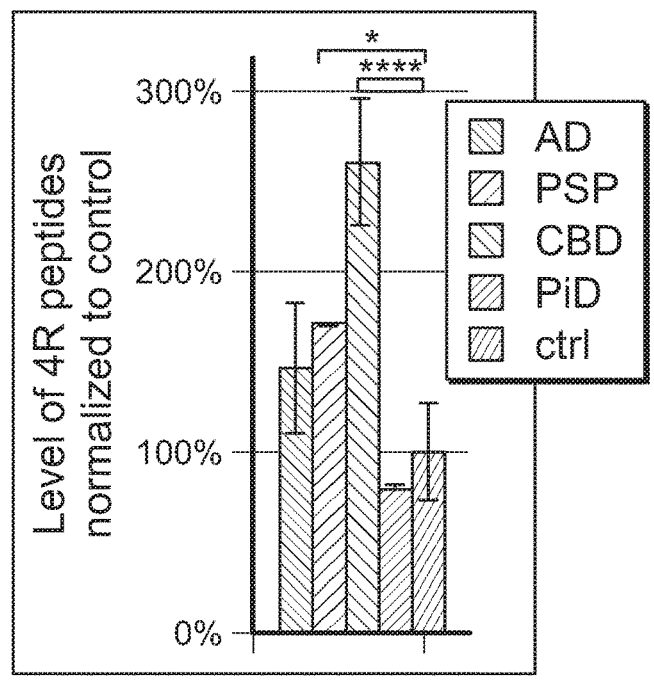
FIG. 9B is a graph showing mean values of 4R-tau specific peptides, relative to ctrl values+/−relative error (significance determined by ANOVA followed by post hoc pairwise Bonferroni).
Figure 9C:
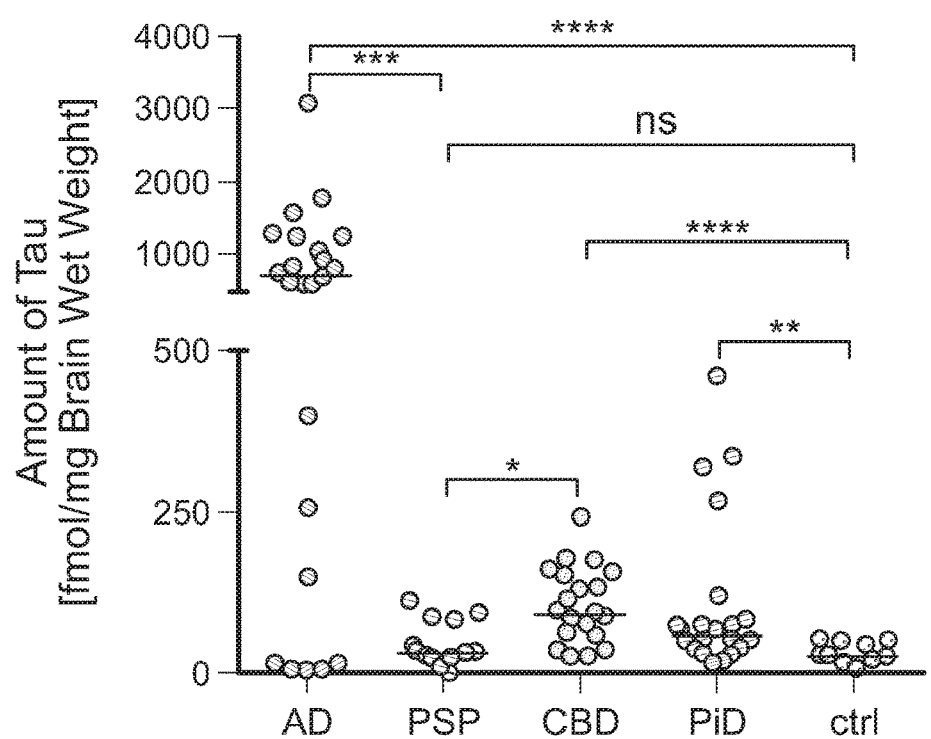
FIG. 9C is a graph showing absolute amounts of tau that were determined using one exemplary method described in this disclosure.

Clear quantitative differences in the modification extent could be observed for all categories (FIG. 6A). In FIG. 6A, the FLEXITau data obtained by targeted SRM was used to extract the median peptide modification extent, represented in a heatmap. Tau from AD patients presented a distinct quantitative molecular signature that was unique compared to all other categories. Amongst all diseases it displayed the highest modification stoichiometry, particularly in the acidic region, the proline rich region and the C-terminal tail. In FIG. 6B, the peptide modification extent is compared to another category and the significance determined (Kruskal Wallis followed by pairwise Dunn's multiple comparisons test). For each peptide, the cumulative frequency of that particular peptide being significantly different (p<0.05) is displayed in a heatmap (grey), for each disease and cumulative for all diseases (bottom). When the significance of peptide modification extent from one disease to other tauopathies was calculated, 75% of all AD peptide modification extents were found to be significant from the other categories (p<0.05) (FIG. 6B, first panel). The two categories with the least difference from each other were PSP and ctrl samples, with only two peptides (peptides 12 and 13) whose modification extent was significantly different from each other. Both peptides span Exon 10 in the MT-binding region (FIG. 6B, second panel). Analysis of all 3 exon-10 spanning peptides (peptides 11, 12 and 13) revealed that both for CBD and PSP, these peptides are significantly enriched in the insoluble tau (FIG. 9B). An overall, cumulative analysis of significant peptides in all diseases showed that the C-terminal tail and part of the MT-binding domain showed the highest difference in modification extent between the categories. It is important to note that these results also showed that every single peptide has a different modification extent in two or more categories. The FLEXI- Tau workflow also enables the absolute quantification of total tau present in the analyzed samples independent of its modification state. Absolute quantification of tau in the insoluble tau samples showed that in AD, CBD, and PiD, the amount of tau was significantly higher than in ctrl (FIG. 9C). In FIG. 9C, absolute amounts of tau were determined using the FLEX peptide. Tau levels were calculated as fmol tau per mg cortical brain wet weight. It shows average of the technical replicates for each sample (significance determined by Kruskal Wallis followed by pairwise Dunn's multiple comparisons test). *p≤0.05, p≤0.01, *p≤0.001, ****p≤0.0001, ns=non-significant.

In the parietal cortex tissue samples, PSP showed insignificantly higher tau levels than control, and significantly lower levels than AD and CBD. AD contained the highest amount of tau, with the majority of AD samples containing 5-10 fold higher tau levels than the samples of the other categories.

Next possible PTMs associated with these samples were identified by creating a cumulative PTM map. Using shotgun MS, 17 AD patients, three of which were extensively fractionated prior to analysis, were analyzed. The reason for choosing AD samples for the cumulative map is twofold: 1) tau abundance in sarkosyl insoluble samples was much higher than in any of the other diseases, facilitating the identification of PTMs, and 2) to our knowledge (including from our data) so far all PTMs discovered in non-AD tauopathies have been also identified in AD. In the analysis, a total of 74 PTMs were identified with high confidence (FIG. 6C and Table 7). FIG. 6C shows the cumulative PTM map derived by MS shotgun analysis from the sarkosyl insoluble fraction of 17 AD patient samples, 3 of which were extensively fractionated to increase sequence coverage. Bars represent sites occupied by respective modifications. Sequence shown is 2N4R, with the exons prone to alternative splicing marked by red box.

31 phosphorylations, 10 ubiquitinations, 11 acetylations, 16 methylations and 6 glycosylation sites were mapped. Apart from phosphorylation that has its highest frequency in the proline-rich region and the C-terminal tail, the other modifications cluster in the microtubule-binding region. From the 74 mapped PTMs, 46 have not been described before in human brain-derived tau (Table 7). These include 11 novel acetylation and 6 novel ubiquitination sites.

Example 4: Classifying Disease Categories by Using Quantitative Peptide Features Experiments were performed to classify disease categories by using quantitative peptide features by using methods as described in Example 3. Example 3 shows that there are clear differences in the quantitative peptide landscape of tau that arises from different modification stoichiometries and isoform distribution of tau in these diseases, resulting in a molecular signature for each disease. Thus, experiments were performed to test whether these quantitative peptide features could be used to accurately classify the disease categories.

To this end the FLEXITau data was used to construct a binary classifier for each disease category using a supervised machine learning strategy (see workflow in FIG. 7). The patient cohort was divided into an independent training and test set, consisting of similar numbers of patients in each patient group (Table 5). The process of supervised machine learning consisted of two phases, the first phase was the training of the classifiers using the training dataset and the second is the testing of the classifiers on the independent test set.

First, the samples in the training set were used to construct a binary classifier for each chosen category that enables optimal separation of the case category (i.e. AD) from the remaining 'mixed' reference category (i.e. all non-AD). In order to remove the bias of training with an unbalanced dataset, during the training process the reference category was down-sampled to create a balanced dataset with an equal number of samples in both the case and reference category. Different supervised machine learning methods were tested and these performed similarly for the dataset (see methods). The RF method holds the advantage over SVM method as features associated with the discrimination of the groups can be easily extracted and thus RF was selected for the analysis presented here. Another reason for selecting the RF classifier is that the method provides an unbiased estimate of the classification error named the "Out Of Bag" (OOB) error.

Figures 11A, 11B:
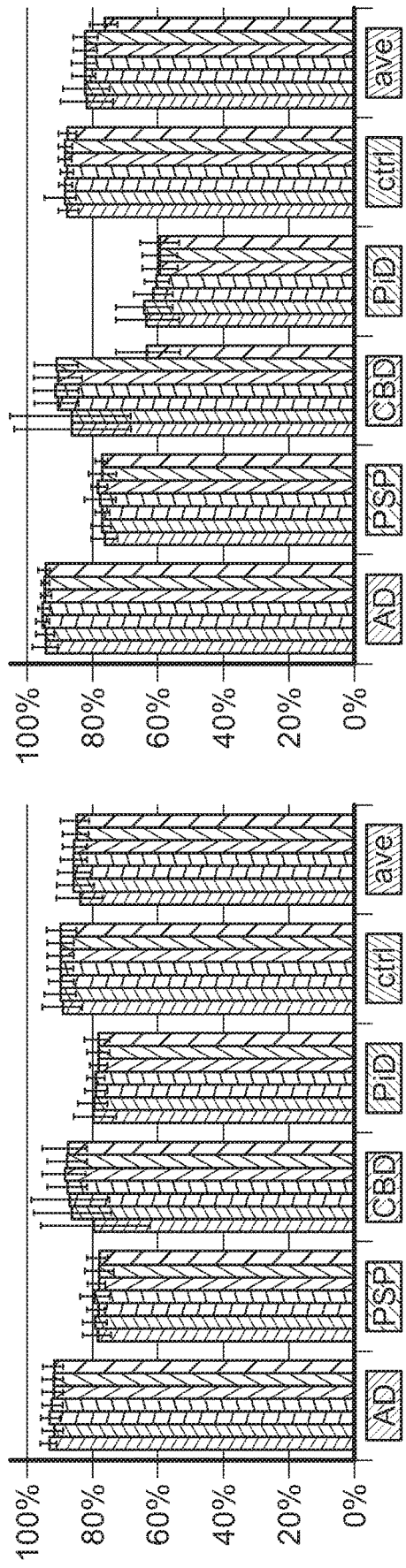
FIG. 11A is a graph showing accuracy after tenfold training and testing of RF classifier on randomly chosen test sets with a predetermined maximum number of splitter variables.
FIG. 11B is a graph showing area under the curve (AUC) after tenfold training and testing of RF classifier on randomly chosen test sets with a predetermined maximum number of splitter variables.
Figure 11C:
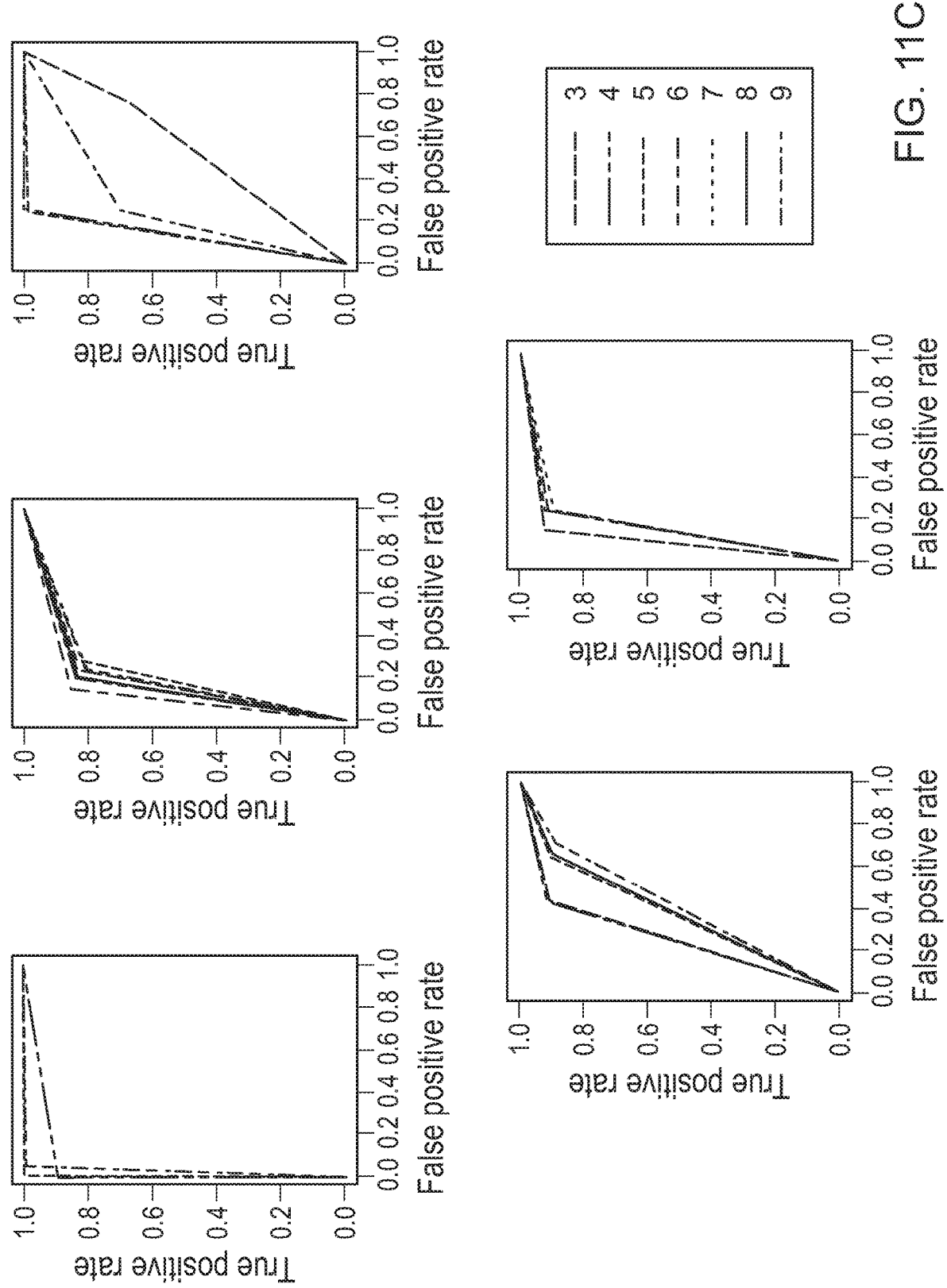
FIG. 11C is a set of graphs showing classifier performance plotted in receiver operating characteristic (ROC) space)

To maximize the performance of the RF classifier, the best number of features used to build the decision trees was determined. In RF classification, peptides are selected based on importance as features that can split the data into stable groups by building each bootstrap tree (using random sampling with replacement). If features are highly correlated, only a subset is needed to achieve good performance. A small number of features may improve the performance and avoid overfitting. The number of peptides features required to develop a robust classifier was tested by evaluating the performance of each classifier. The average accuracy and AUC of the ROC curve for each patient group was calculated after ten iterations of training and testing on random subsets of the training set (FIGS. 11A-11C). In FIGS. 11A-11C, accuracy (FIG. 11A) and area under the ROC curve (FIG. 11B) after tenfold training and testing of RF classifier on randomly chosen test sets with a predetermined maximum number of splitter variables. Shown are the mean (+/−stdev) for each condition and the average of all conditions for each classifier (grey). FIG. 11C shows classifier performance plotted in ROC space (representative curves shown). The raw values are provided in Table 9.

The robustness of the RF classification based on tau peptides was emphasized by the observation of minimal changes in performance upon altering the number of features (on average, less than 1% standard deviation, see Table 9). Overall, limiting the number of features to 6 peptides minimized variance while maximizing performance for each patient group and thus was used for the remaining data analysis.

Next, whether the abundance of insoluble tau in each sample represents an important feature that would improve the diagnostic performance of the classifier was investigated. To this end, the absolute tau levels present in each sample were included as an additional feature in the feature set. The RF classifier was then retrained and tested, either including or excluding this 18th feature. On average, the inclusion of the abundance feature led to a decrease in both accuracy and AUC (reduction by 0.5% and 6.3%) (FIGS. 12A-12D). The decrease in performance was highest for the PSP category (reduction of AUC by 22.2%) and PiD (reduction of AUC by 9.8%). When included, the abundance feature was chosen as one of 6 features by all classifiers with the exception of CBD (Table 10). As no improvement in performance was observed, for the final model, the abundance feature was not included in the training of the classifier.

A final optimized RF classifier that was trained using the complete training set of 68 patient samples was produced. The best OOB error rate achieved for this training data set was 1.5% for AD, while the average OOB error rate was 8.3% (FIG. 13A; out of bag error—an estimate of the error rate for RF supervised learning). In FIGS. 13A-13D, a classifier based on the RF method was trained for each disease group using the entire training set and its performance assessed on the entire independent test set. This trained classifier was then applied to the independent test cohort of 61 patient samples (see Table 5). In contrast to the training set, which contained patient samples with definitive neuropathological diagnoses, the test set contained patient specimens received from the brain banks without any exclusion criteria. As such, it included samples with less clear-cut diagnoses, diagnoses dating back more than a decade, and brains displaying mixed dementias (see Methods for details). These samples were included at this stage of testing to determine if the classifier could detect heterogeneity at the molecular level or perhaps determine a conclusive diagnosis. A summary of the initial classification results is presented in FIGS. 13A-13D and Table 11.

Overall, 16.1% of the samples (31 cases total) were assigned to a category other than that of their primary diagnosis (FP) and/or were not assigned to the category of their primary diagnosis (FN) (Tables 12). 15 of these cases were not assigned to the category of their primary diagnosis but to another one (FP and FN). In 13 cases, the primary diagnosis was confirmed but the sample was also assigned to another category (FP only) (i.e. samples were selected by two classifiers). 3 samples were not selected by any of the classifiers (FN only). To determine if these FP and/or FN assignments had underlying pathologies that were not explained by the primary diagnosis, the outcome from the classifiers were cross-referenced with pathology reports and clinical information, if available and followed up with the neuropathologists at each brain bank. Remarkably, for more than half of these specimens (17 cases) the assignment by the classifiers could be explained by underlying pathological characteristics or other reasons (see Table 12 and FIG. 13D). FIG. 13D shows identification of FN cases for each classifier. The percentage indicates the FNR (number of FN relative to all positive cases).

The samples were categorized into three groups, which are described below:

1) Co-occurring pathology (4 cases): Several samples were assigned as AD by the AD classifier although their primary diagnoses were PSP (1 case) or PiD (3 cases); for all 4 cases the pathology reports described evidence of overlapping AD pathology (4 cases). This result corroborates the accuracy of the diagnosis by the AD classifier as notably for the other 101 non-AD cases no evidence of AD was described in the pathology reports. Remarkably the 3 PiD cases were also recognized by the PiD classifier, and the pathology reports also describe typical PiD features.

2) Asymptomatic or atypical pathology (this group comprises several types of samples, 11 cases total): For several samples whose primary diagnosis was not recognized by the respective classifier (5 PSP cases and 1 PiD case) "cortical sparing" was described in the reports or stated upon re-evaluation of the samples by the pathologist. In these cases, PSP pathological hallmarks were sparse or absent in the brain region received for this study, explaining the result. For an additional three cases that were reassigned by the classifiers to another disease group, the final pathological diagnosis was stated to be not definite or atypical (1 AD, 1 PSP, 1 PiD). One other PiD case that was assigned to ctrl instead of PiD turned out to be an archival case that was re-evaluated and found to be tau-negative but positive for TDP-43 (FTLD-TDP). Finally, one ctrl case that was not recognized as control by the ctrl classifier reported a "recent history of dementia", suggesting that our classifier picked up tau-related changes in the brain of this individual. For this case no immunohistochemistry staining was available that could confirm this speculation, and no follow-up staining could be performed due to lack of resources at the brain bank. Additionally, according to current definitions, the ascertainment of "ctrl" cases excludes clinically demented individuals; therefore this case was excluded from the cohort.

3) Wrong diagnosis (2 cases): The re-evaluation of archival cases using current immunohistochemistry techniques resulted in a change of diagnosis in two cases. First, a PSP case that was classified as CBD by the CBD classifier was re-diagnosed as CBD by the pathologist after re-evaluation (FIG. 14E). Furthermore, a CBD case not recognized by the CBD classifier, but assigned to PSP and ctrl, was re-evaluated as being not CBD (correct diagnosis unknown, requiring additional staining).

Overall, these results corroborate the specificity and sensitivity of the classifiers enabling the detection of comorbid pathologies and the reclassification of misdiagnosed samples. Of the remaining 45% of reclassified specimens (14 cases), half were ctrl cases that were inaccurately classified as PSP by the PSP classifier, while being correctly being classified as ctrl by the ctrl classifier (Table 13 and FIG. 13D). These findings, in combination with the relatively high OOB error rate for the PSP training set compared to the other categories, led us to conclude that the cause for most of the remaining mis-assignments was the performance of the PSP classifier. Possible causes for this lower performance are elaborated in the Discussion.

To accurately assess the performance of the classifiers, the trained classifier was re-applied to the test set after 1) assigning two different categories to the cases where co-occurring pathologies were described in the pathology reports (4 cases), 2) excluding the cases with asymptomatic or atypical pathology (12 cases), and 3) assigning the correct diagnosis for the misdiagnosed case (2 cases) (Table 6, see also Table 12). Diagnostic performance of the CBD and the ctrl classifier was highest, with an accuracy of 95.9% (90.0% sensitivity and 97.4% specificity for CBD, and 92.3% sensitivity and 97.2% specificity for ctrl) (FIG. 8 and Table 6). The AD classifier achieved an accuracy of 93.8% (sensitivity of 88.2% and specificity of 96.8%), and the PiD classifier achieved an accuracy of 91.8% (sensitivity of 83.3% and specificity of 93.0%). The performance of the PSP classifier was the lowest with 81.6.0% accuracy (71.4% sensitivity and 83.3% specificity).

Finally, the selection of peptides that were used by the classifiers to distinguish the disease categories was examined. For each binary classifier that was built, a distinct subset of 6 peptides was selected out of the 17 tau peptides. Of the 17 peptides, 5 peptides were not used by any classifier (FIG. 8D). From the remaining 12 discriminating peptides, 4 peptides were unique to one of the classifiers, suggesting that these peptides carry important disease-specific information. Notably, 3 out of these 4 peptides were located in the acidic n-terminal region of tau, including exon 2 and 3, which can be alternatively spliced. The other 8 peptides were shared among the classifiers, indicating that these peptides harbor characteristic information that discriminate several of the disease groups from each other. The majority of these peptides is located in the repeat region of tau, a region that harbors exon 10, the third exon prone to alternative splicing. FIG. 8D is a schematic diagram showing a heat map for discriminating peptide features for each classifier (bottom), and accumulative count (top). Discriminating peptide features for each classifier (bottom), and accumulative count (top), shown in a heat map representation. Peptides are mapped to a schematic of 2N4R tau; alternatively spliced exons 2 (E2), 3 (E3) and 10 (E10) are also shown in the figure.

This analysis showed that the majority of these misassigned samples fell into three categories 1) mixed pathology—pathological features of two tauopathies were noted; 2) samples with uncertain diagnosis or with spared pathology in the region of the cortex analyzed—this was common for PSP; and 3) samples that were reclassified and confirmed by follow-up immunohistochemistry.

To obtain an accurate assessment of the classifiers, cases presenting uncertain or asymptomatic pathologies were excluded and cases with co-occurring pathologies were assigned to two categories. The final classification achieved an accuracy of 95.9% for CBD and ctrl, 93.9% for AD, and 91.8% for PiD, while PSP had an accuracy of 81.6.0% (FIG. 8 and Table 6). It is important to note that several of the remaining mis-assignments (Table 13) are cases that were originally diagnosed without the use of immunohistochemistry, and due to lack of tissue at the brain bank no follow-up assessment could be performed to confirm the original diagnoses using current diagnostic standards, or to determine a change in diagnosis. Thus, it is speculated that more samples than assumed here are misdiagnoses, and that the performance of the classifiers may be underestimated.

Figure 8A:
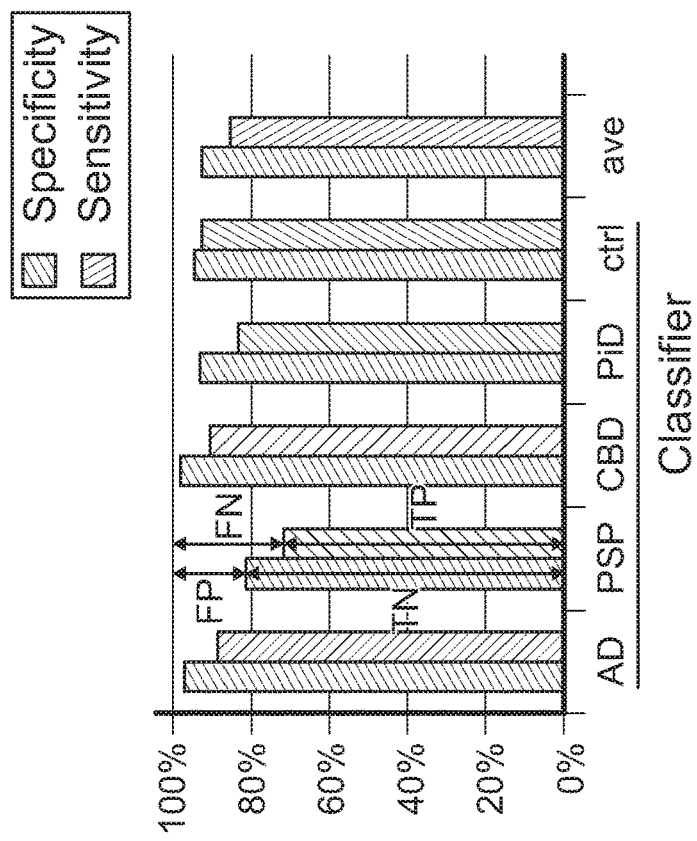
FIG. 8A is a graph showing "Out Of Bag" (OOB) accuracy, accuracy and AUC for each category and the average of all categories.
Figure 8B:
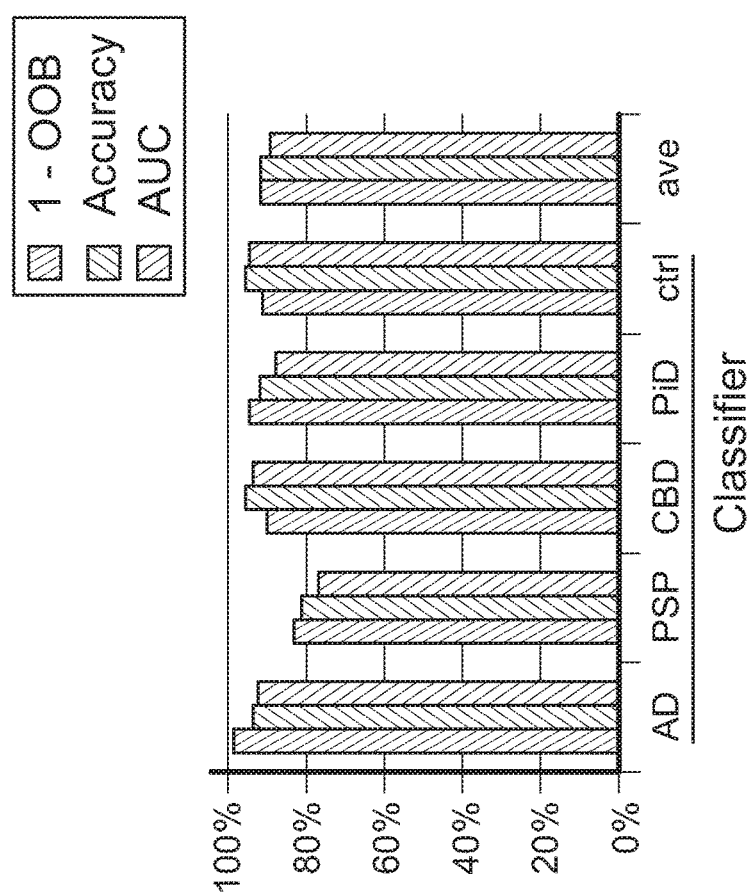
FIG. 8B is a graph showing specificity and sensitivity for each category and the average of all categories.
Figure 8C:
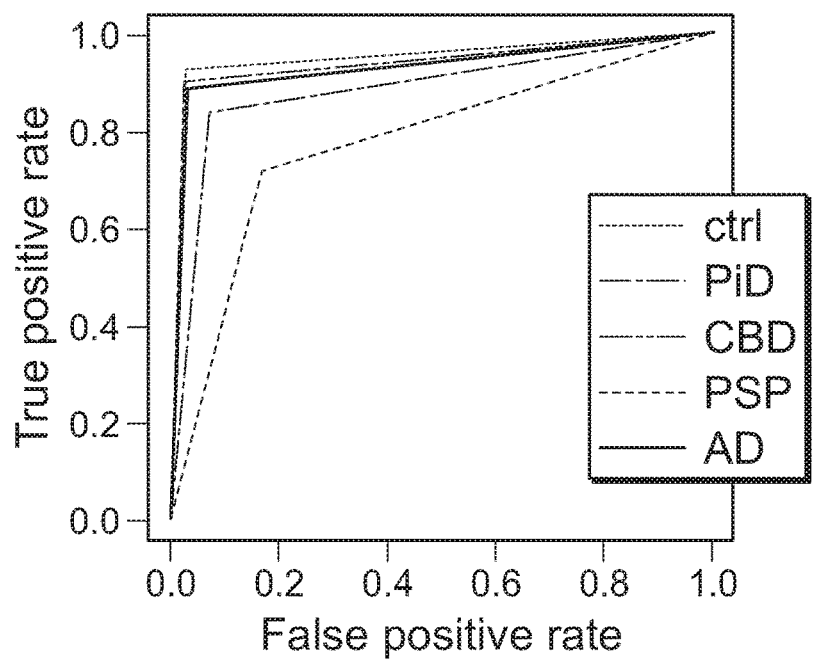
FIG. 8C is a graph showing performance of all classifiers in ROC space.
Figure 8D:
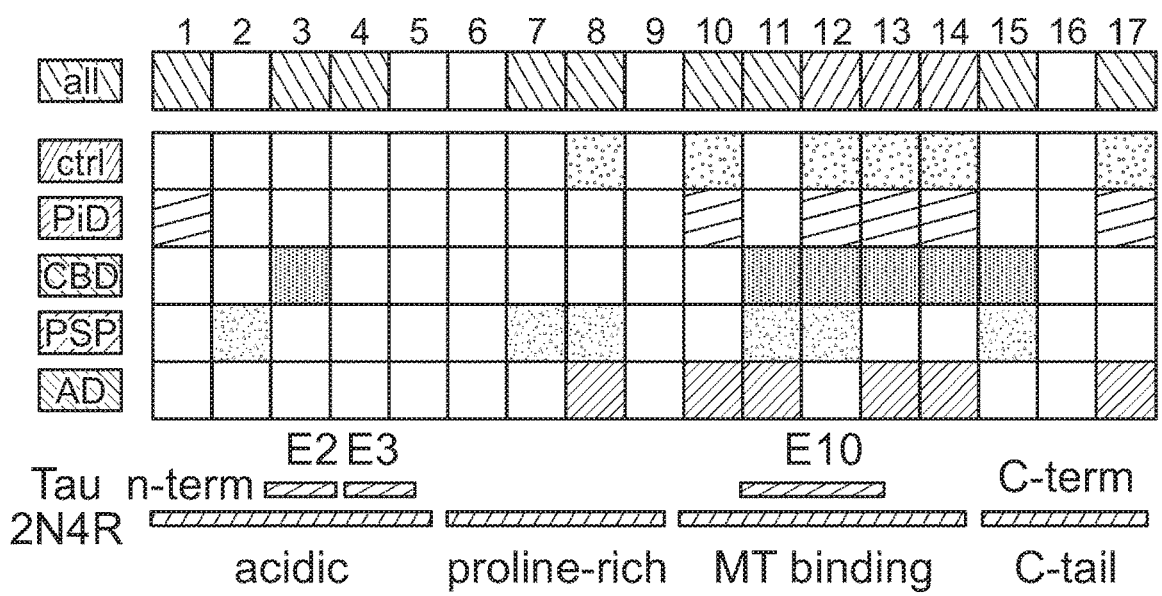
FIG. 8D is a schematic diagram showing a heat map for discriminating peptide features for each classifier (bottom), and accumulative count (top).

The analyses show that AD patient tau possesses a distinct quantitative molecular signature that resulted in 96.8% specificity of the AD classifier (FIG. 6 and FIG. 8B). Interestingly the AD classifier also recognized 4 cases where the primary diagnoses were either PiD (3 cases) or PSP (1 case). The pathology reports of these samples were investigated to better understand these results. The pathology of the three PiD cases indicated clear AD features (neuritic plaques, flame-like NFTs). The PSP case stated evidence of 'early' AD. This strongly suggests that the developed AD classifier is highly sensitive to AD co-morbidity and may recognize AD in its early stages. Importantly, all 3 PiD cases were correctly identified as TP with the PiD classifier, indicating that the performance of the PiD classifier is not hampered by the co-existing AD. These results exemplify that the combination of individual classifiers serves as a powerful tool to detect co-pathologies.

CBD is a disorder that is clinically heterogeneous presenting with various clinical syndromes. Corticobasal syndrome (CBS), the classical clinical manifestation of CBD, is neither predictive nor specific for CBD pathology. Efforts are being made to improve CBD clinical diagnosis clinically and recently new consensus criteria were established, however these were reported as unspecific and not sensitive to early CBD (Armstrong M J, Litvan I, Lang A E, et al. Criteria for the diagnosis of corticobasal degeneration. Neurology 2013; 80(5): 496-503; Alexander S K, Rittman T, Xuereb Bak T H, Hodges J R, Rowe J B. Validation of the new consensus criteria for the diagnosis of corticobasal degeneration. J Neurol Neurosurg Psychiatry 2014; 85(8): 925-9; Ouchi H, Toyoshima Y, Tada M, et al. Pathology and sensitivity of current clinical criteria in corticobasal syndrome. Mov Disord 2014; 29(2): 238-44). In fact, CBS is more likely to be caused by a pathology other than CBD, e.g. PSP, AD, PiD, or is unrelated to tau when evaluated post-mortem (Ling H, O'Sullivan S S, Holton J L, et al. Does corticobasal degeneration exist? A clinicopathological re-evaluation. Brain 2010; 133(Pt 7): 2045-57; Wadia P M, Lang A E. The many faces of corticobasal degeneration. Parkinsonism Relat Disord 2007; 13 Suppl 3: S336-40). At a neuropathological level, diagnosis of CBD is now straightforward (e.g. FIG. 14E), but in the past was complicated by the heterogeneity and variability of tau pathology, as well as overlapping pathological features with other tauopathies (Wakabayashi K, Takahashi H. Pathological heterogeneity in progressive supranuclear palsy and corticobasal degeneration. Neuropathology 2004; 24(1): 79-86; Tsuchiya K, Ikeda K, Uchihara T, Oda T, Shimada H. Distribution of cerebral cortical lesions in corticobasal degeneration: a clinicopathological study of five autopsy cases in Japan. Acta Neuropathol 1997; 94(5): 416-24; Forman M S, Zhukareva V, Bergeron C, et al. Signature tau neuropathology in gray and white matter of corticobasal degeneration. Am J Pathol 2002; 160(6): 2045-53). In particular, CBD and PSP were suggested to be part of a clinicopathologic disease spectrum, as in some cases, these diseases show similar clinicopathological features, i.e. both present with neuronal, oligodendroglial, and astrocytic lesions immunoreactive for 4R tau, which made a correct classification difficult (Dickson D W. Neuropathologic differentiation of progressive supranuclear palsy and corticobasal degeneration. J Neurol 1999; 246 Suppl 2: 116-15; Josephs K A. Key emerging issues in progressive supranuclear palsy and corticobasal degeneration. J Neurol 2015; 262(3): 783-8; Williams D R, Lees A J. Progressive supranuclear palsy: clinicopathological concepts and diagnostic challenges. Lancet Neurol 2009; 8(3): 270-9). Considering these issues, it is noteworthy that in this analysis the only 2 FP cases recognized by the CBD classifier in the test set were 2 PSP cases, consistent with the suggested molecular overlap of these two diseases. One of these PSP cases was re-diagnosed as CBD after re-evaluation with immunohistochemistry stainings (see Table 12, Case #5). No other non-CBD patient (out of 51 total) was mis-assigned to CBD, resulting in excellent specificity (97.4%). Additionally, one of the 2 FN cases (i.e. a CBD case not recognized by the CBD classifier) was determined as not being CBD after re-evaluation by the pathologist (see Table 12, Case #6). These results highlight the power of using the tau peptide signature to accurately differentiate heterogeneous, overlapping disease phenotypes, and detect misdiagnoses.

The classic clinical presentation of PSP is Richardson syndrome, also known as Steele-Richardson-Olszewski syndrome; however, similar to CBD, several clinical variants can arise from pathologically defined PSP. Defining a classifier for this disease is challenging for multiple reasons: First of all, studies of PSP have reported relative sparing of cerebral cortex in typical PSP cases, both in terms of atrophy and tau pathology (Tsuboi Y, Josephs K A, Boeve B F, et al. Increased tau burden in the cortices of progressive supranuclear palsy presenting with corticobasal syndrome. Mov Disord 2005; 20(8): 982-8; Williams D R, Holton J L, Strand C, et al. Pathological tau burden and distribution distinguishes progressive supranuclear palsy-parkinsonism from Richardson's syndrome. Brain 2007; 130(Pt 6): 1566-76). Furthermore, each variant of PSP has variations in the type of tau lesion, the load of tau and the distribution of tau pathology (Braak H, Jellinger K, Braak E, Bohl J. Allocortical neurofibrillary changes in progressive supranuclear palsy. Acta Neuropathol 1992; 84(5): 478-83; Dickson D W, Hauw J-J, Agid Y, Litvan I. Progressive Supranuclear Palsy and Corticobasal Degeneration. Neurodegeneration: The Molecular Pathology of Dementia and Movement Disorders: Wiley-Blackwell; 2011: 135-55; Hof P R, Delacourte A, Bouras C. Distribution of cortical neurofibrillary tangles in progressive supranuclear palsy: a quantitative analysis of six cases. Acta Neuropathol 1992; 84(1): 45-51; Piao Y S, Hayashi S, Wakabayashi K, et al. Cerebellar cortical tau pathology in progressive supranuclear palsy and corticobasal degeneration. Acta Neuropathol 2002; 103(5): 469-74; Verny M, Duyckaerts C, Agid Y, Hauw J J. The significance of cortical pathology in progressive supranuclear palsy. Clinico-pathological data in 10 cases. Brain 1996; 119 (Pt 4): 1123-36).

For example, the 'brainstem predominant' atypical PSP presents with significantly lower pathological tau burden in cortical regions, especially temporal and parietal lobes. In contrast, the 'cortical predominant' atypical PSP (which often present with clinical presentations of CBS) displays greater cortical tau pathology compared to typical PSP. The variability in tau burden might not only explain difficulties in developing a PSP classifier based on cortical tissue outside of motor cortex, but may also explain why the addition of tau abundance into the feature set failed to improve the performance of the classifier. Given these issues, it was surprising that the PSP classifier achieved an accuracy as high as 81.6%. To confirm that the underlying performance was affected by the tau load, the severity of tau pathology using the pathology reports and follow-up immunohistochemistry analyses of tissue was investigated. The majority of mis-assigned PSP tissue samples showed evidence of the cortex as being spared of tau pathology, suggesting that the tau analyzed in the assay was closer to normal tau than pathological tau. In conclusion, the classifier was trained and applied on a heterogeneous set of samples including those with "normal" tau in this region. Given this issue, it is understandable that the PSP classifier also recognizes ctrl cases as PSP.

Examples of misclassified cases are also summarized in FIGS. 14A-14E. Cases reassigned by the classifiers to categories other than that of their primary diagnosis were inspected manually by evaluation of pathology reports, and/or follow-up immunohistochemistry of tau (3R and 4R tau, and/or AT8 tau staining). FIG. 14A is a schematic diagram showing that 3 PiD cases were classified as PiD and as AD by the RF classifiers. Pathology reports show that all three cases had AD co-pathology that was insufficient according to CERAD criteria (Cases #2, 3 and 4 in Table 12). FIG. 14B shows PSP case that was not recognized by the PSP classifier was instead classified as AD by the AD classifier. Pathology report lists early AD as secondary diagnosis (Case #1 in Table 12). FIG. 14C shows one exemplary PSP case for evidence of cortical area being spared by tau pathology (Case #11 in Table 12). FIG. 14D shows one case diagnosed as PSP with unusual severe pathology in the brainstem was classified as CBD (Case #17 in Table 12).

Interestingly, of all classifiers, the ctrl classification achieved the highest sensitivity of 92.3%. This reflects the strong ability of the ctrl classifier to predict true positive ctrl cases. The excellent sensitivity of the ctrl classifier provides evidence that tau found in ctrl patient tissue has unique molecular properties that distinguishes it from pathological tau. The characterization of the distinct molecular entities (i.e. particular modifications) responsible for the discrimination of controls from diseased cases may yield valuable insights for developing tau-directed therapeutic strategies against tauopathies, such as immunotherapy approaches.

Several bioinformatics models were also explored for the construction of a classifier to distinguish each disease class. All tested algorithms obtained accuracies of 75-85% in separating the diseases (FIGS. 10A-10C and Table 8). Performance of RF, Nnet, KNN, LVQ, LDA, and SVM in correctly predicting each category from all others within the training set was assessed by FIG. 10A accuracy and FIG. 10B AUC of the ROC curve. FIGS. 10A-10B shows the mean+/−SD after tenfold training with different subsets of the reference categories for each disease category, and the average performance over all categories of each method (grey). FIG. 10C shows classifier performance plotted in ROC space (representative curves shown), and the raw values are provided in Table 8.

The RF tree model was selected not only because it was superior in performance but also because it is intuitive to interpret. In RF, the features used in the classifier are easily attainable, compared to classifiers built on neural networks and support vector machines that require deconvolution steps for identification of relevant features. In the present study, the best number of features to construct each decision tree was 6 peptides (FIGS. 11A-11C and Table 9). It is important to note that the majority of discriminatory peptides are shared amongst the classifiers, indicating that the assay is able to measure a distinct quantitative pattern of each peptide, rather than assessing binary states (on/off). This allows for three possible scenarios of the modification landscape on each peptide in tauopathies 1) the same modification(s) is/are present in each disease, but at different stoichiometries, 2) the same modifications are present with similar stoichiometries, but additional unique modifications exist, and 3) different modifications are present in each disease with specific stoichiometries.

Most disease-related tau modifications mapped so far by us and others, in particular phosphorylations, cluster around the MT binding region, namely in the proline-rich region and the C-terminal tail. Several of these phosphorylation sites have been recognized as 'pathological', as the detection of their epitopes using antibodies is an indicator for tau-mediated neurodegeneration. Some of these antibodies are widely used in diagnostic practices for the evaluation of tauopathies, such as AT8 and AT100, both targeting sites in the proline-rich region (pS202/T205 and pT212/S214). Importantly, in our study, the majority of the peptides selected as discriminating features are located in the MT-binding repeat region of tau, including exon 10, indicating that this region harbors molecular characteristics that are unique to each tauopathy (FIG. 8D). Interestingly, most of the acetylation and ubiquitination sites identified so far and also in our cumulative PTM analysis are located inside the MT binding region (FIG. 6C). This strongly suggests that acetylated and ubiquitinated tau may serve as biomarker to distinguish different tauopathies, while phosphorylation on characteristic sites is rather a common marker for tau pathology. In fact, acetylation and ubiquitination have recently received increased attention as they may play a central role in tau-mediated neurodegeneration. Furthermore, PiD as well as AGD, another less well-understood tauopathy, have been shown to lack acetylation on specific sites in the first MT binding repeat compared to other tauopathies (acLys280 and acLys274, respectively).[50,99,100] Furthermore, ubiquitination in glial lesions has also been reported to be useful for distinguishing between various types of tauopathies.

Another post-translational modification that has been recently linked to the early pathogenesis of AD and other tauopathies is proteolytic cleavage, in particular at the C-terminus of tau, i.e. Glu391 and Asp421. Notably in our study, the two peptides covering these sites contribute to all classifiers (the former to CBD and PSP, the latter to ctrl, PiD and AD). This could imply that in addition to the above-mentioned PTMs, C-terminal truncation could be used to biochemically classify tauopathies, as suggested by previous studies.[104] Furthermore, a recent study reported that in sarkosyl insoluble tau, the MT-binding region harbors distinct conformational modifications and protease-resistant fragments that are different among tauopathies.

Apart from PTMs, disturbances in tau isoform homeostasis have been implicated to form an important mechanistic basis in tauopathies, in particular the alternative splicing of exon 10, which is also located in the MT-binding region. Exon 10 encodes for the second of the four MT binding repeats, thus its alternative splicing produces two isoforms, containing either 3 MT binding repeats (3R-tau) or 4 MT binding repeats (4R-tau). Under physiological conditions, 3R and 4R-tau exist in an approximate 1:1 ratio and in AD, both isoforms are equally incorporated into tangles. In contrast, in CBD and PSP brains predominantly 4R-tau is deposited inside neuronal and glial lesions, whereas 3R-tau isoforms preferentially accumulate in PiD. Consistent with this, for CBD and PSP the three 4R-tau specific peptides that cover the exon 10 sequence in our assay were significantly enriched compared to control (FIG. 9B). In addition, these peptides were selected by the built classifiers as discriminatory features in each disease category under study (FIG. 8D).

TABLE 1

Peptides quantified by FLEXiTau assay and Corresponding PTMs

| Region | ID | Location [AA] Start | Location [AA] End | FLEXITau peptide | Peptide modification extent [%] P-tau | P-value | Peptide modification extent [%] PP-tau | P-value | PTM contributing to modification extent detected | PTM contributing to modification extent hypothesized |
|---|---|---|---|---|---|---|---|---|---|---|
| acidic | A | 6 | 23 | QEFEVMEDHAGTYGLGDR (SEQ ID NO: 1) | | | | | — | |
| | B | 24 | 44 | KDQGGYTMHQDQEGDTDAGLK (SEQ ID NO: 19) | 50.8 | * | 22.2 | * | — | Y29, T30, T39 |
| | C | 45 | 67 | ESPLQTPTEDGSEEPGSETSDAK (SEQ ID NO: 3) | 44.7 | * | 54.0 | ** | S68 | S46, T50, T52, S56 |
| | D | 68 | 87 | STPTAEDTAPLVDEGAPGK (SEQ ID NO: 4) | 19.9 | * | 33.4 | ** | S68, T76 | |
| | E | 88 | 126 | QAAAQPHTEIPEGTTAEEAGIGDTPSLEDEAAGHVTQAR (SEQ ID NO: 5) | | | 12.9 | | — | |
| proline-rich | F | 151 | 163 | IATPRGAAPPGQK (SEQ ID NO: 20) | 4.2 | | 20.1 | * | T153 | |
| | G | 164 | 174 | GQANATRIPAK (SEQ ID NO: 21) | 2.1 | | 3.0 | | T175 | |
| | H | 175 | 180 | TPPAPK (SEQ ID NO: 22) | 58.4 | ** | 67.4 | ** | T175, T181 | |
| | I1 | 181 | 190 | TPPSSGEPPK (SEQ ID NO: 6) | 59.1 | ** | 66.0 | ** | T181, S184 | |
| | I2 | 181 | 194 | TPPSSGEPPKSGDR (SEQ ID NO: 23) | 66.4 | ** | 82.3 | *** | T181, S184 | S195 |
| | J | 195 | 209 | SGYSSPGSPGTPGSR (SEQ ID NO: 7) | 86.1 | *** | 90.7 | ** | S199, S202, T205, S210 | S195 |
| | K1 | 210 | 221 | SRTPSLPTPPTR (SEQ ID NO: 24) | 69.7 | ** | 94.8 | ** | S210, T212, S214, T217 | |
| | K2 | 210 | 224 | SRTPSLPTPPTREPK (SEQ ID NO: 25) | 68.8 | * | 91.1 | ** | S210, T212, S214, T217 | |
| | K3 | 212 | 221 | TPSLPTPPTR (SEQ ID NO: 8) | 52.2 | ** | 80.1 | *** | T212, S214, T217 | |
| | K4 | 212 | 224 | TPSLPTPPTREPK (SEQ ID NO: 9) | 53.7 | ** | 88.0 | *** | T212, S214, T217 | |
| | L | 226 | 234 | VAVVRTPPK (SEQ ID NO: 26) | 90.6 | *** | 97.2 | *** | T231, S235 | |
| binding repeats | M | 243 | 254 | LQTAPVPMPDLK (SEQ ID NO: 10) | 9.2 | | 12.0 | | — | |
| | N | 260 | 267 | IGSTENLK (SEQ ID NO: 27) | 15.7 | * | 38.6 | ** | S262 | |
| | O | 275 | 280 | VQIINK (SEQ ID NO: 28) | 11.6 | | 9.0 | | — | |
| | P | 281 | 290 | KLDLSNVQSK (SEQ ID NO: 11) | 15.2 | | 13.2 | | — | |
| | Q | 299 | 317 | HVPGGGSVQIVYKPVDLSK (SEQ ID NO: 13) | 7.9 | | 10.2 | | — | |
| | R | 322 | 340 | CGSLGNIHHKPGGGQVEVK (SEQ ID NO: 29) | 12.4 | | 31.0 | * | S324 | |

TABLE 1-continued

Peptides quantified by FLEXiTau assay and Corresponding PTMs

| Region | ID | Location [AA] Start | End | FLEXITau peptide | Peptide modification extent [%] P-tau | P-value | PP-tau | P-value | PTM contributing to modification extent detected | hypothesized |
|---|---|---|---|---|---|---|---|---|---|---|
| | S | 341 | 347 | SEKLDFK (SEQ ID NO: 30) | 10.2 | | 6.4 | | — | |
| | T | 354 | 369 | IGSLDNITHVPGGGNK (SEQ ID NO: 14) | 1.8 | | 23.8 | * | S356 | |
| C-terminal | U | 376 | 383 | LTFRENAK (SEQ ID NO: 31) | | | | | — | |
| | V1 | 384 | 395 | AKTDHGAEIVYK (SEQ ID NO: 32) | 33.2 | * | 41.1 | * | S396 | |
| | V2 | 386 | 395 | TDHGAEIVYK (SEQ ID NO: 15) | 29.4 | * | 34.2 | * | S396 | |
| | W | 396 | 406 | SPVVSGDTSPR (SEQ ID NO: 16) | 84.1 | *** | 84.1 | *** | S396, S404 | |

TABLE 2

Summary of phosphorylated tau peptide species and phosphorylation sites detected in deP-tau, P-tau and PP-tau.

| PTM site AA | Site | Peptide species Sequence | Precursor MW | z | Peptide species detected deP-tau | P-tau | PP-tau | Site detected deP-tau | P-tau | PP-tau |
|---|---|---|---|---|---|---|---|---|---|---|
| S | 68/69 | STPTAEDVTAPLVDEGAPGK (SEQ ID NO: 4) | 2033.9055 | 2 | | x | x | | yes | yes |
| T | 76 | STPTAEDVTAPLVDEGAPGK (SEQ ID NO: 4) | 2033.9055 | 2 | | | x | | | yes |
| T | 153 | TKIATPR (SEQ ID NO: 33) | 865.4415 | 2 | | x | x | yes | yes | yes |
| | | TKIATPRGAAPPGQK (SEQ ID NO: 34) | 1571.8176 | 3 | | | x | | | |
| | | IATPR (SEQ ID NO: 35) | 636.2993 | 2 | | | x | | | |
| | | IATPRGAAPPGQK (SEQ ID NO: 20) | 1342.6716 | 2 | | x | x | | | |
| T | 175 | GQANATRIPAKTPPAPK (SEQ ID NO: 36) | 1796.9287 | 3 | | | x | | yes | yes |
| | | IPAKTPPAPK (SEQ ID NO: 37) | 1098.587 | 2 | | x | x | | | |
| | | TPPAPKTPPSSGEPPKSGDR (SEQ ID NO: 38) | 2081.9709 | 4 | | | x | | | |
| T/T | 175/181 | GQANATRIPAKTPPAPKTPPSSGEPPK (SEQ ID NO: 39) | 2854.3762 | 4 | | x | x | | yes | yes |
| | | IPAKTPPAPKTPPSSGEPPK (SEQ ID NO: 40) | 2156.0305 | 3 | | | x | | | |
| T | 181 | IPAKTPPAPKTPPSSGEPPK (SEQ ID NO: 40) | 2156.0305 | 3 | | x | x | yes | yes | yes |
| | | TPPAPKTPPSSGEPPK (SEQ ID NO: 41) | 1666.7997 | 3 | x | x | x | | | |
| | | TPPAPKTPPSSGEPPKSGDR (SEQ ID NO: 38) | 2081.9709 | 4 | | | x | | | |
| | | TPPSSGEPPK (SEQ ID NO: 6) | 1075.462 | 2 | | x | x | | | |
| | | TPPSSGEPPKSGDR (SEQ ID NO: 23) | 1490.6445 | 2 | | | x | | | |
| S | 184 | TPPAPKTPPSSGEPPKSGDR (SEQ ID NO: 38) | 2081.9709 | 4 | | x | x | | yes | yes |
| | | TPPAPKTPPSSGEPPK (SEQ ID NO: 41) | 1666.7997 | 3 | | | x | | | |
| S | 199 | SGYSSPGSPGTPGSR (SEQ ID NO: 7) | 1472.5914 | 2 | | x | x | | yes | yes |

TABLE 2-continued

Summary of phosphorylated tau peptide species and
phosphorylation sites detected in deP-tau, P-tau and PP-tau.

| PTM site | | Peptide species | | | Peptide species detected | | | Site detected | | |
|---|---|---|---|---|---|---|---|---|---|---|
| AA | Site | Sequence | Precursor MW | z | deP-tau | P-tau | PP-tau | deP-tau | P-tau | PP-tau |
| S | 202 | SGYSSPGSPGTPGSR (SEQ ID NO: 7) | 1472.5914 | 2 | | x | x | | yes | yes |
| T | 205 | SGYSSPGSPGTPGSR (SEQ ID NO: 7) | 1472.5914 | 2 | | x | x | | yes | yes |
| S | 210 | SRTPSLPTPPTR (SEQ ID NO: 24) | 1388.6807 | 2 | | x | x | | yes | yes |
| | | SRTPSLPTPPTREPK (SEQ ID NO: 25) | 1822.8362 | 3 | | x | | | | |
| T | 212 | SRTPSLPTPPTR (SEQ ID NO: 24) | 1388.6807 | 2 | | x | x | | yes | yes |
| | | SRTPSLPTPPTREPK (SEQ ID NO: 25) | 1822.8362 | 3 | | x | | | | |
| T + S | 212 + 214 | SRTPSLPTPPTREPK (SEQ ID NO: 25) | 1822.8362 | 3 | | x | x | | yes | yes |
| T + T | 212 + 217 | SRTPSLPTPPTREPK (SEQ ID NO: 25) | 1822.8362 | 3 | | | x | | | yes |
| S | 214 | SRTPSLPTPPTR (SEQ ID NO: 24) | 1388.6807 | 2 | | x | x | yes | yes | yes |
| | | SRTPSLPTPPTREPK (SEQ ID NO: 25) | 1822.8362 | 3 | | x | | | | |
| | | TPSLPTPPTR (SEQ ID NO: 8) | 1145.5465 | 2 | | x | x | | | |
| | | TPSLPTPPTREPK (SEQ ID NO: 9) | 1499.7394 | 3 | x | x | x | | | |
| T | 217 | SRTPSLPTPPTREPK (SEQ ID NO: 25) | 1822.8362 | 3 | x | x | | yes | yes | yes |
| | | TPSLPTPPTR (SEQ ID NO: 8) | 1145.5465 | 2 | | x | x | | | |
| | | TPSLPTPPTREPK (SEQ ID NO: 9) | 1499.7394 | 3 | x | x | x | | | |
| T | 231 | KVAVVRTPPK (SEQ ID NO: 42) | 1173.6621 | 2 | x | x | x | yes | yes | yes |
| | | KVAVVRTPPKSPSSAK (SEQ ID NO: 43) | 1730.9443 | 3 | x | x | x | | | |
| | | TPPKSPSSAK (SEQ ID NO: 44) | 1078.5077 | 2 | x | x | x | | | |
| | | VAVVRTPPKSPSSAK (SEQ ID NO: 45) | 1602.8481 | 3 | | x | x | | | |
| T + S | 231 + 235 | KVAVVRTPPKSPSSAK (SEQ ID NO: 43) | 1730.9443 | 3 | | x | x | | yes | yes |
| | | VAVVRTPPKSPSSAK (SEQ ID NO: 45) | 1602.8481 | 3 | | x | x | | | |
| S | 235 | TPPKSPSSAK (SEQ ID NO: 44) | 1078.5077 | 2 | | x | x | | yes | yes |
| | | VAVVRTPPKSPSSAK (SEQ ID NO: 45) | 1602.8481 | 3 | | x | x | | | |
| S | 262 | IGSTENLKHQPGGGK (SEQ ID NO: 46) | 1601.7526 | 3 | | x | | | yes | yes |
| | | SKIGSTENLK (SEQ ID NO: 47) | 1155.5531 | 2 | | x | x | | | |
| | | SKIGSTENLKHQPGGGK (SEQ ID NO: 48) | 1816.8882 | 4 | | x | x | | | |
| S | 293 | CGSKDNIK (SEQ ID NO: 49) | 1014.4178 | 2 | | | x | | | yes |
| S | 324 | CGSLGNIHHKPGGGQVEVK (SEQ ID NO: 29) | 2066.9736 | 3 | | x | x | | yes | yes |

TABLE 2-continued

Summary of phosphorylated tau peptide species and phosphorylation sites detected in deP-tau, P-tau and PP-tau.

| PTM site | | Peptide species | | | Peptide species detected | | | Site detected | | |
|---|---|---|---|---|---|---|---|---|---|---|
| AA | Site | Sequence | Precursor MW | z | deP-tau | P-tau | PP-tau | deP-tau | P-tau | PP-tau |
| S | 356 | IGSLDNITHVPGGGNK (SEQ ID NO: 14) | 1657.7806 | 2 | | | x | | | yes |
| | | DRVQSKIGSLDNITHVPGGGNK (SEQ ID NO: 50) | 2371.1626 | 4 | | | x | | | |
| | | KIGSLDNITHVPGGGNK (SEQ ID NO: 51) | 1785.8754 | 3 | | | x | | | |
| S | 396 | AKTDHGAEIVYKSPVVSGDTSPR (SEQ ID NO: 52) | 2493.2092 | 4 | | x | x | | yes | yes |
| | | TDHGAEIVYKSPVVSGDTSPR (SEQ ID NO: 53) | 2294.0759 | 3 | | x | x | | | |
| S + S | 396 + 404 | TDHGAEIVYKSPVVSGDTSPR (SEQ ID NO: 53) | 2294.0759 | 3 | | | | | yes | yes |
| S | 404 | AKTDHGAEIVYKSPVVSGDTSPR (SEQ ID NO: 52) | 2493.2092 | 4 | | x | x | | yes | yes |
| | | SPVVSGDTSPR (SEQ ID NO: 16) | 1180.509 | 2 | | x | x | | | |
| S | 422 | HLSNVSSTGSIDMVDSPQLATLADEVSASLAK (SEQ ID NO: 54) | 3322.6108 | 4 | | x | x | | yes | yes |

Two phosphorylation sites detected simultaneously on a peptide are indicated by '+', e.g. 212 + 214. Ambiguous assignment of sites is indicated by '/', e.g. 68/69. AA, amino acid; z, charge; MW, Molecular Weight (monoisotopic mass of the ion fragmented in this analysis)

TABLE 3

Summary of site occupancies for the quantified tau phosphorylation sites, in %. Shown are values for each biological replicate, the average and standard deviation (stdev).

| Site(s) | P-tau | | | | | PP-tau | | | | |
|---|---|---|---|---|---|---|---|---|---|---|
| | P-tau1 | P-tau2 | P-tau3 | mean | stdev | PP-tau1 | PP-tau2 | PP-tau3 | mean | stdev |
| unknown (peptide B) | 75.72 | 54.72 | 46.80 | 59.08 | 14.94 | 29.50 | 21.15 | 16.07 | 22.24 | 6.78 |
| S68 + T76 | 8.51 | 14.50 | 24.81 | 15.94 | 8.24 | 27.82 | 31.89 | 30.84 | 30.18 | 2.11 |
| T153 | 2.05 | 0.00 | 6.33 | 2.80 | 3.23 | 16.41 | 12.27 | 31.56 | 20.08 | 10.16 |
| T175 | 0.00 | 0.00 | 11.55 | 3.85 | 6.67 | 0.00 | 6.46 | 9.85 | 5.44 | 5.00 |
| T181 | 49.29 | 62.23 | 57.42 | 56.31 | 6.54 | 73.49 | 51.66 | 67.91 | 64.35 | 11.34 |
| S184 | 0.90 | 0.00 | 11.17 | 4.02 | 6.21 | 0.00 | 1.59 | 9.16 | 3.58 | 4.90 |
| unknown (S195?) | 2.07 | 12.52 | 7.34 | 7.31 | 5.23 | 13.74 | 25.04 | 10.07 | 16.28 | 7.80 |
| S199 + S202 + T205 | 77.63 | 38.76 | 68.94 | 61.78 | 20.40 | 75.62 | 31.92 | 77.36 | 61.63 | 25.75 |
| S210 | 6.11 | 28.33 | 16.71 | 17.05 | 11.12 | 5.71 | 22.44 | 10.30 | 12.82 | 8.64 |
| T212 + S214 + T217 | 62.19 | 36.92 | 57.47 | 52.19 | 13.44 | 84.13 | 69.66 | 86.61 | 80.13 | 9.15 |
| T231 + S235 | 89.04 | 89.03 | 93.70 | 90.59 | 2.69 | 97.79 | 95.30 | 98.56 | 97.22 | 1.71 |
| unknown (peptide M) | 64.28 | 17.97 | 2.98 | 28.41 | 31.96 | 15.50 | 17.01 | 7.17 | 13.23 | 5.30 |
| S262 | 14.29 | 17.39 | 15.28 | 15.65 | 1.58 | 40.77 | 29.95 | 45.06 | 38.59 | 7.79 |
| S324 | 0.00 | 30.09 | 7.97 | 12.69 | 15.59 | 32.48 | 14.96 | 28.59 | 25.34 | 9.20 |
| S356 | 0.00 | 20.60 | 1.83 | 7.47 | 11.40 | 24.45 | 13.45 | 33.60 | 23.83 | 10.09 |
| S396 | 24.70 | 39.50 | 29.78 | 31.33 | 7.52 | 33.94 | 31.86 | 47.23 | 37.68 | 8.34 |
| S404 | 53.58 | 47.72 | 56.93 | 52.74 | 4.66 | 57.05 | 59.60 | 47.49 | 54.71 | 6.38 |

TABLE 4

Patient demographics in entire cohort of 129 cases. Percentages refer to the proportion of cases from each brain bank in the entire cohort.

|  | AD | PSP | CBD | PiD | control | Total |
|---|---|---|---|---|---|---|
| Total number of patients | 28 | 29 | 22 | 21 | 29 | 129 |
| Age at death (years) | | | | | | |
| Mean (SD) | 77.7 (10.1) | 75.3 (7.9) | 71.2 (7.2) | 68.5 (9.6) | 75.0 (12.8) | 74.0 (10.2) |
| Range | 41-90 | 58-93 | 58-88 | 51-92 | 45-97 | 41-97 |
| PMI (hours)* | | | | | | |
| Mean (SD) | 13.4 (5.5) | 13.4 (4.9) | 11.5 (6.6) | 14.8 (6.2) | 16.5 (5.0) | 14.1 (5.7) |
| Range | 4.9-23.0 | 6.17-23.8 | 2.0-24 | 4.0-25.5 | 7.8-30.3 | 2.0-30.3 |
| Sex | | | | | | |
| (male:female) | 11:17 | 21:08 | 10:12 | 16:05 | 19:10 | 77:52:00 |
| Brain Bank | | | | | | |
| UCSF | 5 | 5 | 9 | 7 | 3 | 29 (22.5%) |
| UCLA | 14 | 15 | 0 | 5 | 17 | 51 (39.5%) |
| McLean | 9 | 9 | 5 | 7 | 9 | 39 (30.2%) |
| MIAMI | 0 | 0 | 1 | 2 | 0 | 3 (2.3%) |
| UMB | 0 | 0 | 7 | 0 | 0 | 7 (5.4%) |

*no PMI value was available for 5 cases (1 PSP, 3 CBD, 1 PiD)

TABLE 5

Patient demographics in training and testing set.

|  | AD | | PSP | | CBD | |
|---|---|---|---|---|---|---|
|  | Train | Test | Train | Test | Train | Test |
| Total number of patients | 14 | 14 | 15 | 14 | 12 | 10 |
| Age (years) | | | | | | |
| Mean | 79.1 | 76.4 | 73.3 | 77.5 | 70.3 | 72.3 |
| (SD) | (8.8) | (11.4) | (6.7) | (8.72) | (5.7) | (8.9) |
| Range | 61-90 | 41-89 | 58-84 | 65-93 | 63-83 | 58-88 |
| PMI (hours) | | | | | | |
| Mean | 12.5 | 14.3 | 11.6 | 15.3 | 10.3 | 12.5 |
| (SD) | (5.1) | (5.9) | (4.1) | (5.2) | (6.2) | (7.1) |
| Range | 6.5-20.6 | 4.9-23.0 | 6.17-20.5 | 7.0-23.8 | 4.0-21.9 | 2.0-24.0 |
| Sex | | | | | | |
| (male:female) | 7:7 | 4:10 | 11:4 | 10:4 | 5:7 | 5:5 |
| Brain Bank | | | | | | |
| UCSF | 5 | 0 | 5 | 0 | 9 | 0 |
| UCLA | 6 | 8 | 8 | 7 | 0 | 0 |
| McLean | 3 | 6 | 2 | 7 | 2 | 3 |
| MIAMI | 0 | 0 | 0 | 0 | 0 | 1 |
| UMB | 0 | 0 | 0 | 0 | 1 | 6 |

|  | PiD | | control | | Total | |
|---|---|---|---|---|---|---|
|  | Train | Test | Train | Test | Train | Test |
| Total number of patients | 12 | 9 | 15 | 14 | 68 | 61 |
| Age (years) | | | | | | |
| Mean | 67.8 | 69.4 | 70.5 | 79.9 | 72.4 | 75.7 |
| (SD) | (9.5) | (10.4) | (13.9) | (9.7) | (10.0) | (10.2) |
| Range | 51-84 | 58-92 | 45-90 | 59-97 | 45-90 | 41-97 |
| PMI (hours) | | | | | | |
| Mean | 17.1 | 11.9 | 15.7 | 17.4 | 13.6 | 14.6 |
| (SD) | (5.4) | (6.1) | (6.0) | (3.6) | (5.7) | (5.7) |
| Range | 10.2-25.5 | 4.0-20.0 | 7.8-30.3 | 10.5-22.2 | 4.0-30.3 | 2.0-24.0 |

TABLE 5-continued

Patient demographics in training and testing set.

Sex

| | | | | | | |
|---|---|---|---|---|---|---|
| (male:female) | 9:3 | 7:2 | 8:7 | 3:21 | 40:28 | 37:24 |

Brain Bank

| | | | | | | |
|---|---|---|---|---|---|---|
| UCSF | 7 | 0 | 3 | 0 | 29 | 0 |
| UCLA | 0 | 5 | 9 | 8 | 23 | 28 |
| McLean | 5 | 2 | 3 | 6 | 15 | 24 |
| MIAMI | 0 | 2 | 0 | 0 | 0 | 3 |
| UMB | 0 | 0 | 0 | 0 | 1 | 6 |

TABLE 6

Final diagnostic performance of optimized classifier on independent testing sets.

| Performance (%) | OOB | Accuracy | Sensitivity | Specificity | AUC |
|---|---|---|---|---|---|
| AD | 1.5 | 93.9 | 88.2 | 96.8 | 92.6 |
| PSP | 16.6 | 81.6 | 71.4 | 83.3 | 77.4 |
| CBD | 9.6 | 95.9 | 90.0 | 97.4 | 93.7 |
| PiD | 5.2 | 91.8 | 83.3 | 93.0 | 88.2 |
| ctrl | 8.7 | 95.9 | 92.3 | 97.2 | 94.9 |
| ave | 8.3 | 91.8 | 85.1 | 93.6 | 89.3 |

Table showing diagnostic performance of Random Forest trained with on the entire training set and applied to the independent test set after excluding the cases with asymptomatic or atypical pathology (11 cases), assigning two different diseases to the cases where comorbidity was described (4 cases) and assigning the corrected diagnosis for misdiagnosed cases (2 cases) (Table 12).

TABLE 7

PTMs identified on tau isolated from AD patients

| Modification Site | Modification | # AD Cases | #OGF Runs | Known tau Modification$ |
|---|---|---|---|---|
| T111* | Phospho | | 1 | Yes |
| S113 | Phospho | | 1 | Yes |
| T175 | Phospho | 2 | 2 | Yes |
| K180 | Ubiq | | 1 | |
| T175/T181/S191* | Double Phospho | 1 | 1 | |
| T181 | Phospho | 16 | 2 | Yes |
| S184* | Phospho | 4 | | Yes |
| S191 | Phospho | 7 | 1 | Yes |
| S198* | Phospho | 2 | | Yes |
| S199* | Phospho | 3 | 2 | Yes |
| S202 | Phospho | 4 | 2 | Yes |
| T212/T217 | Double Phospho | 1 | | |
| T212 | Phospho | 1 | 1 | Yes |
| S214 | Phospho | 9 | 1 | Yes |
| T217 | Phospho | 13 | 2 | Yes |
| T231 | Phospho | 15 | 2 | Yes |
| T231/K240 | Phos/Ubiq | | 1 | |
| T231/S235/S237* | Double Phospho | 12 | 2 | |
| S235 | Phospho | 2 | | Yes |
| Q244 | Methyl | | 1 | |
| K254 | Ubiq | 15 | 2 | Yes |
| K257 | Ubiq | 1 | | Yes |
| K259 | Ubiq | 5 | 2 | |
| S262 | Phospho | 15 | 2 | Yes |
| K267 | Ubiq | 3 | 1 | |
| K267 | Acetyl | | 2 | |
| N279 | Methyl | | 1 | |
| K281 | Ubiq | 2 | | |
| D283 | Methyl | | 1 | |
| S285 | Phospho | | 1 | |
| S289 | Phospho | | 1 | Yes |
| H299 | Methyl | | 1 | |
| S305 | Phospho | 7 | 1 | Yes |
| Q307 | Methyl | | 1 | |
| Y310 | Hex | | 1 | |
| K311 | Ubiq | 16 | 2 | Yes |
| K311/K317 | Double Ubiq | 3 | 2 | |
| K311 | Acetyl | 11 | 2 | |
| K311 | Methyl | | 1 | |
| D314 | Methyl | | 1 | |
| S316 | Phospho | | 1 | |
| S316 | Methyl | | 1 | |
| S316 | Acetyl | | 1 | |
| K317 | Ubiq | 15 | 2 | Yes |
| K317 | Acetyl | | 1 | |
| S324 | Methyl | 4 | 1 | |
| S324 | Phospho | 1 | | |
| S324 | Acetyl | | 1 | |
| L325 | Methyl | | 1 | |
| N327* | Methyl | | 1 | |
| K331 | Acetyl | | 2 | |
| K340 | Acetyl | | 1 | |
| E342 | Methyl | | 1 | |
| K343 | Ubiq | 1 | 1 | |
| K353 | Acetyl | | 2 | |
| K353 | Trimethyl | 3 | 1 | |
| S356 | Phospho | 3 | 2 | Yes |
| S356 | Methyl | | 1 | |
| L357* | Methyl | | 1 | |
| N359 | Hex | | 1 | |
| T361 | Phospho | 2 | | |
| K369 | Acetyl | 10 | 2 | |
| K375 | Acetyl | 2 | | |
| T386 | Phospho | 2 | 2 | |
| H388 | Methyl | | 1 | |
| K395 | Ubiq | | 2 | |
| S396 | NeuAc | | 1 | |
| S396/S400/T403/S404* | Double Phospo | 4 | 1 | |
| S396 | Phospho | 12 | 2 | Yes |
| S400 | Phospho | 3 | 2 | Yes |
| T403* | Phospho | 12 | 2 | Yes |
| S404 | Phospho | 11 | 2 | Yes |
| S412/S416/S422* | Phospho/dHex | 3 | | Yes (phos) |
| S422* | NeuGc | 3 | | |
| S422 | Phospho | 1 | | Yes |

*Assignment is inconclusive i.e., modification could also be on a nearby amino acid
$Refers to previously published information of Human brain derived-tau Ubiq: ubiquitination;
Phospho: phosphorylation;
dHex, NeuGc, NeuAc: glycosylation;
Methyl: methylation;
Acetyl: acetylation

TABLE 8

Diagnostic performance of several supervised machine-learning methods.

| | | Classifier | | | | | | | | | | | | |
|---|---|---|---|---|---|---|---|---|---|---|---|---|---|---|
| | | RF | | Nnet | | KNN | | LVQ | | LDA | | SVM | | average |
| Performance | | ac (%) | AUC (%) | ac (%) | AUC (%) | ac (%) | AUC (%) | ac (%) | AUC (%) | ac (%) | AUC (%) | ac (%) | AUC (%) | ac (%) | AUC (%) |
| AD | mean | 89.2 | 93.0 | 86.2 | 90.5 | 85.1 | 90.2 | 85.2 | 90.3 | 80.4 | 81.8 | 91.7 | 94.5 | 86.3 | 90.1 |
| | SD | 4.3 | 2.8 | 6.2 | 4.1 | 5.7 | 3.7 | 4.9 | 3.2 | 9.4 | 10.0 | 1.1 | 0.7 | 3.9 | 4.4 |
| PSP | mean | 76.2 | 77.3 | 72.0 | 73.0 | 74.3 | 75.9 | 73.4 | 73.5 | 66.3 | 67.1 | 77.8 | 78.2 | 73.3 | 74.2 |
| | SD | 2.8 | 4.8 | 12.0 | 7.3 | 2.9 | 6.7 | 5.8 | 7.5 | 7.7 | 9.4 | 3.9 | 5.1 | 4.0 | 4.0 |
| CBD | mean | 91.8 | 91.7 | 92.5 | 92.2 | 70.4 | 82.9 | 81.3 | 89.2 | 77.9 | 87.2 | 91.8 | 88.2 | 84.3 | 88.6 |
| | SD | 4.3 | 3.7 | 1.7 | 5.2 | 14.9 | 8.6 | 14.0 | 8.1 | 6.9 | 4.0 | 1.3 | 5.8 | 9.2 | 3.4 |
| PiD | mean | 79.3 | 59.8 | 79.1 | 59.7 | 72.8 | 62.4 | 77.5 | 63.7 | 67.3 | 53.6 | 78.0 | 57.3 | 75.7 | 59.4 |
| | SD | 3.6 | 6.7 | 3.9 | 9.5 | 4.0 | 4.3 | 5.8 | 7.5 | 7.4 | 11.0 | 3.9 | 6.4 | 4.7 | 3.6 |
| Ctrl | mean | 86.5 | 86.2 | 87.8 | 87.5 | 81.5 | 87.5 | 80.5 | 84.3 | 83.6 | 76.7 | 84.6 | 83.7 | 84.1 | 84.3 |
| | SD | 5.1 | 3.1 | 6.4 | 6.8 | 4.4 | 2.4 | 6.5 | 5.1 | 4.8 | 7.7 | 6.3 | 6.4 | 20.8 | 4.0 |
| average | mean | 84.6 | 81.6 | 83.5 | 80.6 | 76.8 | 79.8 | 79.6 | 80.2 | 75.1 | 73.3 | 84.7 | 80.4 | 80.7 | 79.3 |
| | SD | 4.0 | 4.2 | 6.0 | 6.6 | 6.4 | 5.1 | 7.4 | 6.3 | 7.2 | 8.4 | 3.3 | 4.9 | 4.2 | 3.0 |

Table showing diagnostic Performance of RF, Nnet, KNN, LVQ, LDA, and SVM in correctly predicting each category from all others was assessed by accuracy (ac) and area under the curve (AUC) of the ROC curve. Mean and SD of ten models (trained with different undersampled subsets of the reference category) are shown for each disease category.

TABLE 9

Optimization of number of split features in Random Forest classification.

| | | Number of splitter variables | | | | | | | | | | | | | | |
|---|---|---|---|---|---|---|---|---|---|---|---|---|---|---|---|---|
| | | 3 | | 4 | | 5 | | 6 | | 7 | | 8 | | 9 | | average |
| Performance | | ac (%) | AUC (%) | ac (%) | AUC (%) | ac (%) | AUC (%) | ac (%) | AUC (%) | ac (%) | AUC (%) | ac (%) | AUC (%) | ac (%) | AUC (%) | ac (%) | AUC (%) |
| AD | mean | 93.3 | 94.4 | 91.8 | 94.3 | 92.8 | 95.3 | 92.1 | 94.7 | 91.6 | 94.3 | 91.8 | 94.5 | 91.8 | 94.5 | 92.2 | 94.6 |
| | SD | 2.6 | 4.2 | 2.8 | 2.8 | 3.1 | 2.0 | 3.0 | 1.6 | 3.1 | 1.7 | 3.1 | 1.6 | 3.2 | 1.7 | 0.6 | 0.4 |
| PSP | mean | 78.1 | 76.1 | 78.9 | 77.3 | 78.4 | 77.0 | 79.2 | 77.7 | 78.5 | 77.7 | 77.8 | 76.9 | 78.2 | 77.2 | 78.4 | 77.1 |
| | SD | 4.2 | 4.2 | 3.9 | 3.3 | 2.7 | 2.3 | 4.4 | 4.8 | 2.7 | 2.3 | 4.3 | 4.1 | 3.0 | 0.5 | 0.6 | 0.6 |
| CBD | mean | 79.1 | 86.0 | 86.1 | 86.6 | 86.6 | 90.7 | 87.6 | 91.1 | 88.3 | 90.3 | 87.5 | 90.9 | 87.9 | 63.1 | 86.2 | 89.3 |
| | SD | 16.8 | 18.2 | 11.9 | 18.5 | 11.9 | 6.8 | 6.3 | 6.9 | 6.5 | 7.5 | 6.1 | 6.9 | 6.7 | 10.0 | 3.2 | 2.3 |
| PiD | mean | 79.0 | 63.1 | 79.6 | 64.0 | 78.7 | 61.2 | 78.9 | 60.2 | 78.1 | 59.4 | 77.8 | 58.9 | 78.2 | 59.2 | 78.6 | 61.1 |
| | SD | 6.6 | 10.0 | 4.5 | 8.9 | 3.3 | 6.3 | 2.7 | 3.9 | 2.3 | 5.3 | 3.5 | 5.4 | 3.8 | 6.3 | 0.6 | 2.1 |
| Ctrl | mean | 89.0 | 87.2 | 89.6 | 88.1 | 89.3 | 88.0 | 89.3 | 87.9 | 89.4 | 88.1 | 89.8 | 88.4 | 89.4 | 87.8 | 89.4 | 87.9 |
| | SD | 6.2 | 2.9 | 4.7 | 2.0 | 3.9 | 2.1 | 4.1 | 2.0 | 3.9 | 2.1 | 4.0 | 2.0 | 4.6 | 2.8 | 0.2 | 0.4 |
| ave | mean | 83.7 | 81.4 | 85.2 | 82.1 | 85.2 | 82.5 | 85.4 | 82.3 | 85.2 | 82.0 | 84.9 | 81.9 | 85.1 | 76.3 | 84.9 | 82.0 |
| | SD | 7.3 | 7.9 | 5.6 | 7.1 | 5.0 | 3.9 | 4.1 | 3.9 | 3.8 | 3.8 | 4.2 | 4.0 | 4.3 | 4.6 | 0.6 | 0.4 |

Table showing diagnostic performance of Random Forest trained with distinct number of split variables for the decision trees. Mean and SD of ten models (trained with different under sampled subsets of the reference category) are shown for each disease category.

TABLE 10

Evaluation of absolute abundance of tau as diagnostic feature.

| | | Performance | | Chosen features | | | | | |
|---|---|---|---|---|---|---|---|---|---|
| Abundance | | ac | AUC | (descending importance) | | | | | |
| feature: | | (%) | (%) | 1 | 2 | 3 | 4 | 5 | 6 |
| AD | excluded | 93.3 | 95.6 | 17 | 14 | 8 | 3 | 10 | 9 |
| | included | 92.1 | 94.9 | 14 | 18 | 17 | 13 | 8 | 10 |
| PSP | excluded | 83.1 | 84.0 | 15 | 12 | 8 | 13 | 11 | 3 |
| | included | 79.8 | 65.4 | 18 | 15 | 12 | 13 | 7 | 11 |
| CBD | excluded | 93.3 | 89.1 | 5 | 13 | 12 | | | |
| | included | 95.5 | 86.9 | 12 | 5 | 11 | 9 | 13 | 7 |
| PiD | excluded | 83.1 | 72.6 | 13 | 12 | 9 | 17 | 14 | 5 |
| | included | 80.9 | 65.4 | 13 | 17 | 18 | 9 | 12 | 14 |
| Ctrl | excluded | 91.0 | 89.2 | 17 | 14 | 13 | 8 | 10 | 2 |
| | included | 93.3 | 90.7 | 17 | 14 | 10 | 13 | 18 | 7 |
| ave | excluded | 94.4 | 86.1 | | | | | | |
| | included | 93.5 | 80.6 | | | | | | |

Table showing diagnostic performance when absolute abundance of tau in each sample is included, or excluded as 18th feature. The six split features chosen by the RF classifier in each category are shown in the order of descending importance. Feature Identifiers:

1 =
(SEQ ID NO: 1)
QEFEVMEDHAGTYGLGDR;

2 =
(SEQ ID NO: 55)
DQGGYTMHQDQEGDTDAGL;

3 =
(SEQ ID NO: 3)
ESPLQTPTEDGSEEPGSETSDAK;

4 =
(SEQ ID NO: 4)
STPTAEDVTAPLVDEGAPGK;

5 =
(SEQ ID NO: 5)
QAAAQPHTEIPEGTTAEEAGIGDTPSLEDEAAGHVTQAR;

6 =
(SEQ ID NO: 6)
TPPSSGEPPK;

7 =
(SEQ ID NO: 7)
SGYSSPGSPGTPGSR;

8 =
(SEQ ID NO: 8)
TPSLPTPPTR;

9 =
(SEQ ID NO: 9)
TPSLPTPPTREPK;

10 =
(SEQ ID NO: 10)
LQTAPVPMPDLK;

11 =
(SEQ ID NO: 11)
KLDLSNVQSK;

12 =
(SEQ ID NO: 12)
LDLSNVQSK;

13 =
(SEQ ID NO: 13)
HVPGGGSVQIVYKPVDLSK;

14 =
(SEQ ID NO: 14)
IGSLDNITHVPGGGNK;

15 =
(SEQ ID NO: 56)
TDHGAEIVYKSPVVSGDTSPR;

17 =
(SEQ ID NO: 54)
HLSNVSSTGSIDMVDSPQLATLADEVSASLAK;

18 =
abundance

TABLE 11

Initial diagnostic performance of optimized classifier on independent testing sets.

| Performance (%) | | OOB | Accuracy | Sensitivity | Specificity | AUC |
|---|---|---|---|---|---|---|
| AD | Train | 1.5 | 86.9 | 78.6 | 89.4 | 84.0 |
| PSP | Train | 16.6 | 70.5 | 50.0 | 76.6 | 63.3 |
| CBD | Train | 9.6 | 93.4 | 80.0 | 96.1 | 88.0 |
| PiD | Train | 5.2 | 86.9 | 55.6 | 92.3 | 73.9 |
| ctrl | Train | 8.7 | 82.0 | 85.7 | 80.9 | 83.3 |
| ave | Train | 8.3 | 83.9 | 70.0 | 87.0 | 78.5 |

Table showing diagnostic performance of Random Forest trained with on the entire training set and applied to the entire independent test set, including asymptomatic and atypical samples.

TABLE 12

FN and/or FP assignments in the test set that could be explained by underlying pathological characteristics.

| Case # | Category | Brain bank | FN | FP | FP in category: | Details from pathology reports and clinical informaion | Explanation | Hypothesized diagnosis | Diagnosis for final testing |
|---|---|---|---|---|---|---|---|---|---|
| 1 | PSP | Harvard | yes | yes | AD | early AD as secondary pathological diagnosis | co-occurring pathology | PSP + AD | re-assign to both |
| 2 | PiD | UCLA | no | yes | AD | AD pathological changes | co-occurring pathology | AD + PiD | re-assign to both |
| 3 | PiD | UCLA | no | yes | AD | AD pathological changes | co-occurring pathology | AD + PiD | re-assign to both |
| 4 | PiD | UCLA | no | yes | AD | AD pathological changes | co-occurring pathology | AD + PiD | re-assign to both |
| 5 | PSP | Harvard | yes | yes | CBD | unusually severe, Reevaluation by IHC | wrong diagnosis | CBD | re-assign to both |
| 6 | CBD | Maryland | yes | yes | PSP, ctrl | atypical. Reevaluation by IHC | wrong diagnosis | uncertain | exclude |
| 7 | AD | UCLA | yes | yes | PSP | "probable" AD, minimal to mild NFT pathology | uncertain pathological diagnosis | PSP | exclude |
| 8 | PSP | UCLA | no | yes | ctrl | "atypical" | uncertain pathological diagnosis | PSP | exclude |
| 9 | PiD | UCLA | yes | yes | PSP, ctrl | no Pick bodies or any other pathological evidence for PiD | uncertain pathological diagnosis | non-tau FTP | exclude |
| 10 | ctrl | UCLA | yes | no | — | "recent history of dementia" | control with reported dementia | uncertain pathology | exclude |
| 11 | PiD | Miami | yes | yes | ctrl | TDP-43 positive | non-tau case | FTP-TDP (TDP-43) | exclude |
| 12 | PSP | UCLA | yes | yes | ctrl | no pathology in parietal cortex | spared cortex | PSP | exclude |
| 13 | PSP | Harvard | yes | yes | PiD, ctrl | Probable lack of parietal cortex tau | spared cortex | PSP | exclude |

TABLE 12-continued

FN and/or FP assignments in the test set that could be explained by underlying pathological characteristics.

| Case # | Category | Brain bank | FN | FP | FP in category: | Details from pathology reports and clinical informaion | Explanation | Hypothesized diagnosis | Diagnosis for final testing |
|---|---|---|---|---|---|---|---|---|---|
| 14 | PSP | Harvard | yes | no | — | Probable lack of parietal cortex tau | spared cortex | PSP | exclude |
| 15 | PSP | Harvard | yes | yes | ctrl | Probable lack of parietal cortex tau | spared cortex | PSP | exclude |
| 16 | PSP | UCLA | no | yes | ctrl | spared cortex | spared cortex | PSP | exclude |

For the final testing, samples with confirmed co-occurring pathologies were re-assigned to both categories (Case #1-4).
Misdiagnosed samples were re-assigned to the correct category (Case # 5) or excluded, if correct diagnosis unknown (Case #6).
Samples with asymptomatic or atypical pathologies were excluded from the final testing (Case #7-17).
TDP-43, TAR DNA-binding protein 43;
ICH, Immunohistochemistry

TABLE 13

Mis-assigned samples in final testing. Hypothesis for the cause of misclassification is given

| Case # | Category | Brain bank | FN | FP | FP in category | Details from pathology reports | Explanation | Hypothesized diagnosis | True misclassification? |
|---|---|---|---|---|---|---|---|---|---|
| 1 | ctrl | Harvard | yes | yes | PSP | — | unexplained | ctrl | yes |
| 2 | ctrl | Harvard | no | yes | PSP | — | ctrl TP in ctrl classifier | ctrl | |
| 3 | ctrl | Harvard | no | yes | PSP | — | ctrl TP in ctrl classifier | ctrl | |
| 4 | ctrl | UCLA | no | yes | PSP | — | ctrl TP in ctrl dassifier | ctrl | |
| 5 | ctrl | UCLA | no | yes | PSP | — | ctrl TP in ctrl classifier | ctrl | |
| 6 | ctrl | UCLA | no | yes | PSP | — | ctrl TP in ctrl classifier | ctrl | |
| 7 | ctrl | UCLA | no | yes | PSP | — | ctrl TP in ctrl classifier | ctrl | |
| 8 | PSP | UCLA | yes | yes | CBD | — | potential misdiagnosis | PSP | |
| 9 | PiD | Miami | no | yes | AD | cause of death endstage AD | potential co-occurring pathology | AD + PiD | |
| 10 | AD | UCLA | yes | yes | ctrl | "definite AD" | unexplained | AD | yes |
| 11 | AD | UCLA | yes | yes | PiD | "definite AD" | unexplained | AD | yes |
| 12 | PiD | Harvard | yes | no | no FP | many Pick bodies | unexplained | PiD | yes |
| 13 | CBD | Maryland | yes | yes | PiD | — | potential misdiagnosis | PiD | |
| 14 | ctrl | Harvard | no | yes | PiD | — | unexplained | ctrl | yes |

TABLE 14

Fractions of Unmodified Peptides for Different Tauopathies

| | AD | CBD | PiD | PSP | ctrl |
|---|---|---|---|---|---|
| QEFEVMEDHAGTYGLGDR (SEQ ID NO: 1) | | | 0.710 ± 0.120 | | |
| ESPLQTPTEDGSEEPGSETSDAK (SEQ ID NO: 3) | | | | 0.170 ± 0.063 | |
| STPTAEDVTAPLVDEGAPGK (SEQ ID NO: 4) | | 0.018 ± 0.007 | | | |
| SGYSSPGSPGTPGSR (SEQ ID NO: 7) | | | | 0.373 ± 0.139 | |
| TPSLPTPPTR (SEQ ID NO: 8) | 0.074 ± 0.039 | | | 0.534 ± 0.151 | 0.558 ± 0.101 |
| LQTAPVPMPDLK (SEQ ID NO: 10) | 1.00 ± 0.109 | | 1.00 ± 0.074 | | 0.801 ± 0.101 |
| KLDLSNVQSK (SEQ ID NO: 11) | 0.144 ± 0.049 | 0.558 ± 0.144 | | 0.356 ± 0.079 | |
| LDLSNVQSK (SEQ ID NO: 12) | | 1.00 ± 0.207 | 0.421 ± 0.108 | 0.745 ± 0.230 | 0.515 ± 0.118 |

TABLE 14-continued

Fractions of Unmodified Peptides for Different Tauopathies

| | AD | CBD | PiD | PSP | ctrl |
|---|---|---|---|---|---|
| HVPGGGSVQIVYKPVD LSK (SEQ ID NO: 13) | 0.575 ± 0.142 | 0.843 ± 0.174 | 0.215 ± 0.143 | | 0.282 ± 0.039 |
| IGSLDNITHVPGGGNK (SEQ ID NO: 14) | 1.00 ± 0.159 | 0.615 ± 0.160 | 0.846 ± 0.098 | | 0.374 ± 0.066 |
| TDHGAEIVYK (SEQ ID NO: 15) | | 0.277 ± 0.168 | | 0.759 ± 0.165 | |
| HLSNVSSTGSIDMVDS PQLATLADEVSASLAK (SEQ ID NO: 54) | 0.024 ± 0.012 | | 0.333 ± 0.104 | | 0.903 ± 0.327 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Avila, J., Lucas, J. J., Perez, M., and Hernandez, F. (2004) Role of tau protein in both physiological and pathological conditions. Physiological reviews 84, 361-384
2. Dixit, R., Ross, J. L., Goldman, Y. E., and Holzbaur, E. L. F. (2008) Differential regulation of dynein and kinesin motor proteins by tau. Science (New York, N.Y.) 319, 1086-1089
3. Lee, V. M., Goedert, M., and Trojanowski, J. Q. (2001) Neurodegenerative tauopathies. Annual review of neuroscience 24, 1121-1159
4. Goedert, M., and Spillantini, M. G. (2011) Pathogenesis of the tauopathies. Journal of Molecular Neuroscience 45, 425-431
5. Alonso, A., Zaidi, T., Novak, M., Grundke-Iqbal, I., and Iqbal, K. (2001) Hyperphosphorylation induces self-assembly of tau into tangles of paired helical filaments/straight filaments. Proc Natl Acad Sci USA 98, 6923-6928
6. Kopke, E., Tung, Y. C., Shaikh, S., Alonso, A. C., Iqbal, K., and Grundke-Iqbal, I. (1993) Microtubule-associated protein tau. Abnormal phosphorylation of a non-paired helical filament pool in Alzheimer disease. J Biol Chem 268, 24374-24384
7. Schneider, A., Biernat, J., von Bergen, M., Mandelkow, E., and Mandelkow, E. M. (1999) Phosphorylation that detaches tau protein from microtubules (Ser262, Ser214) also protects it against aggregation into Alzheimer paired helical filaments. Biochemistry 38, 3549-3558
8. Delobel, P., Flament, S., Hamdane, M., Mailliot, C., Sambo, A. V., Begard, S., Sergeant, N., Delacourte, A., Vilain, J. P., and Buee, L. (2002) Abnormal Tau phosphorylation of the Alzheimer-type also occurs during mitosis. J Neurochem 83, 412-420
9. Min, S. W., Cho, S. H., Zhou, Y., Schroeder, S., Haroutunian, V., Seeley, W. W., Huang, E. J., Shen, Y., Masliah, E., Mukherjee, C., Meyers, D., Cole, P. A., Ott, M., and Gan, L. (2010) Acetylation of tau inhibits its degradation and contributes to tauopathy. Neuron 67, 953-966
10. Irwin, D. J., Cohen, T. J., Grossman, M., Arnold, S. E., Xie, S. X., Lee, V. M., and Trojanowski, J. Q. (2012) Acetylated tau, a novel pathological signature in Alzheimer's disease and other tauopathies. Brain: a journal of neurology 135, 807-818
11. Cohen, T. J., Guo, J. L., Hurtado, D. E., Kwong, L. K., Mills, I. P., Trojanowski, J. Q., and Lee, V. M. Y. (2011) The acetylation of tau inhibits its function and promotes pathological tau aggregation. Nature Communications 2, 252
12. Iqbal, K., and Grundke-Iqbal, I. (1991) Ubiquitination and abnormal phosphorylation of paired helical filaments in Alzheimer's disease. Molecular Neurobiology 5, 399-410
13. Cripps, D., Thomas, S. N., Jeng, Y., Yang, F., Davies, P., and Yang, A. J. (2006) Alzheimer disease-specific conformation of hyperphosphorylated paired helical filament-Tau is polyubiquitinated through Lys-48, Lys-11, and Lys-6 ubiquitin conjugation. The Journal of biological chemistry 281, 10825-10838
14. Thomas, S. N., Funk, K. E., Wan, Y., Liao, Z., Davies, P., Kuret, J., and Yang, A. J. (2012) Dual modification of Alzheimer's disease PHF-tau protein by lysine methylation and ubiquitylation: a mass spectrometry approach. Acta Neuropathologica 123, 105-117
15. Wang, J. Z., Grundke-Iqbal, I., and Iqbal, K. (1996) Glycosylation of microtubule-associated protein tau: an abnormal posttranslational modification in Alzheimer's disease. Nature Medicine 2, 871-875
16. Takahashi, M., Tsujioka, Y., Yamada, T., Tsuboi, Y., Okada, H., Yamamoto, T., and Liposits, Z. (1999) Glycosylation of microtubule-associated protein tau in Alzheimer's disease brain. Acta Neuropathologica 97, 635-641
17. Ballatore, C., Lee, V. M.-Y., and Trojanowski, J. Q. (2007) Tau-mediated neurodegeneration in Alzheimer's disease and related disorders. Nature Reviews Neuroscience 8, 663-672
18. Martin, L., Latypova, X., Wilson, C. M., Magnaudeix, A., Perrin, M.-L., Yardin, C., and Terro, F. (2013) Tau protein kinases: involvement in Alzheimer's disease. Ageing Research Reviews 12, 289-309
19. Duka, V., Lee, J. H., Credle, J., Wills, J., Oaks, A., Smolinsky, C., Shah, K., Mash, D. C., Masliah, E., and Sidhu, A. (2013) Identification of the sites of tau hyperphosphorylation and activation of tau kinases in synucleinopathies and Alzheimer's diseases. PLoS One 8, e75025
20. Matsuo, E. S., Shin, R. W., Billingsley, M. L., Van deVoorde, A., O'Connor, M., Trojanowski, J. Q., and Lee, V. M. (1994) Biopsy-derived adult human brain tau is phosphorylated at many of the same sites as Alzheimer's disease paired helical filament tau. Neuron 13, 989-1002
21. Grinberg, L. T., Wang, X., Wang, C., Sohn, P. D., Theofilas, P., Sidhu, M., Arevalo, J. B., Heinsen, H., Huang, E. J., Rosen, H., Miller, B. L., Gan, L., and Seeley, W. W. (2013) Argyrophilic grain disease differs from other tauopathies by lacking tau acetylation. Acta neuropathologica 125, 581-593
22. Shimura, H., Schwartz, D., Gygi, S. P., and Kosik, K. S. (2004) CHIP-Hsc70 complex ubiquitinates phosphorylated tau and enhances cell survival. J Biol Chem 279, 4869-4876
23. Liu, F., Iqbal, K., Grundke-Iqbal, I., Hart, G. W., and Gong, C. X. (2004) 0-GlcNAcylation regulates phosphorylation of tau: a mechanism involved in Alzheimer's disease. Proceedings of the National Academy of Sciences of the United States of America 101, 10804-10809
24. Lefebvre, T., Ferreira, S., Dupont-Wallois, L., Bussiere, T., Dupire, M. J., Delacourte, A., Michalski, J. C., and Caillet-Boudin, M. L. (2003) Evidence of a balance between phosphorylation and OGlcNAc glycosylation of Tau proteins—a role in nuclear localization. Biochimica et biophysica acta 1619, 167-176
25. Hanger, D. P., Byers, H. L., Wray, S., Leung, K.-Y., Saxton, M. J., Seereeram, A., Reynolds, C. H., Ward, M. A., and Anderton, B. H. (2007) Novel phosphorylation sites in tau from Alzheimer brain support a role for casein kinase 1 in disease pathogenesis. The Journal of biological chemistry 282, 23645-23654
26. Parker, C. E., Mocanu, V., Mocanu, M., Dicheva, N., and Warren, M. R. (2010) Mass Spectrometry for Post-Translational Modifications. In: Alzate, O., ed. Neuroproteomics, Boca Raton (Fla.)
27. Kang, M. J., Kim, C., Jeong, H., Cho, B. K., Ryou, A. L., Hwang, D., Mook-Jung, I., and Yi, E. C. (2013) Synapsin-1 and tau reciprocal O-GlcNAcylation and phosphorylation sites in mouse brain synaptosomes. Exp Mol Med 45, e29
28. Hanger, D. P., Betts, J. C., Loviny, T. L., Blackstock, W. P., and Anderton, B. H. (1998) New phosphorylation sites identified in hyperphosphorylated tau (paired helical filament-tau) from Alzheimer's disease brain using nanoelectrospray mass spectrometry. Journal of neurochemistry 71, 2465-2476
29. Dammer, E. B., Lee, A. K., Duong, D. M., Gearing, M., Lah, J. J., Levey, A. I., and Seyfried, N. T. (2015) Quantitative phosphoproteomics of Alzheimer's disease reveals cross-talk between kinases and small heat shock proteins. Proteomics 15, 508-519
30. Olsen, J. V., and Mann, M. (2013) Status of large-scale analysis of post-translational modifications by mass spectrometry. Molecular & cellular proteomics: MCP 12, 3444-3452
31. Wang, F., Song, C., Cheng, K., Jiang, X., Ye, M., and Zou, H. (2011) Perspectives of comprehensive phosphoproteome analysis using shotgun strategy. Anal Chem 83, 8078-8085
32. Merrill, A. E., and Coon, J. J. (2013) Quantifying proteomes and their post-translational modifications by stable isotope label-based mass spectrometry. Current opinion in chemical biology 17, 779-786
33. Venne, A. S., Kollipara, L., and Zahedi, R. P. (2014) The next level of complexity: crosstalk of posttranslational modifications. Proteomics 14, 513-524
34. Singh, S., Springer, M., Steen, J., Kirschner, M. W., and Steen, H. (2009) FLEXIQuant: a novel tool for the absolute quantification of proteins, and the simultaneous identification and quantification of potentially modified peptides. Journal of proteome research 8, 2201-2210
35. Singh, S. A., Winter, D., Bilimoria, P. M., Bonni, A., Steen, H., and Steen, J. A. (2012) FLEXIQinase, a mass spectrometry-based assay, to unveil multikinase mechanisms. Nat Methods 9, 504-508
36. Tepper, K., Biernat, J., Kumar, S., Wegmann, S., Timm, T., Hubschmann, S., Redecke, L., Mandelkow, E. M., Muller, D. J., and Mandelkow, E. (2014) Oligomer formation of tau protein hyperphosphorylated in cells. J Biol Chem 289, 34389-34407
37. Biernat, J., Gustke, N., Drewes, G., Mandelkow, E. M., and Mandelkow, E. (1993) Phosphorylation of Ser262 strongly reduces binding of tau to microtubules: distinction between PHF-like immunoreactivity and microtubule binding. Neuron 11, 153-163
38. Barghorn, S., Biernat, J., and Mandelkow, E. (2005) Purification of recombinant tau protein and preparation of Alzheimer-paired helical filaments in vitro. Methods in molecular biology 299, 35-51
39. Wisniewski, J. R., Zougman, A., Nagaraj, N., and Mann, M. (2009) Universal sample preparation method for proteome analysis. Nat Methods 6, 359-362
40. Escher, C., Reiter, L., MacLean, B., Ossola, R., Herzog, F., Chilton, J., MacCoss, M. J., and Rinner, 0. (2012) Using iRT, a normalized retention time for more targeted measurement of peptides. Proteomics 12, 1111-1121
41. Kessner, D., Chambers, M., Burke, R., Agus, D., and Mallick, P. (2008) ProteoWizard: open source software for rapid proteomics tools development. Bioinformatics 24, 2534-2536
42. Renard, B. Y., Kirchner, M., Monigatti, F., Ivanov, A. R., Rappsilber, J., Winter, D., Steen, J. A., Hamprecht, F. A., and Steen, H. (2009) When less can yield more—Computational preprocessing of MS/MS spectra for peptide identification. Proteomics 9, 4978-4984
43. MacLean, B., Tomazela, D. M., Shulman, N., Chambers, M., Finney, G. L., Frewen, B., Kern, R., Tabb, D. L., Liebler, D. C., and MacCoss, M. J. (2010) Skyline: an open source document editor for creating and analyzing targeted proteomics experiments. Bioinformatics 26, 966-968
44. Huillet, C., Adrait, A., Lebert, D., Picard, G., Trauchessec, M., Louwagie, M., Dupuis, A., Hittinger, L., Ghaleh, B., Le Corvoisier, P., Jaquinod, M., Garin, J., Bruley, C., and Brun, V. (2012) Accurate quantification of cardiovascular biomarkers in serum using Protein Standard Absolute Quantification (PSAQ) and selected reaction monitoring. Molecular & cellular proteomics: MCP 11, M111 008235
45. Picotti, P., Bodenmiller, B., Mueller, L. N., Domon, B., and Aebersold, R. (2009) Full dynamic range proteome analysis of S. cerevisiae by targeted proteomics. Cell 138, 795-806
46. Addona, T. A., Abbatiello, S. E., Schilling, B., Skates, S. J., Mani, D. R., Bunk, D. M., Spiegelman, C. H., Zimmerman, L. J., Ham, A. J., Keshishian, H., Hall, S. C., Allen, S., Blackman, R. K., Borchers, C. H., Buck, C., Cardasis, H. L., Cusack, M. P., Dodder, N. G., Gibson, B. W., Held, J. M., Hiltke, T., Jackson, A., Johansen, E. B., Kinsinger, C. R., Li, J., Mesri, M., Neubert, T. A., Niles, R. K., Pulsipher, T. C., Ransohoff, D., Rodriguez, H., Rudnick, P. A., Smith, D., Tabb, D. L., Tegeler, T. J., Variyath, A. M., Vega-Montoto, L. J., Wahlander, A., Waldemarson, S., Wang, M., Whiteaker, J. R., Zhao, L., Anderson, N. L., Fisher, S. J., Liebler, D. C., Paulovich, A. G., Regnier, F. E., Tempst, P., and Carr, S. A. (2009) Multi-site assessment of the precision and reproducibility of multiple reaction monitoring-based measurements of proteins in plasma. Nature biotechnology 27, 633-641
47. Keshishian, H., Addona, T., Burgess, M., Kuhn, E., and Carr, S. A. (2007) Quantitative, multiplexed assays for low abundance proteins in plasma by targeted mass spectrometry and stable isotope dilution. Molecular & cellular proteomics: MCP 6, 2212-2229
48. Unwin, R. D., Griffiths, J. R., and Whetton, A. D. (2009) A sensitive mass spectrometric method for hypothesis-driven detection of peptide post-translational modifications: multiple reaction monitoringinitiated detection and sequencing (MIDAS). Nat Protoc 4, 870-877
49. Prakash, A., Rezai, T., Krastins, B., Sarracino, D., Athanas, M., Russo, P., Ross, M. M., Zhang, H., Tian, Y., Kulasingam, V., Drabovich, A. P., Smith, C., Batruch, I., Liotta, L., Petricoin, E., Diamandis, E. P., Chan, D. W., and Lopez, M. F. (2010) Platform for establishing inter-laboratory reproducibility of selected reaction monitoring-based mass spectrometry peptide assays. J Proteome Res 9, 6678-6688
50. Baas, P. W., Pienkowski, T. P., and Kosik, K. S. (1991) Processes induced by tau expression in Sf9 cells have an axon-like microtubule organization. The Journal of cell biology 115, 1333-1344
51. Kosik, K. S., and McConlogue, L. (1994) Microtubule-associated protein function: lessons from expression in *Spodoptera frugiperda* cells. Cell motility and the cytoskeleton 28, 195-198
52. Biernat, J., and Mandelkow, E. M. (1999) The development of cell processes induced by tau protein requires phosphorylation of serine 262 and 356 in the repeat domain and is inhibited by phosphorylation in the proline-rich domains. Mol Biol Cell 10, 727-740
53. Zheng-Fischhofer, Q., Biernat, J., Mandelkow, E. M., Illenberger, S., Godemann, R., and Mandelkow, E. (1998) Sequential phosphorylation of Tau by glycogen synthase kinase-3beta and protein kinase A at Thr212 and Ser214 generates the Alzheimer-specific epitope of antibody AT100 and requires a paired-helical-filament-like conformation. European journal of biochemistry/FEBS 252, 542-552
54. Wray, S., Saxton, M., Anderton, B. H., and Hanger, D. P. (2008) Direct analysis of tau from PSP brain identifies new phosphorylation sites and a major fragment of N-terminally cleaved tau containing four microtubule-binding repeats. Journal of neurochemistry 105, 2343-2352
55. Hanger, D. P., Anderton, B. H., and Noble, W. (2009) Tau phosphorylation: the therapeutic challenge for neurodegenerative disease. Trends in molecular medicine 15, 112-119
56. Martin, L., Latypova, X., and Terro, F. (2011) Post-translational modifications of tau protein: implications for Alzheimer's disease. Neurochemistry International 58, 458-471
57. Noble, W., Hanger, D. P., Miller, C. C. J., and Lovestone, S. (2013) The importance of tau phosphorylation for neurodegenerative diseases. Frontiers in Neurology 4, 83
58. Brunden, K. R., Trojanowski, J. Q., and Lee, V. M.-Y. (2009) Advances in tau-focused drug discovery for Alzheimer's disease and related tauopathies. Nature Reviews Drug Discovery 8, 783-793
59. Sergeant, N., David, J. P., Lefranc, D., Vermersch, P., Wattez, A., and Delacourte, A. (1997) Different distribution of phosphorylated tau protein isoforms in Alzheimer's and Pick's diseases. FEBS Letters 412, 578-582
60. Sergeant, N., Delacourte, A., and Buee, L. (2005) Tau protein as a differential biomarker of tauopathies. Biochim Biophys Acta 1739, 179-197

What is claimed is:

1. A method comprising:
   (a) obtaining a first sample from a subject having or suspected of having a tauopathy; and
   (b) determining the amount of post translational modification (PTM) associated with a set of tau peptide fragments of a tau protein in the first sample, wherein determining the amount of PTM comprises:
      (i) providing a second sample comprising a labeled tau protein;
      (ii) mixing the first sample and the second sample at an initial mixing ratio of tau protein to labeled tau protein to form a mixture;
      (iii) subjecting the mixture to proteolytic digestion, generating tau peptide fragments and labeled tau peptide fragments;
      (iv) quantifying the abundance of the tau peptide fragments and the labeled tau peptide fragments by performing scheduled selected reaction monitoring acquisition using a selected transition list;
      (v) measuring the ratio of the abundance of the tau peptide fragments and the labeled tau peptide fragments;
      (vi) determining the amount of the tau PTMs associated with the set of tau peptide fragments by comparing the measured ratio for each tau peptide fragment to the initial mixing ratio, wherein the extent of deviation from the initial mixing ratio indicates the amount of PTMs in the tau peptide fragment, wherein the set of tau peptide fragments comprises: SEQ ID NO: 3, SEQ ID NO: 8, SEQ ID NO: 12, SEQ ID NO: 13, SEQ ID NO: 14, SEQ ID NO: 16, and SEQ ID NO: 17.

2. The method of claim 1, wherein the first sample is brain tissue, plasma, or cerebrospinal fluid (CSF).

3. The method of claim 1, wherein the tauopathy is selected from the group consisting of Alzheimer's disease (AD), Argyrophilic grain disease (AGD), Corticobasal degeneration (CBD), Pick's disease (PiD) and Progressive supranuclear palsy (PSP).

4. The method of claim 1, wherein the set of tau peptide fragments further comprise one or more of the peptides selected from the group consisting of

|  | SEQ ID NO: 1 |
|---|---|
| (QEFEVMEDHAGTYGLGDR), | |
| (DQGGYTMHQDQEGDTDAGLK), | SEQ ID NO: 2 |
| (STPTAEDVTAPLVDEGAPGK), | SEQ ID NO: 4 |
| (QAAAQPHTEIPEGTTAEEAGIGDTPSLEDEAAGHVTQAR), | SEQ ID NO: 5 |
| (TPPSSGEPPK), | SEQ ID NO: 6 |
| (SGYSSPGSPGTPGSR), | SEQ ID NO: 7 |
| (TPSLPTPPTREPK), | SEQ ID NO: 9 |
| (LQTAPVPMPDLK), | SEQ ID NO: 10 |
| (KLDLSNVQSK), and | SEQ ID NO: 11 |
| (TDHGAEIVYK). | SEQ ID NO: 15 |

5. The method of claim 1, wherein the set of tau peptide fragments further comprises SEQ ID NO: 7, SEQ ID NO: 9, SEQ ID NO: 10, SEQ ID NO: 11, SEQ ID NO: 14, SEQ ID NO: 16, and SEQ ID NO: 17.

6. The method of claim 1, wherein the set of tau peptide fragments further comprises SEQ ID NO: 3, SEQ ID NO: 9, SEQ ID NO: 12, SEQ ID NO: 14, SEQ ID NO: 16, and SEQ ID NO: 17.

7. The method of claim 1, wherein the set of tau peptide fragments further comprises SEQ ID NO: 3, SEQ ID NO: 4, SEQ ID NO: 7, SEQ ID NO: 9, SEQ ID NO: 10, SEQ ID NO: 11, SEQ ID NO: 13, and SEQ ID NO: 15.

8. The method of claim 1, wherein the set of tau peptide fragments further comprises SEQ ID NO: 4, SEQ ID NO: 11, SEQ ID NO: 12, SEQ ID NO: 13, SEQ ID NO: 14, SEQ ID NO: 15, SEQ ID NO: 16, and SEQ ID NO: 17.

9. The method of claim 1, wherein the set of tau peptide fragments further comprises SEQ ID NO: 9, SEQ ID NO: 10, SEQ ID NO: 11, SEQ ID NO: 12, SEQ ID NO: 13, SEQ ID NO: 14, and SEQ ID NO: 17.

10. The method of claim 1, wherein subjecting the mixture to proteolytic digestion is performed using one or more proteases.

11. The method of claim 1, wherein the post-translational modification is phosphorylation, glycosylation, glycation, prolyl-isomerization, cleavage or truncation, nitration, polyamination, ubiquitination, acetylation, methylation, dimethylation, trimethylation or sumoylation.

12. The method of claim 1, wherein the mixing ratio of labeled tau protein to tau protein is 4:1, 3:1, 2:1, 1:1, 1:2, 1:3 or 1:4.

13. The method of claim 1 further comprising treating the subject having the tauopathy.

14. The method of claim 1, wherein the set of tau peptide fragments consists of SEQ ID NO: 3, SEQ ID NO: 8, SEQ ID NO: 12, SEQ ID NO: 13, SEQ ID NO: 14, SEQ ID NO: 16, and SEQ ID NO: 17.

15. A method for quantifying the amount of post-translational modifications on a tau protein from a subject, the method comprising:
(a) providing a first sample comprising an unlabeled tau protein;
(b) providing a second sample comprising a labeled tau protein;
(c) mixing the first sample and the second sample at an initial mixing ratio of unlabeled tau protein to labeled tau protein to form a mixture;
(d) subjecting the mixture to proteolytic digestion, generating unlabeled tau peptide fragments and labeled tau peptide fragments;
(e) quantifying the abundance of the unlabeled tau peptide fragments and the labeled tau peptide fragments by performing scheduled selected reaction monitoring acquisition using a selected transition list;
(f) measuring the ratio of the abundance of the unlabeled tau peptide fragments and the labeled tau peptide fragments, and comparing the ratio for each peptide fragment to the initial mixing ratio, wherein the extent of deviation from the initial mixing ratio indicates the amount of PTMs in the unlabeled protein, wherein the tau peptide fragments comprise: SEQ ID NO: 3, SEQ ID NO: 8, SEQ ID NO: 12, SEQ ID NO: 13, SEQ ID NO: 14, SEQ ID NO: 16, and SEQ ID NO: 17; and
(g) quantifying the amount of PTMs in the tau protein of the first sample.

16. The method of claim 15, wherein the initial mixing ratio is 1:1.

17. The method of claim 15, wherein the labeled tau protein comprises one or more isotope-label amino acid residues.

18. The method of claim 15, wherein determining the abundance of the unlabeled tau peptide fragments and the labeled tau peptide fragments comprises identifying an ion signal associated with a peptide and/or its fragment ions.

19. A method for quantifying the amount of post-translational modifications on a tau protein, the method comprising:
(a) providing a mixture comprising a first sample comprising an unlabeled tau protein fragments and a second sample comprising labeled tau peptide fragments;
(b) quantifying the abundance of the unlabeled tau peptide fragments and the labeled tau peptide fragments by performing scheduled selected reaction monitoring acquisition using a selected transition list;
(c) measuring the ratio of the abundance of the unlabeled tau peptide fragments and the labeled tau peptide fragments, and comparing the ratio for each peptide fragment to the initial mixing ratio, wherein the extent of deviation from the initial mixing ratio indicates the amount of PTMs in the unlabeled protein, wherein the tau peptide fragments comprise: SEQ ID NO: 3, SEQ ID NO: 8, SEQ ID NO: 12, SEQ ID NO: 13, SEQ ID NO: 14, SEQ ID NO: 16, and SEQ ID NO: 17; and
(d) quantifying the amount of PTMs in the tau protein of the first sample.

20. The method of claim 19, wherein the mixture of step a) is prepared by (i) providing a first sample comprising an unlabeled tau protein; (ii) providing a second sample comprising a labeled tau protein; (ii) mixing the first sample and the second sample at an initial mixing ratio of unlabeled tau protein to labeled tau protein to form a mixture; (iv) subjecting the mixture to trypsin or Lys-C digestion, generating unlabeled tau peptide fragments and labeled tau peptide fragments; and (v) mixing the first sample and the second sample at an initial mixing ratio of unlabeled tau protein to labeled tau protein to form a mixture.

21. The method of claim 19, wherein the mixture of step a) is prepared by (i) providing a first sample comprising an unlabeled tau protein; (ii) subjecting the first sample to proteolytic digestion, generating unlabeled tau peptide fragments; (iii) providing a second sample comprising labeled tau peptide fragments, wherein the labeled tau peptide fragments are obtained from proteolytic digestion of a labeled tau protein; and (iv) mixing the first sample and the second sample at an initial mixing ratio of unlabeled tau protein to labeled tau protein to form a mixture.

* * * * *